(12) United States Patent  
Tsushima et al.

(10) Patent No.: US 6,916,822 B2  
(45) Date of Patent: Jul. 12, 2005

(54) PHENOXYALKYLAMINE DERIVATIVES USEFUL AS OPIOID δ RECEPTOR AGONISTS

(75) Inventors: Masaki Tsushima, Kanagawa (JP); Kaori Tadauchi, Kanagawa (JP); Kenji Asai, Tokyo (JP); Naoko Miike, Kanagawa (JP); Masako Imai, Kanagawa (JP); Toshiaki Kudo, Kanagawa (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 0 days.

(21) Appl. No.: 10/203,617

(22) PCT Filed: Feb. 16, 2001

(86) PCT No.: PCT/JP01/01116

§ 371 (c)(1),  
(2), (4) Date: Dec. 3, 2002

(87) PCT Pub. No.: WO01/60796

PCT Pub. Date: Aug. 23, 2001

(65) Prior Publication Data

US 2003/0171370 A1 Sep. 11, 2003

(30) Foreign Application Priority Data

Feb. 18, 2000 (JP) ........................................ 2000-040791

(51) Int. Cl.$^7$ ................ A61K 31/5747; A61K 31/1438; C07D 471/10
(52) U.S. Cl. ............................ 514/279; 546/17; 546/18
(58) Field of Search ...................... 546/17, 18; 514/279

(56) References Cited

U.S. PATENT DOCUMENTS

| | | | |
|---|---|---|---|
| 4,777,178 A | 10/1988 | Nakai et al. | |
| 5,100,902 A | 3/1992 | Peglion et al. | |
| 5,134,147 A | 7/1992 | Peglion et al. | |
| 5,536,716 A | 7/1996 | Chen et al. | |
| 5,614,523 A | * 3/1997 | Audia et al. | ........... 514/254.08 |
| 5,658,908 A | 8/1997 | Chang et al. | |
| 5,756,508 A | 5/1998 | Thompson et al. | |
| 5,922,887 A | 7/1999 | Dondio et al. | |
| 6,153,626 A | 11/2000 | Pelcman et al. | |
| 6,166,209 A | 12/2000 | Adam et al. | |
| 6,187,792 B1 | 2/2001 | Delorme et al. | |
| 6,258,825 B1 | 7/2001 | Ozaki et al. | |
| 6,262,104 B1 | 7/2001 | Dondio et al. | |
| 6,277,991 B1 | 8/2001 | Hohlweg et al. | |
| 6,399,635 B1 | 6/2002 | Pelcman et al. | |

FOREIGN PATENT DOCUMENTS

| | | |
|---|---|---|
| EP | 0206662 | 12/1986 |
| EP | 0428437 | 5/1991 |
| EP | 0561639 | 9/1993 |
| EP | 0990653 | 4/2000 |
| JP | 11189585 | 7/1999 |
| WO | 93/15062 | 8/1993 |
| WO | 94/13696 | 6/1994 |

(Continued)

OTHER PUBLICATIONS

Nate Hiroyuki et al., Chem. Pharm. Bull., vol. 35, No. 7 (1987), pp. 2825–2839.
C. J. Evans et al., Science, 1992, vol. 258, pp. 1952–1955.
B. L. Kieffer et al., Proc. Natl. Acad. Sci. USA, 1992, vol. 89, pp. 12048–12052.

(Continued)

*Primary Examiner*—Rita Desai  
(74) *Attorney, Agent, or Firm*—Greenblum & Bernstein, P.L.C.

(57) ABSTRACT

A medicament useful for preventive and/or therapeutic treatment of nerve system diseases which comprises, as an active ingredient, a compound represented by the following general formula (I) or a pharmacologically acceptable salt thereof:

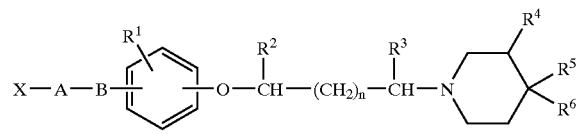

(I)

wherein, X represents a group represented by the following general formula (II), (III), (IV), (V), or (VI),

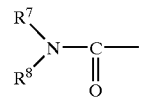

(II)

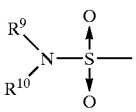

(III)

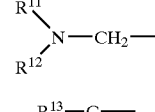

(IV)

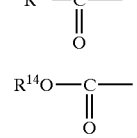

(V)

(VI)

"A" represents a saturated or unsaturated 3- to 6-membered carbocyclic group and the like, "B" represents CH$_2$ and the like, "n" represents 0 to 2, R$^1$ represents a hydrogen atom, a halogen atom and the like, R$^2$, R$^3$, and R$^7$ to R$^{14}$ represent a hydrogen atom, a lower alkyl group which may be substituted and the like, R$^4$ represents a hydrogen atom, a lower alkyl group which may be substituted and the like, R$^5$ represents a hydrogen atom, a halogen atom and the like, R$^6$ represents a saturated or unsaturated monocyclic or bicyclic carbocyclic group and the like, and R$^5$ and R$^6$, R$^7$ and R$^8$, R$^9$ and R$^{10}$, or R$^{11}$ and R$^{12}$ may bind to each other to form a cyclic structure.

10 Claims, No Drawings

FOREIGN PATENT DOCUMENTS

| | | |
|---|---|---|
| WO | 96/36620 | 11/1996 |
| WO | 97/10230 | 3/1997 |
| WO | 98/08816 | 3/1998 |
| WO | 98/28270 | 7/1998 |
| WO | 98/28275 | 7/1998 |
| WO | 98/42710 | 10/1998 |
| WO | 98/54168 | 12/1998 |
| WO | 99/29696 | 6/1999 |
| WO | 99/59997 | 11/1999 |

OTHER PUBLICATIONS

D. E. Moulin et al., Pain, 1985, 23, pp. 213–221.
J. J. Galligan et al., J. Pharm. Exp. Ther., 1984, vol. 229, pp. 641–648.
G. Dondio et al., Exp. Opin. Ther. Patents, 1999, 9, pp. 353–374.
S. N. Calderon et al., J. Med. Chem., 1994, 37, pp. 2125–2128.
C. Tashiro et al., Yakugaku Zasshi, 1989, vol. 109, pp. 93–101.
H. Obase et al., Chem. Pharm. Bull., 1983, vol. 31, pp. 3186–3197.
K. Freter, J. Org. Chem., 1975, vol. 40, pp. 2525–2529.
D. Beck et al., Helv. Chim. Acta, 1968, vol. 51, pp. 260–264.
M. S. Chambers et al., J. Med. Chem. 1992, 35, pp. 2033–2039.
K. Sasakura et al., Synth. Comm., 1988, 18, pp. 265–273.
W. E. Parham et al., J. Org. Chem., 1976, vol. 41, pp. 2628–2633.
English Language Abstract of JP 11–189585.

* cited by examiner

PHENOXYALKYLAMINE DERIVATIVES USEFUL AS OPIOID δ RECEPTOR AGONISTS

TECHNICAL FIELD

The present invention relates to phenoxyalkylamine derivatives, which have affinity for the opioid δ receptor and are useful in the medicinal field, and relates to medicaments comprising said compounds as an active ingredient.

BACKGROUND ART

Opioid receptors are mainly classified into three types, i.e., μ, δ and κ from a viewpoint of differences in pharmacological actions. On the basis of the discovery of an endogenous opioid peptide in 1970's, some progresses were made in studies about their mechanism of action. In 1990's, studies about opioid receptor structures advanced based on genetic analysis, and their mechanism of action has been being elucidated by the molecular biology. As also for the δ receptor, based on the success of cloning of δ receptor by Evans, Kieffer et al. in 1992, many studies have been vigorously performed in the medicinal and pharmaceutical fields by the molecular biology.

Although higher order functions of the opioid δ receptors have not yet been successfully elucidated, those already reported include that an opioid δ receptor agonist exhibits analgesic activity (D. E. Moulin et al., Pain, 1985, 23, 213), and that the opioid δ receptor agonist has an reducing effect on adverse reactions induced by an opioid μ receptor agonist and an opioid κ receptor agonist (Gallingan et. al., J. Pharm. Exp. Ther. 1984, 229, 641). Since the opioid δ receptor is known to be present widely in the central and peripheral nerve systems and considered to have a wide variety of functions, discovery of an effective and selective opioid δ receptor ligands can greatly contribute to therapeutic treatments of central nerve system diseases including schizophrenia, depression, cerebral apoplexy, epilepsy, Alzheimer's disease, and Parkinson's disease, and peripheral nerve system diseases including pains (Exp. Opin. ther. Patents, 1999, 9, 353).

Compounds related to the general formula (I) of the present invention are reported in J. Med. Chem. 1994, 37, 2125, WO93/15062, WO96/36620, WO97/10230, WO98/28270, WO98/28275 and the like. The compounds described in J. Med. Chem. 1994, 37, 2125 and WO93/15062 have very high affinity for δ receptors. However, these compounds have not been used clinically, because their productions are difficult due to three asymmetric centers, which are apparent from their chemical formulas, and they have poor pharmacokinetics. Derivatives having a structure with no asymmetric center are reported in WO96/36620, WO97/10230, WO98/28270, WO98/28275 and the like. However, their affinities for the δ receptor are undesirably lowered compared to the compounds described above. Thus, no compound has been reported which has a structure with no asymmetric center and high affinity for the δ receptor.

Further, the piperidine ring structure including $R^4$, $R^5$ and $R^6$ of the general formula (I) of the present invention is already known. However, no compound has been reported which has these partial structure and high affinity for the δ receptor.

DISCLOSURE OF THE INVENTION

An aim of the present invention is to provide a substance having affinity for the opioid δ receptor, in particular, to provide an effective and selective opioid δ receptor ligands. A further aim is to provide a medicament useful for preventive and/or therapeutic treatment of central nerve system diseases and peripheral nerve system diseases.

In the specification, the term "opioid δ receptor ligand" means a compound having an ability to bind to an opioid δ receptor, and comprehensively includes an agonist, antagonist, partial agonist, and inverse agonist for an opioid δ receptor.

In order to achieve the aim described above, the inventors of the present invention studied variety of compounds. As a result, they found that compounds represented by the following general formula (I) had high affinity for the opioid δ receptor, and achieved the present invention.

The present invention thus provides compounds represented by the following general formula (I):

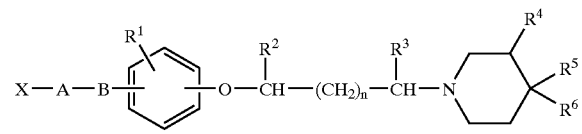

(I)

[in the formula, X represents the following group (II), (III), (IV), (V), or (VI):

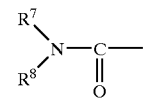

(II)

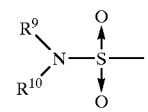

(III)

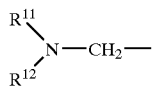

(IV)

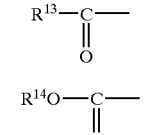

(V)

(VI)

"A" represents a saturated or unsaturated 3- to 6-membered carbocyclic group or a saturated or unsaturated monocyclic heterocyclic group containing one or more hetero atoms, "B" represents —CH$_2$—, —CHOH—, —(C=O)—, —CH$_2$CH$_2$—, or a single bond, "n" represents 0, 1 or 2, $R^1$ represents a hydrogen atom, a halogen atom, a lower alkyl group which may be substituted, a lower alkenyl group which may be substituted, a lower alkoxy group which may be substituted, a hydroxy group, a cyano group, an amino group, a N,N-di(lower alkyl)amino group, a N,N-di(substituted lower alkyl)amino group, a nitro group, a carbamoyl group, a N,N-di(lower alkyl)carbamoyl group, a N,N-di(substituted lower alkyl)carbamoyl group, a carboxyl group, a lower alkoxycarbonyl group which may be substituted or a lower alkylcarbonyl group which may be substituted, $R^2$, $R^3$, $R^7$, $R^8$, $R^9$, $R^{10}$, $R^{11}$, $R^{12}$, $R^{13}$, and $R^{14}$ each independently represent a hydrogen atom, a lower alkyl group which may be substituted or a lower alkenyl group which may be substituted, $R^4$ represents a hydrogen atom, a lower alkyl group which may be substituted, a lower alkenyl group which may be substituted, or a lower alkoxy group which may be substituted, $R^5$ represents a hydrogen atom, a halogen atom, a lower alkyl group which may be substituted, a lower alkenyl group which may be substituted, a lower alkoxy group which may be substituted, a hydroxy group, a cyano group, an amino group, a N,N-di(lower alkyl)amino group, a N,N-di(substituted lower alkyl)amino group, a carbamoyl group, a N,N-di(lower alkyl)carbamoyl group, a N,N-di(substituted lower alkyl)carbamoyl group, a carboxyl group, a lower alkoxycarbonyl group which may be substituted or a lower alkylcarbonyl group which may be substituted, $R^6$ represents a saturated or unsaturated monocyclic or bicyclic carbocyclic group, a saturated or unsaturated monocyclic or bicyclic heterocyclic group containing one or more hetero atoms, or a N-(lower alkyl)carbonyl-N-(substituted or unsubstituted phenyl)amino group, and $R^5$ and $R^6$, $R^7$ and $R^8$, $R^9$ and $R^{10}$, and $R^{11}$ and $R^{12}$ may bind to each other to form a cyclic structure] or salts thereof.

Further, the present invention provides medicaments comprising a substance consisting of the compounds represented by the general formula (I) and pharmacologically acceptable salts thereof. The preferred medicaments consist of a pharmaceutical composition comprising the substance described above and an additive for pharmaceutical preparations. These medicaments are useful for preventive treatment and/or therapeutic treatment of central nerve system diseases or peripheral nerve system diseases.

The present invention further provides an opioid δ receptor ligand comprising a substance consisting of the compounds represented by the general formula (I) and pharmacologically acceptable salts thereof.

The present invention still further provides use of substances consisting of the compounds represented by the general formula (I) and pharmacologically acceptable salts thereof for manufacture of the medicaments, and methods for preventive and/or therapeutic treatment of central nerve system diseases or peripheral nerve system diseases, which comprises a step of administering a preventively or therapeutically effective amount of a substance consisting of the compounds represented by the general formula (I) and pharmacologically acceptable salts thereof to a mammal including human.

BEST MODE FOR CARRYING OUT THE INVENTION

The present invention will be explained in detail. The entire disclosures of Japanese Patent Application No. 2000-40791 (filed on Feb. 18, 2000) are incorporated by reference in the disclosures of the specification.

Novel compounds of the present invention will be explained in more detail.

In the specification, a "lower alkyl group" or a "lower alkoxy group" as a substituent, or a "lower alkyl group" or "lower alkoxy group" constituting a part of a substituent means an alkyl or alkoxy group in a straight or branched chain, cyclic form, or any combination thereof having 1 to 6 carbon atoms, preferably 1 to 4 carbon atoms. Examples thereof include methyl, ethyl, n-propyl, isopropyl, cyclopropyl, n-butyl, i-butyl, s-butyl, t-butyl, n-pentyl, cyclopentyl, n-hexyl, cyclohexyl, methoxy, ethoxy, n-propoxy, isopropoxy, cyclopropoxy, n-butoxy, i-butoxy, s-butoxy, t-butoxy and the like. Similarly, a "lower alkenyl group" as a substituent means a straight, branched, or cyclic alkenyl group having 2 to 6 carbon atoms, preferably 2 to 4 carbon atoms, and examples thereof include vinyl group, allyl group and the like. In a group containing an alkenyl moiety, the number of double bonds contained in the alkenyl moiety is not particularly limited, and a double bond contained in the alkenyl moiety may either be in Z- or E-configuration.

The term "halogen atom" means a fluorine atom, chlorine atom, bromine atom or iodine atom unless otherwise specifically mentioned.

The term "hetero atom" means a hetero atom such as an oxygen atom, nitrogen atom, or sulfur atom, preferably an oxygen atom, nitrogen atom, or sulfur atom. A "heterocyclic ring" may contain two or more hetero atoms as ring-constituting atoms. In such compounds, two or more hetero atoms may be the same or different. A heterocyclic group means a residue of a heterocyclic ring obtained by removing one or more hydrogen atoms that bind to ring-constituting atoms.

In the formula (I), $R^7$ and $R^8$ in the group (II), $R^9$ and $R^{10}$ in the group (III), and $R^{11}$ and $R^{12}$ in the group (IV), which groups are represented by X, may independently bind to each other to form a cyclic structure. Examples of the ring include aziridine, azetidine, pyrrolidine, or piperidine. An unsaturated bond may exist in a part of these rings.

Further, $R^7$, $R^8$, $R^9$, $R^{10}$, $R^{11}$, $R^{12}$, $R^{13}$ and $R^{14}$ in the group (II), (III), (IV), (V) or (VI) represented by X preferably represent independently a hydrogen atom or a lower alkyl group, or $R^7$ and $R^8$ preferably bind to each other to represent pyrrolidine or piperidine. The group represented by X is preferably the group (II).

The integer represented by "n" is preferably 0.

Examples of the carbocyclic ring or heterocyclic ring that constitutes the saturated or unsaturated 3- to 6-membered carbocyclic group or saturated or unsaturated monocyclic heterocyclic group containing one or more hetero atoms represented by A include rings of cyclopropane, cyclobutane, cyclopentane, cyclohexane, cyclopropene, cyclobutene, cyclobutadiene, cyclopentene, cyclopentadiene, cyclohexene, cyclohexadiene, benzene, furan, pyrrole, thiophene, thiazole, oxazole, imidazole, isothiazole, isoxazole, pyrazole, triazole, pyridine, pyrimidine, pyrazine, pyridazine and the like. Preferred examples include cyclohexane, benzene, and furan, and benzene is more preferred. Further, X or B adjacent to A can exist at any substitutable position.

Further, these 3- to 6-membered carbocyclic groups or heterocyclic groups may have one or more substituents, and examples of the substituents include a lower alkyl group such as methyl group, a lower alkoxy group such as methoxy group, a lower alkenyl group such as allyl group, a halogen atom, a hydroxy group, a cyano group, an amino group, a N,N-di(lower alkyl)amino group, a N,N-di(substituted lower alkyl)amino group, a nitro group, a carbamoyl group, a N,N-di(lower alkyl)carbamoyl group such as N,N-dimethylcarbamoyl group, a N,N-di(substituted lower alkyl)carbamoyl group, a carboxyl group, a lower alkoxycarbonyl group which may be substituted such as a methoxycarbonyl group, a lower alkylcarbonyl group which may be substituted such as an acetyl group and the like. When the compounds have two or more substituents, the substituents may be the same or different. Positions of the substituents are not limited, and they can exist at any substitutable positions.

The group represented by "B" is preferably —CH$_2$—.

"n" is preferably 0.

R$^1$ is preferably a hydrogen atom or a lower alkoxy group which may be substituted.

R$^2$ and R$^3$ preferably represent a hydrogen atom or a lower alkyl group, most prefeably a hydrogen atom.

R$^4$ is preferably a hydrogen atom or a lower alkyl group which may be substituted, most preferably a hydrogen atom.

R$^5$ is preferably a hydrogen atom or a lower alkylcarbonyl group which may be substituted.

Examples of the carbocyclic ring that constitutes the saturated or unsaturated monocyclic or bicyclic carbocyclic group represented by R$^6$ include rings of cyclopentane, cyclohexane, benzene, indane, naphthalene and the like, and preferred are benzene, indane and naphthalene.

Examples of the heterocyclic ring that constitutes the saturated or unsaturated monocyclic or bicyclic heterocyclic group containing one or more hetero atoms represented by R$^6$ include rings of imidazole, benzofuran, indole, benzothiophene, benzothiazole, benzoxazole, benzimidazole, benzotriazole, benzisothiazole, benzisoxazole, quinoline, isoquinoline, quinazoline, pyridinoimidazole, benzoxazine and the like, and preferred examples are imidazole, benzofuran, indole, benzimidazole, benzotriazole, benzisothiazole, benzisoxazole, quinoline, isoquinoline, quinazoline and benzoxazine. More preferred R$^6$ is the following group (VII):

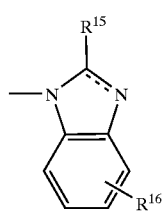

(VII)

[in the group, ==== represents a single bond or a double bond,

R$^{15}$ represents a hydrogen atom, a lower alkyl group which may be substituted, a lower alkenyl group which may be substituted, or an oxo group, and R$^{15}$ preferably represents a hydrogen atom, a lower alkyl group which may be substituted with hydroxy group or an oxo group, R$^{16}$ represents a hydrogen atom, a halogen atom, a lower alkyl group which may be substituted, a lower alkenyl group which may be substituted, a lower alkoxy group which may be substituted, a hydroxy group, a cyano group, an amino group, a N,N-di(lower alkyl)amino group, a N,N-di(substituted lower alkyl)amino group, a nitro group, a carbamoyl group, a N,N-di(lower alkyl)carbamoyl group, a N,N-di(substituted lower alkyl)carbamoyl group, a carboxyl group, a lower alkoxycarbonyl group which may be substituted or a lower alkylcarbonyl group which may be substituted, and R$^{16}$ preferably represents a hydrogen atom, a lower alkyl group or a lower alkoxy group].

An unsaturated bond as a part of the monocyclic or bicyclic carbocyclic group or monocyclic or bicyclic heterocyclic ring containing one or more hetero atoms represented by R$^6$ may be hydrogenated to form a saturated bond, or may be substituted with oxygen atom to form a cyclic ketone, cyclic amide (lactam), cyclic ester (lactone), or cyclic ureide structure. The substituting position of the adjacent piperidine ring may be an arbitrary substitutable position.

One or more hydrogen atoms on the saturated or unsaturated monocyclic or bicyclic carbocyclic group or saturated or unsaturated monocyclic or bicyclic heterocyclic ring containing one or more hetero atoms represented by R$^6$ may be substituted. Examples of the substituent include a lower alkyl group such as methyl group, a lower alkoxy group such as methoxy group, a lower alkenyl group such as allyl group, a halogen atom, a hydroxy group, a cyano group, an amino group, a N,N-di(lower alkyl)amino group, a N,N-di(substituted lower alkyl)amino group, a nitro group, a carbamoyl group, a N,N-di(lower alkyl)carbamoyl group such as N,N-dimethylcarbamoyl group, a N,N-di(substituted lower alkyl)carbamoyl group, carboxyl group, a lower alkoxycarbonyl group which may be substituted such as methoxycarbonyl group, a lower alkylcarbonyl group which may be substituted such as an acetyl group, an oxo group, a benzyl group, a hydroxymethyl group and the like, and preferred substituents are a lower alkyl group, a lower alkoxy group, a halogen atom, an oxo group, a benzyl group, and a hydroxymethyl group. When two or more substituents are included, these may be the same or different. The positions of the substituents are not limited, and they can exist at any substitutable positions.

Further, an example of the compounds wherein R$^5$ and R$^6$ bind to each other to form a cyclic structure include the compounds in which a spiro ring is formed. Specifically, examples include the following groups (VIII), (IX), (X), (XI), (XII), (XIII), (XIV), (XV), (XVI), and (XVII). Preferred groups are groups (VIII), (IX), (X), (XI), (XIII), (XVI), and (XVII), more preferred groups are groups (VIII) and (IX), and most preferred group is group (VIII) (in the following chemical formulas, a spiro ring is formed in each upper ring. In the formulas, each of two solid lines drawn from a ring represents a single bond that binds to the 3- or 5-position of the piperidine ring on which R$^5$ and R$^6$ substitute):

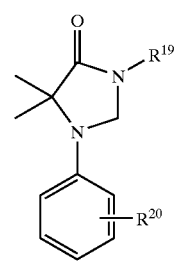

(IX)

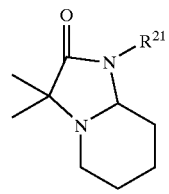

(X)

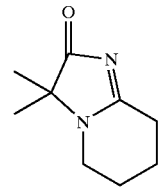

(XI)

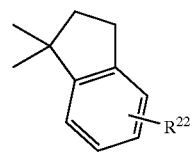
(XII)

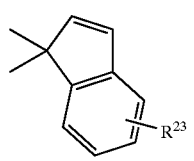
(XIII)

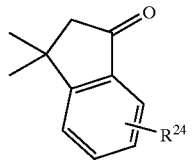
(XIV)

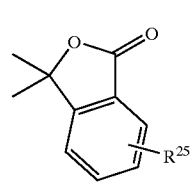
(XV)

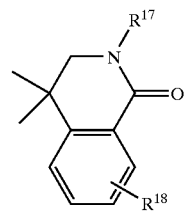
(VIII)

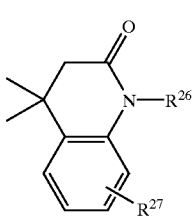
(XVI)

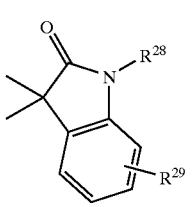
(XVII)

[in the formula, $R^{17}$ represents a hydrogen atom, a lower alkyl group which may be substituted or a lower alkenyl group which may be substituted, preferably a hydrogen atom, a lower alkyl group which may be substituted with a phenyl or a N,N-di(lower alkyl)carbamoylphenyl, $R^{18}$ represents a hydrogen atom, a halogen atom, a lower alkyl group which may be substituted, a lower alkenyl group which may be substituted, a lower alkoxy group which may be substituted, a hydroxy group, a cyano group, an amino group, a N,N-di(lower alkyl)amino group, a N,N-di(substituted lower alkyl)amino group, a nitro group, a carbamoyl group, a N,N-di(lower alkyl)carbamoyl group, a N,N-di(substituted lower alkyl)carbamoyl group, a carboxyl group, a lower alkoxycarbonyl group which may be substituted or a lower alkylcarbonyl group which may be substituted, preferably a hydrogen atom or a lower alkoxy group, $R^{19}$, $R^{21}$, $R^{26}$ and $R^{28}$ independently represent a hydrogen atom, a lower alkyl group which may be substituted or a lower alkenyl group which may be substituted, preferably a hydrogen atom or a lower alkyl group, $R^{20}$, $R^{22}$, $R^{23}$, $R^{24}$, $R^{25}$, $R^{27}$ and $R^{29}$ independently represent a hydrogen atom, a halogen atom, a lower alkyl group which may be substituted, a lower alkenyl group which may be substituted, a lower alkoxy group which may be substituted, a hydroxy group, a cyano group, an amino group, a N,N-di(lower alkyl)amino group, a N,N-di(substituted lower alkyl)amino group, a nitro group, a carbamoyl group, a N,N-di(lower alkyl)carbamoyl group, a N,N-di(substituted lower alkyl)carbamoyl group, a carboxyl group, a lower alkoxycarbonyl group which may be substituted or a lower alkylcarbonyl group which may be substituted, preferably a hydrogen atom].

The definition that a group represented by $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$ or $R^{29}$ "may be substituted" means that the group may have any one or more of substituents. When the group has two or more substituents, they may be the same or different. The positions of the substituents are not limited, and they can exist at any substitutable positions. Kinds of the substituents are not limited. Examples thereof include a lower alkyl group such as methyl group, a lower alkoxy group such as methoxy group, a lower alkenyl group such as allyl group, a halogen atom, a hydroxy group, a cyano group, an amino group, a N,N-di(lower alkyl)amino group, a N,N-di(substituted lower alkyl)amino group, a nitro group, a carbamoyl group, a N,N-di(lower alkyl)carbamoyl group such as N,N-dimethylcarbamoyl group, a N,N-di(substituted lower alkyl) carbamoyl group, a carboxyl group, a lower alkoxycarbonyl group which may be substituted such as methoxycarbonyl group, a lower alkylcarbonyl group which may be substituted such as acetyl group and saturated or unsaturated 3- to 6-membered carbocyclic group such as cyclopropyl, cyclopentyl, cyclohexyl, and phenyl (these carbocyclic groups may have one or more substituents, and examples of the substituents include a lower alkyl group such as methyl group, a lower alkoxy group such as methoxy group, a lower alkenyl group such as allyl group, a halogen atom, a hydroxy group, a cyano group, an amino group, a N,N-di(lower alkyl)amino group, a nitro group, a carbamoyl group, a N,N-di(lower alkyl)carbamoyl group such as N,N-dimethylcarbamoyl group, a carboxyl group, a (lower alkoxy)carbonyl group such as methoxycarbonyl group, a (lower alkyl)carbonyl group such as acetyl group and the like), and a phenyl group is preferred.

Further, examples of the substituents of the N,N-di (substituted lower alkyl)amino group, N,N-di(substituted lower alkyl)carbamoyl group, lower alkoxycarbonyl group which may be substituted, and lower alkylcarbonyl group which may be substituted include, for example, a lower alkoxy group, a lower alkenyl group, a halogen atom, a hydroxy group, a cyano group, an amino group, a N,N-di (lower alkyl)amino group, a nitro group, a carbamoyl group, a N,N-di(lower alkyl)carbamoyl group, a carboxyl group, a lower alkoxycarbonyl group, and a lower alkylcarbonyl group.

Among the compounds represented by the general formula (I), examples of a preferred class of compounds include those wherein $R^6$ represents the following group (VII):

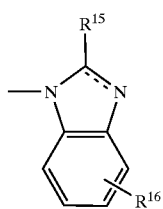

(VII)

[in the group, ═══ represents a single bond or a double bond, and R¹⁵ and R¹⁶ have the same meanings as defined above].

Examples of another preferred class of compounds include those wherein R⁵ and R⁶ form a cyclic structure and represent the following group (VIII):

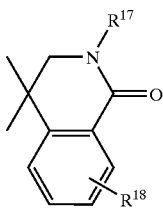

(VIII)

[in the group, R¹⁷ and R¹⁸ have the same meanings as defined above].

More preferred class of the compounds include those wherein X represents the group (II), (III), (V) or (VI), "A" represents a residue of a ring selected from the group consisting of benzene, cyclohexane and furan, "B" is —CH₂—, —CHOH—, —(C═O)—, —CH₂CH₂— or a single bond, "n" is 0, 1 or 2, R¹ is a hydrogen atom or a lower alkoxy group, R², R³, R⁷, R⁸, R⁹, R¹⁰, R¹³ and R¹⁴ each independently represent a hydrogen atom or a lower alkyl group which may be substituted, R⁴ is a hydrogen atom or a lower alkyl group which may be substituted, R⁵ is a hydrogen atom or a lower alkylcarbonyl group which may be substituted, R⁶ is a residue of a ring selected from the group consisting of benzene, naphthalene, indane, benzofuran, imidazole, benzimidazole, indole, quinoline, benzotriazole, benzisothiazole, benzisoxazole, quinazoline, isoquinoline and benzoxazine (a hydrogen atom on the ring may be replaced with halogen, oxo, lower alkyl, hydroxymethyl, lower alkoxy or benzyl), or R⁵ and R⁶ bind to each other to form a residue of a ring selected from the group consisting of indane, imidazole, N-phenylimidazolidine, isoquinoline, quinoline and benzofuran (a hydrogen atom on the ring may be replaced with oxo, lower alkyl or lower alkoxy), and R⁷ and R⁸ bind to each other to form pyrrolidine or piperidine.

Examples of further preferred class of the compounds include those wherein X represents the group (II).

In the present invention, among the compounds represented by the general formula (I), particularly preferred compounds are as follows.

1. 1-[2-[2-(4-Diethylcarbamoylbenzyl)phenoxy]ethyl]-4-(1,3-dihydro-2H-benzimidazol-2-on-1-yl)piperidine
2. 1-[3-[2-(4-Diethylcarbamoylbenzyl)phenoxy]propyl]-4-(1,3-dihydro-2H-benzimidazol-2-on-1-yl)piperidine
3. 8-[2-[2-(4-Diethylcarbamoylbenzyl)phenoxy]ethyl]-1-phenyl-1,3,8-triazaspiro[4,5]decan-4-one
4. 3-Benzyl-8-[2-[2-(4-diethylcarbamoylbenzyl)phenoxy]ethyl]-1-phenyl-1,3,8-triazaspiro[4,5]decan-4-one
5. 3-Cyclopropylmethyl-8-[2-[2-(4-diethylcarbamoylbenzyl)phenoxy]ethyl]-1-phenyl-1,3,8-triazaspiro[4,5]decan-4-one
6. 1-[4-[2-(4-Diethylcarbamoylbenzyl)phenoxy]butyl]-4-(1,3-dihydro-2H-benzimidazol-2-on-1-yl)piperidine
7. 8-[4-[2-(4-Diethylcarbamoylbenzyl)phenoxy]butyl]-1-phenyl-1,3,8-triazaspiro[4,5]decan-4-one
8. 8-[3-[2-(4-Diethylcarbamoylbenzyl)phenoxy]propyl]-1-phenyl-1,3,8-triazaspiro[4,5]decan-4-one
9. 4-(3-Benzyl-1,3-dihydro-2H-benzimidazol-2-on-1-yl)-1-[2-[2-(4-diethylcarbamoylbenzyl)phenoxy]ethyl]piperidine
10. 4-(3-Cyclopropylmethyl-1,3-dihydro-2H-benzimidazol-2-on-1-yl)-1-[2-[2-(4-diethylcarbamoylbenzyl)phenoxy]ethyl]piperidine
11. 1'-[2-[2-(4-Diethylcarbamoylbenzyl)phenoxy]ethyl]hexahydrospiro-[imidazo[1,2-a]pyridine-3(2H),4'-piperidin]-2-one
12. 1'-[2-[2-(4-Diethylcarbamoylbenzyl)phenoxy]ethyl]-5,6,7,8-tetrahydrospiro[imidazo[1,2-a]pyridine-3(2H),4'-piperidin]-2-one
13. 4-(1,3-Dihydro-2H-benzimidazol-2-on-1-yl)-1-[2-[2-(4-dimethylcarbamoylbenzyl)-phenoxy]ethyl]piperidine
14. 8-[2-[2-(4-Dimethylcarbamoylbenzyl)phenoxy]ethyl]-1-phenyl-1,3,8-triazaspiro[4,5]decan-4-one
15. 4-(1,3-Dihydro-2H-benzimidazol-2-on-1-yl)-1-[2-[2-(4-pyrrolidinocarbonylbenzyl)-phenoxy]ethyl]piperidine
16. 1-Phenyl-8-[2-[2-(4-pyrrolidinocarbonylbenzyl)phenoxy]ethyl]-1,3,8-triazaspiro[4,5]decan-4-one
17. 1-[2-[3-(4-Diethylcarbamoylbenzyl)phenoxy]ethyl]-4-(1,3-dihydro-2H-benzimidazol-2-on-1-yl)piperidine
18. 8-[2-[3-(4-Diethylcarbamoylbenzyl)phenoxy]ethyl]-1-phenyl-1,3,8-triazaspiro[4,5]decan-4-one
19. 1-[2-[4-(4-Diethylcarbamoylbenzyl)phenoxy]ethyl]-4-(1,3-dihydro-2H-benzimidazol-2-on-1-yl)piperidine
20. 8-[2-[4-(4-Diethylcarbamoylbenzyl)phenoxy]ethyl]-1-phenyl-1,3,8-triazaspiro[4,5]decan-4-one
21. 4-(1,3-Dihydro-2H-benzimidazol-2-on-1-yl)-1-[2-[2-(4-piperidinocarbonylbenzyl)-phenoxy]ethyl]piperidine
22. 1-Phenyl-8-[2-[2-(4-piperidinocarbonylbenzyl)phenoxy]ethyl]-1,3,8-triazaspiro[4,5]decan-4-one
23. 1-[2-[2-(4-Diethylcarbamoylbenzoyl)phenoxy]ethyl]-4-(1,3-dihydro-2H-benzimidazol-2-on-1-yl)piperidine
24. 8-[2-[2-(4-Diethylcarbamoylbenzoyl)phenoxy]ethyl]-1-phenyl-1,3,8-triazaspiro[4,5]decan-4-one
25. 1-[2-[2-[1-(4-Diethylcarbamoylphenyl)-1-hydroxymethyl]phenoxy]ethyl]-4-(1,3-dihydro-2H-benzimidazol-2-on-1-yl)piperidine
26. 8-[2-[2-[1-(4-Diethylcarbamoylphenyl)-1-hydroxymethyl]phenoxy]ethyl]-1-phenyl-1,3,8-triazaspiro[4,5]decan-4-one
27. 1-[2-[2-(3-Diethylcarbamoylbenzyl)phenoxy]ethyl]-4-(1,3-dihydro-2H-benzimidazol-2-on-1-yl)piperidine
28. 8-[2-[2-(3-Diethylcarbamoylbenzyl)phenoxy]ethyl]-1-phenyl-1,3,8-triazaspiro[4,5]decan-4-one
29. 1-[2-[2-(4-Diethylcarbamoylbenzyl)phenoxy]propyl]-4-(1,3-dihydro-2H-benzimidazol-2-on-1-yl)piperidine
30. 8-[2-[2-(4-Diethylcarbamoylbenzyl)phenoxy]propyl]-1-phenyl-1,3,8-triazaspiro[4,5]decan-4-one
31. 4-(1,3-Dihydro-2H-benzimidazol-2-on-1-yl)-1-[2-[2-(4-diisopropylcarbamoylbenzyl)-phenoxy]ethyl]piperidine
32. 8-[2-[2-(4-Diisopropylcarbamoylbenzyl)phenoxy]ethyl]-1-phenyl-1,3,8-triazaspiro[4,5]decan-4-one
33. 1-[2-[2-[2-(4-Diethylcarbamoylphenyl)ethyl]phenoxy]ethyl]-4-(1,3-dihydro-2H-benzimidazol-2-on-1-yl)piperidine 34. 8-[2-[2-[2-(4-Diethylcarbamoylphenyl)ethyl]phenoxy]ethyl]-1-phenyl-1,3,8-triazaspiro[4,5]decan-4-one
35. 1-[2-[2-(4-Diethylcarbamoylbenzyl)phenoxy]ethyl]-4-(1,3-dihydro-3-methyl-2H-benzimidazol-2-on-1-yl)piperidine
36. 8-[2-[2-(4-Diethylcarbamoylbenzyl)phenoxy]ethyl]-3-methyl-1-phenyl-1,3,8-triazaspiro[4,5]decan-4-one
37. 1-[2-[2-(4-Diethylcarbamoylbenzyl)phenoxy]ethyl]-4-(2,3-dihydro-1H-indol-2-on-3-yl)piperidine
38. 1-[2-[2-(4-Diethylcarbamoylbenzyl)phenoxy]ethyl]-4-(1,2,3,4-tetrahydroquinolin-1-yl)piperidine
39. 1-[2-[2-(4-Diethylcarbamoylbenzyl)phenoxy]ethyl]-4-(1,2,3,4-tetrahydronaphthalen-1-yl)piperidine
40. 1-[2-[2-(4-Diethylcarbamoylphenyl)phenoxy]ethyl]-4-(1,3-dihydro-2H-benzimidazol-2-on-1-yl)piperidine
41. 8-[2-[2-(4-Diethylcarbamoylphenyl)phenoxy]ethyl]-1-phenyl-1,3,8-triazaspiro[4,5]decan-4-one
42. 1-[2-[2-(4-Diethylcarbamoylbenzyl)phenoxy]ethyl]-4-(indan-1-yl)piperidine
43. 1-[2-[3-(4-Diethylcarbamoylphenyl)phenoxy]ethyl]-4-(1,3-dihydro-2H-benzimidazol-2-on-1-yl)piperidine
44. 8-[2-[3-(4-Diethylcarbamoylphenyl)phenoxy]ethyl]-1-phenyl-1,3,8-triazaspiro[4,5]decan-4-one
45. 1-[2-[3-(3-Diethylcarbamoylphenyl)phenoxy]ethyl]-4-(1,3-dihydro-2H-benzimidazol-2-on-1-yl)piperidine
46. 8-[2-[3-(3-Diethylcarbamoylphenyl)phenoxy]ethyl]-1-phenyl-1,3,8-triazaspiro[4,5]decan-4-one
47. 1-[2-[2-(4-Diethylcarbamoylbenzyl)phenoxy]ethyl]-4-(1H-benzimidazol-1-yl)piperidine
48. 1-[2-[2-(4-Diethylcarbamoylbenzyl)phenoxy]ethyl]-4-(1,2,3,4-tetrahydroquinolin-2-on-1-yl)piperidine
49. 4-Acetyl-1-[2-[2-(4-diethylcarbamoylbenzyl)phenoxy]ethyl]-4-phenylpiperidine
50. 1-[2-[2-(3-Diethylcarbamoylphenyl)phenoxy]ethyl]-4-(1,3-dihydro-2H-benzimidazol-2-on-1-yl)piperidine
51. 8-[2-[2-(3-Diethylcarbamoylphenyl)phenoxy]ethyl]-1-phenyl-1,3,8-triazaspiro[4,5]decan-4-one
52. 1-[1-[2-(4-Diethylcarbamoylbenzyl)phenoxymethyl]ethyl]-4-(1,3-dihydro-2H-benzimidazol-2-on-1-yl)piperidine
53. 4-(1H-Benzotriazol-1-yl)-1-[2-[2-(4-diethylcarbamoylbenzyl)phenoxy]ethyl]-piperidine
54. 1-[2-[2-(4-Diethylcarbamoylbenzyl)phenoxy]ethyl]-4-(2,3-dihydro-1H-indol-1-yl)piperidine
55. 8-[1-[2-(4-Diethylcarbamoylbenzyl)phenoxymethyl]ethyl]-1-phenyl-1,3,8-triazaspiro[4,5]decan-4-one
56. 4-(1H-Benzimidazol-1-yl)-1-[1-[2-(4-diethylcarbamoylbenzyl)phenoxymethyl]-ethyl]piperidine
57. 1-[2-[2-(4-Diethylcarbamoylbenzyl)phenoxy]ethyl]-4-(6-fluoro-1,2-benzisothiazol-3-yl)piperidine
58. 1-[2-[2-(4-Diethylcarbamoylbenzyl)phenoxy]ethyl]-4-(6-fluoro-1,2-benzisoxazol-3-yl)piperidine
59. 1-[2-[2-(4-Diethylcarbamoylbenzyl)phenoxy]ethyl]-4-(1H-indol-3-yl)piperidine
60. 1'-[2-[2-(4-Diethylcarbamoylbenzyl)phenoxy]ethyl]-2,3-dihydrospiro[1H-indene-1,4'-piperidine]
61. (R)-1-[1-[2-(4-Diethylcarbamoylbenzyl)phenoxymethyl]ethyl]-4-(1,3-dihydro-2H-bezimidazol-2-on-1-yl)piperidine
62. (S)-1-[1-[2-(4-Diethylcarbamoylbenzyl)phenoxymethyl]ethyl]-4-(1,3-dihydro-2H-benzimidazol-2-on-1-yl)piperidine
63. 1-[2-[2-(4-Diethylcarbamoylbenzyl)phenoxy]ethyl]-4-(1,2,3,4-tetrahydroquinazolin-2-on-1-yl)piperidine
64. 1'-[2-[2-(4-Diethylcarbamoylbenzyl)phenoxy]ethyl]-2,3-dihydrospiro[isoquinoline-4(1H),4'-piperidin]-1-one
65. 1-[2-[2-(4-Diethylcarbamoylbenzyl)phenoxy]ethyl]spiro[piperidine-4,4'(1'H)-quinolin]-2'(3'H)-one
66. 1'-[2-[2-(4-Diethylcarbamoylbenzyl)phenoxy]ethyl]spiro[1H-indene-1,4'-piperidin]-3(2H)-one
67. 1-[2-[2-(4-Diethylcarbamoylbenzyl)phenoxy]ethyl]-4-(3,3-dimethyl-2,3-dihydro-1H-indol-2-on-1-yl)piperidine
68. 1-[2-[2-(4-Diethylcarbamoylbenzyl)phenoxy]ethyl]-4-phenylpiperidine
69. 1-[2-[2-(4-Diethylcarbamoylbenzyl)phenoxy]ethyl]-4-(1H-indol-1-yl)piperidine
70. 1'-[2-[2-(4-Diethylcarbamoylbenzyl)phenoxy]ethyl]spiro[3H-indole-3,4'-piperidin]-2(1H)-one
71. 1'-[2-[2-(4-Diethylcarbamoylbenzyl)phenoxy]ethyl]spiro[1H-indene-1,4'-piperidine]
72. 1-[2-[2-(4-Diethylcarbamoylbenzyl)phenoxy]ethyl]-4-(2-methyl-1H-benzimidazol-1-yl)piperidine
73. 1-[2-[2-(4-Diethylcarbamoylbenzyl)phenoxy]ethyl]-4-(3,4-dihydro-2H-1,4-benzoxazin-3-on-4-yl)piperidine
74. 1-[2-[2-(4-Diethylcarbamoylbenzyl)phenoxy]ethyl]-4-(1H-imidazol-1-yl)piperidine
75. 1-[1-[2-(4-Diethylcarbamoylbenzyl)phenoxymethyl]propyl]-4-(1,3-dihydro-2H-benzimidazol-2-on-1-yl)piperidine
76. 8-[1-[2-(4-Diethylcarbamoylbenzyl)phenoxymethyl]propyl]-1-phenyl-1,3,8-triazaspiro[4,5]decan-4-one
77. 1'-[2-[2-(4-Diethylcarbamoylbenzyl)phenoxy]ethyl]spiro[isobenzofuran-1(3H),4'-piperidin]-3-one
78. 1-[2-[2-(4-Diethylcarbamoylbenzyl)phenoxy]ethyl]-4-(6-fluoro-1H-indol-3-yl)piperidine
79. 1-[2-[2-(4-Diethylcarbamoylbenzyl)-4-methoxyphenoxy]ethyl]-4-(1,3-dihydro-2H-benzimidazol-2-on-1-yl)piperidine
80. 8-[2-[2-(4-Diethylcarbamoylbenzyl)-4-methoxyphenoxy]ethyl]-1-phenyl-1,3,8-triazaspiro[4,5]decan-4-one
81. 1-[2-[2-(4-Diethylcarbamoylbenzyl)phenoxy]ethyl]-4-(1,3-dihydro-7-methyl-2H-benzimidazol-2-on-1-yl)piperidine
82. 1-[2-[2-(4-Diethylcarbamoylbenzyl)phenoxy]ethyl]-4-(5-fluoro-1,3-dihydro-2H-benzimidazol-2-on-1-yl)piperidine
83. 1'-[2-[2-(4-Diethylcarbamoylbenzyl)phenoxy]ethyl]-2,3-dihydro-5-methylspiro[isoquinoline-4(1H),4'-piperidin]-1-one
84. 1-[2-[2-(4-Diethylcarbamoylbenzyl)phenoxy]ethyl]-4-(2-hydroxymethyl-1H-benzimidazol-1-yl)piperidine
85. 1-[2-[2-(4-Diethylcarbamoylbenzyl)phenoxy]ethyl]-4-[2-(2-hydroxyethyl)-1H-benzimidazol-1-yl]piperidine
86. 1-[2-[2-(4-Diethylcarbamoylbenzyl)phenoxy]ethyl]-4-(2-hydroxymethyl-7-methyl-1H-benzimidazol-1-yl)piperidine
87. 1-[2-[2-(4-Diethylcarbamoylbenzyl)phenoxy]ethyl]-4-(2-hydroxymethyl-7-methoxy-1H-benzimidazol-1-yl)piperidine
88. 1-[2-[2-(4-Diethylcarbamoylbenzyl)phenoxy]ethyl]-4-(1,3-dihydro-2H-benzimidazol-2-on-1-yl)-3-methylpiperidine
89. 1-[2-[2-(4-Diethylaminosulfonylbenzyl)phenoxy]ethyl]-4-(2-hydroxymethyl-1H-benzimidazol-1-yl)piperidine
90. 1-[2-[2-(4-Diethylaminosulfonylbenzyl)phenoxy]ethyl]-4-(1,3-dihydro-2H-benzimidazol-2-on-1-yl)piperidine
91. 8-[2-[2-(4-Diethylaminosulfonylbenzyl)phenoxy]ethyl]-1-phenyl-1,3,8-triazaspiro[4,5]decan-4-one
92. 1-[2-[2-(3-Diethylaminosulfonylbenzyl)phenoxy]ethyl]-4-(2-hydroxymethyl-1H-benzimidazol-1-yl)piperidine
93. 1-[2-[2-(3-Diethylaminosulfonylbenzyl)phenoxy]ethyl]-4-(1,3-dihydro-2H-benzimidazol-2-on-1-yl)piperidine 94. 8-[2-[2-(3-Diethylaminosulfonylbenzyl)phenoxy]ethyl]-1-phenyl-1,3,8-triazaspiro[4,5]decan-4-one
95. 1-[2-[2-[(5-Diethylcarbamoylfuran-2-yl)methyl]phenoxy]ethyl]-4-(1,3-dihydro-2H-benzimidazol-2-on-1-yl)piperidine
96. 8-[2-[2-[(5-Diethylcarbamoylfuran-2-yl)methyl]phenoxy]ethyl]-1-phenyl-1,3,8-triazaspiro[4,5]decan-4-one
97. 1-[2-[2-[(5-Diethylcarbamoylfuran-2-yl)methyl]phenoxy]ethyl]-4-(2-hydroxymethyl-1H-benzimidazol-1-yl)piperidine
98. 1'-[2-[2-(4-Diethylcarbamoylbenzyl)phenoxy]ethyl]-2,3-dihydro-5-methoxyspiro[isoquinoline-4(1H),4'-piperidin]-1-one
99. 1-[2-[2-[(4-Diethylaminomethyl)benzyl]phenoxy]ethyl]-4-(2-hydroxymethyl-1H-benzimidazol-1-yl)piperidine
100. 1-[2-[2-(4-Diethylcarbamoylbenzyl)phenoxy]ethyl]-4-(2-hydroxymethyl-1H-benzimidazol-1-yl)-3-methylpiperidine
101. 1-[2-[2-(3-Diethylcarbamoylbenzyl)phenoxy]ethyl]-4-(2-hydroxymethyl-1H-benzimidazol-1-yl)piperidine
102. 1-[2-[2-(3-Diethylcarbamoylbenzyl)phenoxy]ethyl]-4-(2-hydroxymethyl-7-methyl-1H-benzimidazol-1-yl)piperidine
103. 1-[2-[2-(4-Isobutyloxycarbonylbenzyl)phenoxy]ethyl]-4-(2-hydroxymethyl-1H-benzimidazol-1-yl)piperidine
104. 1-[2-[2-(4-Isobutyloxycarbonylbenzyl)phenoxy]ethyl]-4-(1,3-dihydro-2H-benzimidazol-2-on-1-yl)piperidine
105. 8-[2-[2-(4-Isobutyloxycarbonylbenzyl)phenoxy]ethyl]-1-phenyl-1,3,8-triazaspiro[4,5]decan-4-one
106. 1-[2-[2-(4-Carboxybenzyl)phenoxy]ethyl]-4-(2-hydroxymethyl-1H-benzimidazol-1-yl)piperidine
107. 1-[2-[2-[trans-(4-Diethylcarbamoylcyclohexyl)methyl]phenoxy]ethyl]-4-(1,3-dihydro-2H-benzimidazol-2-on-1-yl)piperidine
108. 8-[2-[2-[trans-(4-Diethylcarbamoylcyclohexyl)methyl]phenoxy]ethyl]-1-phenyl-1,3,8-triazaspiro[4,5]decan-4-one
109. 1-[2-[2-[trans-(4-Diethylcarbamoylcyclohexyl)methyl]phenoxy]ethyl]-4-(2-hydroxymethyl-1H-benzimidazol-1-yl)piperidine
110. 4-(2-Hydroxymethyl-1H-benzimidazol-1-yl)-1-[2-[2-[4-(1-methylbutyryl)benzyl]phenoxy]ethyl]piperidine
111. 1-[2-[2-[cis-(4-Diethylcarbamoylcyclohexyl)methyl]phenoxy]ethyl]-4-(1,3-dihydro-2H-benzimidazol-2-on-1-yl)piperidine
112. 8-[2-[2-[cis-(4-Diethylcarbamoylcyclohexyl)methyl]phenoxy]ethyl]-1-phenyl-1,3,8-triazaspiro[4,5]decan-4-one
113. 1-[2-[2-[cis-(4-Diethylcarbamoylcyclohexyl)methyl]phenoxy]ethyl]-4-(2-hydroxymethyl-1H-benzimidazol-1-yl)piperidine
114. 2-Benzyl-1'-[2-[2-(4-diethylcarbamoylbenzyl)phenoxy]ethyl]-2,3-dihydrospiro-[isoquinoline-4(1H),4'-piperidin]-1-one
115. 2-(4-Diethylcarbamoylbenzyl)-1'-[2-[2-(4-diethylcarbamoylbenzyl)phenoxy]ethyl]-2,3-dihydrospiro[isoquinoline-4(1H),4'-piperidin]-1-one
116. 2-Cyclopropylmethyl-1'-[2-[2-(4-diethylcarbamoylbenzyl)phenoxy]ethyl]-2,3-dihydrospiro[isoquinoline-4(1H),4'-piperidin]-1-one
117. 2-(3-Diethylcarbamoylbenzyl)-1'-[2-[2-(4-diethylcarbamoylbenzyl)phenoxy]ethyl]-2,3-dihydrospiro[isoquinoline-4(1H),4'-piperidin]-1-one
118. 4-(N-Acetylanilino)-1-[2-[2-(4-diethylcarbamoylbenzyl)phenoxy]ethyl]piperidine Methods for preparing the novel compounds of the present invention will be explained in more detail. The novel compounds of the present invention can be produced by the methods described below.

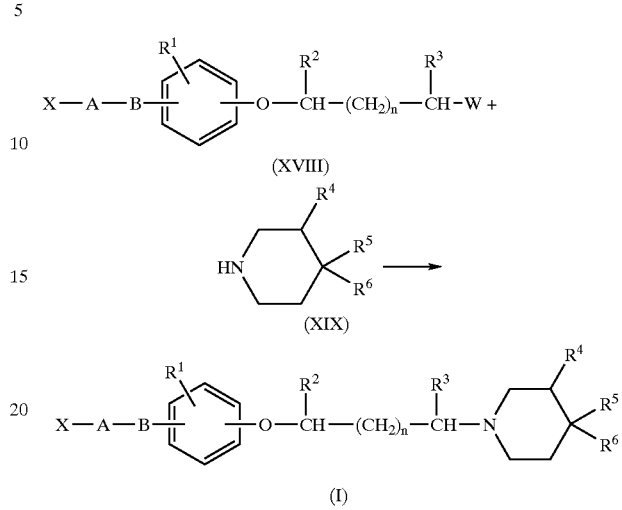

[in the formula, X, A, B, $R^1$, $R^2$, $R^3$, $R^4$, $R^5$, $R^6$, and n have the same meaning as those defined in the general formula (I), W represents a halogen atom excluding a fluorine atom or represents a leaving group such as p-toluenesulfonyloxy group, methanesulfonyloxy group or trifluoromethanesulfonyloxy group].

The compounds (XVIII) can be prepared by the methods described in J. Med. Chem. 1994, 37, 2125 and WO97/10230 with modification, and a specific preparation method is described in Reference Example 1 which follows.

The compounds (XIX) can be obtained as a commercially available reagent or can also be obtained in accordance with a known method or a known method with modification.

The compounds (I) of the present invention can be obtained by a reaction of a compound (XVIII) and a compound (XIX) in a solvent that is not involved in the reaction (for example, dichloromethane, tetrahydrofuran, methyl ethyl ketone, N,N-dimethylformamide, dimethyl sulfoxide etc.) in the presence of a base (e.g., pyridine, triethylamine, diisopropylethylamine, 4-dimethylaminopyridine, potassium carbonate, sodium carbonate etc.) at a certain reaction temperature of which lower limit is 20° C. and upper limit is 100° C., preferably lower limit is 20° C. and upper limit is 50° C., for a reaction time of which lower limit is 2 hours and upper limit is 48 hours, preferably lower limit is 16 hours and upper limit is 24 hours.

Further, among the novel compounds of the present invention, the compounds (XXI) wherein $R^3$ is H can also be produced by the method described below.

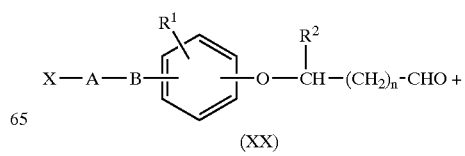

-continued

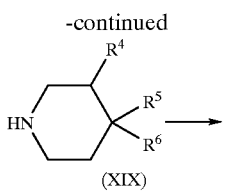

(XIX)

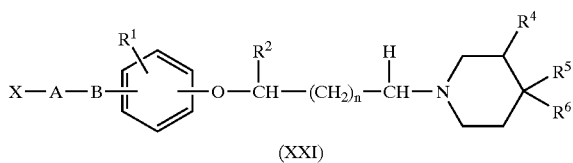

(XXI)

[in the formula, X, A, B, $R^1$, $R^2$, $R^4$, $R^5$, $R^6$, and n have the same meanings as those defined in the general formula (I).]

In a manner to the preparation of the compounds (XVIII), the compounds (XX) can be produced by the methods described in J. Med. Chem. 1994, 37, 2125 and WO97/10230 with modification, and a specific preparation method is described in Reference Example 2 below.

Among the compounds of the general formula (I) according to the present invention, the compounds (XXI) wherein $R^3$ is H can be obtained by a reaction of a compound (XX) and a compound (XIX) in a solvent that is not involved in the reaction (e.g., dichloroethane, tetrahydrofuran, dimethyl sulfoxide and the like) in the presence of sodium triacetoxyborohydride and acetic acid at a reaction temperature of which lower limit is 20° C. and upper limit is 50° C., preferably lower limit is 20° C. and upper limit is 30° C., for a reaction time of which lower limit is 2 hours and upper limit is 48 hours, preferably lower limit is 5 hours and upper limit is 16 hours.

In the synthesis of the compounds of the present invention, purification of a target compound from a reaction mixture is performed by methods usually used in the filed of organic chemistry, for example, a method comprising distribution and extraction of a reaction mixture between water and an arbitrarily organic solvent that is immiscible with water (e.g., benzene, toluene, ethyl acetate, butyl acetate, methyl isobutyl ketone, chloroform, dichloromethane and the like), followed by concentration, crystallization and the like. Further, as required, for example, fractionation purification by column chromatography using alumina, silica gel or the like may also be performed.

Typical methods for producing the compounds of the present invention are specifically explained in detail in the examples of the present specification. Therefore, those skilled in the art can prepare any compound falling within the scope of the general formula (I) based on explanations of the general preparation methods described above and examples described later by appropriately choosing starting compounds, reagents, reaction conditions and the like, and if necessary, applying appropriate modifications or alterations to the methods disclosed in the examples.

The compounds of the present invention may be in the form of a salt. The salt may be an acid addition salt such as salts with inorganic acids including hydrochloric acid, nitric acid, hydrobromic acid, and sulfuric acid, salts with aliphatic monocarboxylic acids, dicarboxylic acids, hydroxyalkanoic acids, hydroxydialkanoic acids, amino acids and the like, or salts deriving from non-toxic organic acids such as aromatic acids, aliphatic acids, and aromatic sulfonic acid. Examples of such acid addition salts include hydrochloride, hydrobromide, nitrate, sulfate, hydrogensulfate, hydrogenphosphate, dihydrogenphosphate, acetate, propionate, tartrate, oxalate, malonate, succinate, fumarate, maleate, mandelate, benzoate, phthalate, methanesulfonate, benzenesulfonate, toluenesulfonate, citrate, lactate, malate, glycolate, trifluoroacetate and the like.

As well as the compounds in free form or salts thereof, any hydrates and solvates thereof also fall within the scope of the present invention. The types of solvents that form the solvates are not particularly limited. Examples include solvents such as methanol, ethanol, acetone, and diethyl ether. However, the solvents are not limited to these examples.

The compounds of the present invention may have one or more asymmetric carbon atoms depending on the type of substituent, and any of stereoisomers such as optically active isomers or diastereoisomers in a pure form, any mixtures of the stereoisomers, racemates and the like also fall within the scope of the present invention.

The compounds of the present invention are characterized to have affinity for opioid δ receptor. Therefore, the compounds of the present invention are useful for preventive and/or therapeutic treatment of central nerve system diseases such as schizophrenia, depression, cerebral apoplexy, epilepsy, Alzheimer's disease, and Parkinson's disease and peripheral nerve system diseases such as pains, in which the opioid δ receptor is involved.

The medicaments provided by the present invention are characterized to comprise at least one kind of the compound represented by the general formula (I) or pharmacologically acceptable salt thereof as an active ingredient. The medicaments of the present invention can be administered to human or animals other than human by any of oral or parenteral routes (for example, intravenous injection, intramuscular injection, subcutaneous administration, rectal administration, percutaneous administration, intraspinal administration). As the medicaments of the present invention, the substances as active ingredients, per se, may be administered. It is generally preferable to prepare and administer a pharmaceutical composition, as a form suitable for the administration route, by using one or more kinds of additives for pharmaceutical preparations.

Specifically, examples of orally available formulations include tablets, capsules, powders, granules, syrups and the like. Examples of parenteral formulations include injections such as intravenous and intramuscular injections, formulations for rectal administration, oily suppositories, aqueous suppositories and the like.

These various pharmaceutical preparations can be prepared by using additives for pharmaceutical preparations which are ordinarily used, for example, excipients, disintegrating agents, binders, lubricants and coloring agents.

Examples of the excipients include lactose, glucose, cornstarch, sorbit, crystalline cellulose and the like. Examples of the disintegrating agents include starch, sodium alginate, gelatin powder, calcium carbonate, calcium citrate, dextrin and the like. Example of the binders include dimethylcellulose, polyvinyl alcohol, polyvinyl ether, methylcellulose, ethylcellulose, gum arabic, gelatin, hydroxypropylcellulose, polyvinylpyrrolidone and the like. Examples of the lubricants include talc, magnesium stearate, polyethylene glycor, hydrogenated vegetable oil and the like. Further, the pharmaceutical preparations can be prepared with addition of a buffer, pH modifier, stabilizer or the like as required.

Although content of the compound of the present invention in the pharmaceutical composition may vary depending on types of formulations. Generally, its lower limit is about 0.1% by weight and upper limit is 50% by weigh, preferably lower limit is 0.5% by weight and upper limit is 20% by weight based on the total composition. A dose may appropriately be determined depending on each case in consideration of the age, body weight, sex, type of a disease, severity of symptoms of a patient and the like. Generally, its lower limit is 1 mg and upper limit is 1000 mg, preferably its lower limit is 1 mg and upper limit is 300 mg, per day for an adult. The dose is administered once a day or several times a day dividedly.

EXAMPLES

The present invention will be explained more specifically with reference to the following examples and test example. However, the scope of the present invention is not limited to these examples.

Reference Example 1

1-Bromo-3-[2-(4-diethylcarbamoylbenzyl)phenoxy] propane (a) 4-Diethylcarbamoylbenzyl alcohol 4-Hydroxymethylbenzoic acid (10.0 g) was dissolved in N,N-dimethylformamide (200 ml), added with 1-hydroxybenzotriazole (9.766 g) and 1-ethyl-3-(3-dimethylaminopropyl)carbodiimide hydrochloride (WSC.HCl, 13.855 g) and stirred at room temperature for 1 hour. The reaction mixture was added with diethylamine (13.6 ml) and further stirred at room temperature for 1 hour. The reaction mixture was added with water (200 ml) and extracted twice with dichloromethane (200 ml). The organic layer was dried over anhydrous magnesium sulfate, and then the solvent was evaporated under reduced pressure. The residue was purified by silica gel column chromatography (elution solvent: hexane:ethyl acetate=1:2) to obtain 12.80 g of the title compound. Yield: 94%.

$^1$H-NMR (CDCl$_3$) δ (ppm); 1.09 (3H, br-s), 1.26 (3H, br-s), 3.25 (2H, br-s), 3.53 (2H, br-s), 4.66 (2H, s), 7.30 (4H, s)

MS (TSP); m/z 208 (MH$^+$)

(b) 4-Diethylcarbamoylbenzaldehyde

Oxalyl chloride (10.8 ml) was dissolved in dichloromethane (260 ml), added with dimethyl sulfoxide (17.5 ml) at −78° C. under an argon gas flow and stirred at the same temperature for 5 minutes. The reaction mixture was added with a solution of 4-diethylcarbamoylbenzyl alcohol (12.80 g) dissolved in dichloromethane (260 ml) at −78° C. and further stirred at the same temperature for 30 minutes. The reaction mixture was added with triethylamine (43.1 ml) at −78° C. and further stirred at room temperature for 30 minutes. After the reaction mixture was added with water (500 ml) and the layers were separated, the aqueous layer was extracted with dichloromethane (500 ml). The organic layer was dried over anhydrous magnesium sulfate, and then the solvent was evaporated under reduced pressure. The residue was purified by silica gel column chromatography (elution solvent: hexane:ethyl acetate=1:1) to obtain 12.075 g of the title compound. Yield: 95%.

$^1$H-NMR (CDCl$_3$) δ (ppm); 1.11 (3H, t, J=7 Hz), 1.27 (3H, t, J=7 Hz), 3.23 (2H, q, J=7 Hz), 3.56 (2H, q, J=7 Hz), 7.53 (2H, d, J=8 Hz), 7.93 (2H, d, J=8 Hz), 10.05 (1H, s)

MS (EI); m/z 205 (M$^+$)

(c) 1-(4-Diethylcarbamoylphenyl)-1-(2-methoxyphenyl)methyl alcohol

A solution of 2-bromoanisole (12.1 ml) dissolved in tetrahydrofuran (200 ml) was added with magnesium (2.368 g) and stirred at 60° C. for 1 hour to prepare a Grignard reagent. This Grignard reagent was added with a solution of 4-diethylcarbamoylbenzaldehyde (10.0 g) dissolved in tetrahydrofuran (200 ml) with ice cooling and stirred at room temperature for 1 hour. The reaction mixture was added with saturated aqueous ammonium chloride (400 ml) with ice cooling to quench the reaction and then extracted twice with dichloromethane (400 ml). The organic layer was dried over anhydrous magnesium sulfate, and then the solvent was evaporated under reduced pressure. The residue was purified by silica gel column chromatography (elution solvent: hexane:ethyl acetate=1:1) to obtain 14.14 g of the title compound. Yield: 93%.

$^1$H-NMR (CDCl$_3$) δ (ppm); 1.10 (3H, br-s), 1.23 (3H, br-s), 3.18 (1H, d, J=5 Hz), 3.26 (2H, br-s), 3.56 (2H, br-s), 3.81 (3H, s), 6.05 (1H, d, J=5 Hz), 6.85–7.00 (2H, m), 7.20–7.45 (6H, m)

MS (TSP); m/z 314 (MH$^+$)

(d) 2-(4-Diethylcarbamoylbenzyl)phenol 1-(4-Diethylcarbamoylphenyl)-1-(2-methoxyphenyl)methyl alcohol (14.14 g) was dissolved in pyridine (280 ml), added with acetic anhydride (140 ml) with ice cooling and stirred at room temperature for 15 hours. After the reaction mixture was added with methanol (140 ml) with ice cooling and stirred at room temperature for 10 minutes, the solvent was evaporated under reduced pressure to obtain 1-(4-diethylcarbamoylphenyl)-1-(2-methoxyphenyl)methyl acetate.

The obtained 1-(4-diethylcarbamoylphenyl)-1-(2-methoxyphenyl)methyl acetate was dissolved in methanol (280 ml), added with 10% palladium/carbon (7 g) and ammonium formate (28.44 g) under argon atmosphere and stirred at 60° C. for 2 hours. After insoluble matters were removed by filtration, the solvent was evaporated under reduced pressure to obtain 2-(4-diethylcarbamoylbenzyl)anisole.

The obtained 2-(4-diethylcarbamoylbenzyl)anisole was dissolved in dichloromethane (280 ml), added with boron tribromide (25.0 g) and stirred at room temperature for 3 hours. After the reaction mixture was slowly poured into ice (300 g) with ice cooling to quench the reaction and the layers were separated, the aqueous layer was extracted with dichloromethane (300 ml). The organic layer was dried over anhydrous magnesium sulfate, and then the solvent was evaporated under reduced pressure. The residue was purified by silica gel column chromatography (elution solvent: hexane:ethyl acetate=1:1) to obtain 10.15 g of the title compound. Yield: 79% (for the three steps).

$^1$H-NMR (CDCl$_3$) δ (ppm); 1.10 (3H, br-s), 1.23 (3H, br-s), 3.27 (2H, br-s), 3.53 (2H, br-s), 3.94 (2H, s), 6.70–6.80 (2H, m), 7.00–7.10 (2H, m), 7.15–7.30 (4H, m)

MS (TSP); m/z 284 (MH$^+$)

(e) 1-Bromo-3-[2-(4-diethylcarbamoylbenzyl) phenoxy]propane 2-(4-Diethylcarbamoylbenzyl)phenol (100 mg) was dissolved in tetrahydrofuran (2 ml), added with sodium hydride (60%, in oil, 21 mg) and stirred at 60° C. for 1.5 hours. The reaction mixture was added with 1,3-dibromopropane (0.18 ml) and stirred at the same temperature for 3 hours. After the reaction mixture was added with water (10 ml) and the layers were separated, the aqueous layer was extracted with dichloromethane (10 ml). The organic layer was dried over anhydrous magnesium sulfate, and then the solvent was evaporated under reduced pressure. The residue was purified by silica gel column chromatography (elution solvent: hexane:ethyl acetate=3:1) to obtain 99 mg of the title compound. Yield: 69%.

$^1$H-NMR (CDCl$_3$) δ (ppm); 1.12 (3H, br-s), 1.22 (3H, br-s), 2.25 (2H, m), 3.27 (2H, br-s), 3.44 (2H, t, J=6 Hz), 3.52 (2H, br-s), 3.98 (2H, s), 4.08 (2H, t, J=6 Hz), 6.84–7.29 (8H, m)

Reference Example 2

1-[2-(4-Diethylcarbamoylbenzyl)phenoxy]acetaldehyde (a) 1-[2-(4-Diethylcarbamoylbenzyl)phenoxy]-2,3-dihydroxypropane The 2-(4-diethylcarbamoylbenzyl)phenol (355 mg) obtained in Reference Example 1(d) was dissolved in a mixed solution of dioxane (3.6 ml) and water (3.6 ml), added with 1 N aqueous sodium hydroxide (63 μl) and glycidol (0.12 ml) and stirred at 90° C. for 18 hours. The reaction mixture was added with water (30 ml) and extracted twice with dichloromethane (30 ml). The organic layer was dried over anhydrous magnesium sulfate, and then the solvent was evaporated under reduced pressure. The residue was purified by silica gel column chromatography (elution solvent: ethyl acetate) to obtain 263 mg of the title compound. Yield: 59%.

$^1$H-NMR (CDCl$_3$) δ (ppm); 1.12 (3H, br-s), 1.24 (3H, br-s), 2.24 (1H, d, J=5 Hz), 2.66 (1H, t, J=5 Hz), 3.20–3.40 (4H, m), 3.53 (2H, br-s), 3.75–3.95 (3H, m), 3.99 (2H, s), 6.83 (1H, d, J=8 Hz), 6.95 (1H, t, J=8 Hz), 7.15–7.30 (6H, m)

MS (TSP); m/z 358 (MH$^+$)

(b) 1-[2-(4-Diethylcarbamoylbenzyl)phenoxy]acetaldehyde

1-[2-(4-Diethylcarbamoylbenzyl)phenoxy]-2,3-dihydroxypropane (263 mg) was dissolved in a mixed solution of dioxane (2.6 ml) and water (2.6 ml), added with sodium periodate (362 mg) and stirred at room temperature for 1 hour. The reaction mixture was added with water (10 ml) and extracted twice with dichloromethane (10 ml). The organic layer was dried over anhydrous magnesium sulfate, and then the solvent was evaporated under reduced pressure to obtain 239 mg of the title compound. Yield: 100%.

$^1$H-NMR (CDCl$_3$) δ (ppm); 1.11 (3H, br-s), 1.22 (3H, br-s), 3.27 (2H, br-s), 3.53 (2H, br-s), 4.07 (2H, s), 4.53 (2H, s), 6.71 (1H, d, J=8 Hz), 6.97 (1H, t, J=8 Hz), 7.14–7.29 (6H, m), 9.77 (1H, s)

Reference Example 3

3-Benzyl-1-phenyl-1,3,8-triazaspiro[4,5]decan-4-one trifluoroacetate (a) 8-(tert-Butoxycarbonyl)-1-phenyl-1,3,8-triazaspiro[4,5]decan-4-one 1-Phenyl-1,3,8-triazaspiro[4,5]decan-4-one (2.00 g) was dissolved in a mixed solution of dichloromethane (20 ml) and methanol (20 ml), added with di-tert-butyl dicarbonate (2.98 ml) and diisopropylethylamine (2.26 ml) and stirred at room temperature for 14 hours. The solvent was evaporated under reduced pressure, and then the residue was added with water (50 ml) and extracted twice with dichloromethane (50 ml). The organic layer was dried over anhydrous magnesium sulfate, and then the solvent was evaporated under reduced pressure. The residue was purified by silica gel column chromatography (elution solvent: hexane:ethyl acetate=1:1) to obtain 2.173 g of the title compound. Yield: 76%.

$^1$H-NMR (CDCl$_3$) δ (ppm); 1.51 (9H, s), 1.69 (2H, d, J=14 Hz), 2.56 (2H, br-s), 3.54 (2H, br-s), 4.05 (2H, br-s), 4.76 (2H, s), 6.70–6.90 (4H, m), 7.20–7.30 (2H, m)

MS (TSP); m/z 332 (MH$^+$)

(b) 3-Benzyl-8-(tert-butoxycarbonyl)-1-phenyl-1,3,8-triazaspiro[4,5]decan-4-one 8-(tert-Butoxycarbonyl)-1-phenyl-1,3,8-triazaspiro[4,5]decan-4-one (1.441 g) was dissolved in N,N-dimethylformamide (28 ml), added with sodium hydride (60%, in oil, 521 mg) and stirred at room temperature for 1.5 hours. The reaction mixture was added with benzyl bromide (1.81 ml) with ice cooling and further stirred at room temperature for 1 hour. The reaction mixture was added with water (50 ml) and extracted twice with dichloromethane (70 ml). The organic layer was dried over anhydrous magnesium sulfate, and then the solvent was evaporated under reduced pressure. The residue was purified by silica gel column chromatography (elution solvent: hexane:ethyl acetate=5:1 →4:1) to obtain 1.710 g of the title compound. Yield: 94%.

$^1$H-NMR (CDCl$_3$) δ (ppm); 1.51 (9H, s), 1.65 (2H, d, J=14 Hz), 2.58 (2H, br-s), 3.62 (2H, br-s), 4.05 (2H, br-s), 4.56 (2H, s), 4.61 (2H, s), 6.67 (1H, d, J=7 Hz), 6.81 (1H, t, J=7 Hz), 7.15–7.40 (8H, m)

MS (EI); m/z 421 (M$^+$)

(c) 3-Benzyl-1-phenyl-1,3,8-triazaspiro[4,5]decan-4-one trifluoroacetate

3-Benzyl-8-(tert-butoxycarbonyl)-1-phenyl-1,3,8-triazaspiro[4,5]decan-4-one (1.671 g) was added with trifluoroacetic acid (32 ml) with ice cooling and stirred at the same temperature for 1 hour. The solvent was evaporated under reduced pressure and then the residue was added with diisopropyl ether (50 ml) to precipitate the product. The precipitates was collected by filtration and dried to obtain 1.561 g of the title compound. Yield: 91%.

$^1$H-NMR (CDCl$_3$) δ (ppm); 1.86 (2H, d, J=14 Hz), 3.04 (2H, dt, J=5 Hz, 14 Hz), 3.43 (2H, d, J=12 Hz), 3.96 (2H, q, J=12 Hz), 4.61 (2H, s), 4.62 (2H, s), 6.80–6.90 (7.20–7.45 (8H, m)

MS (EI); m/z 321 (M$^+$)

Reference Example 4

4-(1,2,3,4-Tetrahydroquinolin-1-yl)piperidine trifluoroacetate (a) 1-(tert-Butoxycarbonyl)-4-(1,2,3,4-tetrahydroquinolin-1-yl)piperidine 1-(tert-Butoxycarbonyl)-4-piperidone (800 mg) was dissolved in dichloroethane (16 ml), added with 1,2,3,4-tetrahydroquinoline (0.50 ml), sodium triacetoxyborohydride (1.7 g) and acetic acid (2.3 ml) and stirred at room temperature for 24 hours. The reaction mixture was added with saturated aqueous sodium hydrogencarbonate (20 ml) and extracted twice with ethyl acetate (20 ml). The organic layer was dried over anhydrous magnesium sulfate, and then the solvent was evaporated under reduced pressure. The residue was purified by preparative thin layer silica gel column chromatography (developing solvent: hexane:ethyl acetate=10:1) to obtain 90.6 mg of the title compound. Yield: 7%.

¹H-NMR (CDCl₃) δ (ppm); 1.48 (9H, s), 1.70 (4H, m), 1.90 (2H, m), 2.73 (2H, t, J=7 Hz), 2.79 (2H, m), 3.16 (2H, t, J=7 Hz), 3.75 (1H, m), 4.25 (2H, m), 6.57 (1H, t, J=8 Hz), 6.66 (1H, d, J=8 Hz), 6.96 (1H, d, J=8 Hz), 7.05 (1H, t, J=8 Hz)

(b) 4-(1,2,3,4-Tetrahydroquinolin-1-yl)piperidine trifluoroacetate

The title compound was obtained in the same manner in Reference Example 3(c) from 1-(tert-butoxycarbonyl)-4-(1, 2,3,4-tetrahydroquinolin-1-yl)piperidine. Yield: 100%.

¹H-NMR (CDCl₃) δ (ppm); 1.65 (2H, m), 2.07 (2H, m), 2.17 (2H, m), 2.95 (2H, t, J=7 Hz), 3.15 (2H, m), 3.52 (2H, t, J=7 Hz), 3.58 (2H, m), 3.96 (1H, m), 7.25 (4H, m)

MS (TSP); m/z 217 (MH⁺)

Reference Example 5

1-[2-(4-Diethylcarbamoylphenyl)phenoxy]acetaldehyde (a) 4-Diethylcarbamoyl-1-iodobenzene The title compound was obtained in the same manner in Reference Example 1(a) from 4-iodobenzoic acid. Yield: 92%.

¹H-NMR (CDCl₃) δ (ppm); 1.11 (3H, br-s), 1.23 (3H, br-s), 3.24 (2H, br-s), 3.52 (2H, br-s), 7.12 (2H, d, J=8 Hz), 7.74 (2H, d, J=8 Hz)

MS (FAB); m/z 304 (MH⁺)

(b) 2-(4-Diethylcarbamoylphenyl)anisole

A solution of 2-bromoanisole (0.25 ml) dissolved in tetrahydrofuran (5 ml) was added with magnesium (48.6 mg) and stirred at 60° C. for 1 hour to prepare a Grignard reagent. This solution was cooled to −78° C., added with a solution of tributyl borate (0.65 ml) dissolved in tetrahydrofuran (5 ml) and gradually warmed to room temperature with stirring for 20 hours. The reaction mixture was added with saturated aqueous ammonium chloride (10 ml) with ice cooling, stirred for 10 minutes and then extracted twice with ether (10 ml). The organic layer was dried over anhydrous magnesium sulfate, and then the solvent was evaporated under reduced pressure to obtain (2-methoxyphenyl)boric acid.

4-Diethylcarbamoyl-1-iodobenzene (100 mg) was dissolved in dimethoxyethane (1 ml), added with tetrakis(triphenylphosphine)palladium (19.1 mg) under argon atmosphere, and stirred at room temperature for 10 minutes. The reaction mixture was added with the solution of (2-methoxyphenyl)boric acid (100 mg) dissolved in toluene (0.5 ml) prepared above and a solution of sodium carbonate (105 mg) dissolved in water (0.5 ml) and stirred at 90° C. for 5.5 hours. The reaction mixture was added with water (2 ml) and extracted twice with dichloromethane (4 ml). The organic layer was dried over anhydrous magnesium sulfate, and then the solvent was evaporated under reduced pressure. The residue was purified by silica gel column chromatography (elution solvent: hexane:ethyl acetate=3:1) to obtain 81.9 mg of the title compound. Yield: 88%.

¹H-NMR (CDCl₃) δ (ppm); 1.23 (6H, br-s), 3.36 (2H, br-s), 3.56 (2H, br-s), 3.82 (3H, s), 6.95–7.05 (2H, m), 7.32 (2H, d, J=8 Hz), 7.41 (2H, d, J=8 Hz), 7.56 (2H, d, J=8 Hz)

MS (FAB); m/z 284 (MH⁺)

(c) 2-(4-Diethylcarbamoylphenyl)phenol 2-(4-Diethylcarbamoylphenyl)anisole (250 mg) was dissolved in dichloromethane (10 ml), added with boron tribromide (0.42 ml) and stirred at room temperature for 3 hours. After the reaction mixture was slowly poured into ice (20 g) with ice cooling to quench the reaction and the layers were separated, the aqueous layer was extracted with dichloromethane (10 ml). The organic layer was dried over anhydrous magnesium sulfate, and then the solvent was evaporated under reduced pressure. The residue was purified by silica gel column chromatography (elution solvent: hexane:ethyl acetate=2:1→1:1) to obtain 231 mg of the title compound. Yield: 97%.

¹H-NMR (CDCl₃) δ (ppm); 1.18 (3H, br-s), 1.26 (3H, br-s), 3.34 (2H, br-s), 3.57 (2H, br-s), 7.00 (2H, t, J=8 Hz), 7.26 (2H, m), 7.50 (4H, m)

MS (TSP); m/z 270 (MH⁺)

(d) 1-[2-(4-Diethylcarbamoylphenyl)phenoxy]-2,3-dihydroxypropane

The title compound was obtained in the same manner in Reference Example 2(a) from 2-(4-diethylcarbamoylphenyl)phenol. Yield: 87%.

¹H-NMR (CDCl₃) δ (ppm); 1.17 (3H, br-s), 1.26 (3H, br-s), 3.32 (2H, br-s), 3.50–3.75 (4H, m), 3.90–4.10 (3H, m), 6.95–7.10 (2H, m), 7.35 (2H, m), 7.42 (2H, d, J=8 Hz), 7.51 (2H, d, J=8 Hz)

MS (TSP); m/z 344 (MH⁺)

(e) 1-[2-(4-Diethylcarbamoylphenyl)phenoxy]acetaldehyde

The title compound was obtained in the same manner in Reference Example 2 (b) from 1-[2-(4-diethylcarbamoylphenyl)phenoxy]-2,3-dihydroxypropane. Yield: 100%.

¹H-NMR (CDCl₃) δ (ppm); 1.17 (3H, br-s), 1.26 (3H, br-s), 3.34 (2H, br-s), 3.57 (2H, br-s), 4.53 (2H, s), 6.95–7.10 (2H, m), 7.35–7.45 (4H, m), 7.51 (2H, d, J=8 Hz), 9.77 (1H, s)

Reference Example 6

4-(1H-Benzimidazol-1-yl)piperidine trifluoroacetate (a) 1-(tert-Butoxycarbonyl)-4-hydroxypiperidine 4-Hydroxypiperidine hydrochloride (3 g) was dissolved in dioxane (30 ml), added with di-tert-butyl dicarbonate (5.2 g) and stirred at room temperature for 10 minutes. The reaction mixture was added with 8% aqueous sodium hydrogencarbonate (60 ml) and further stirred for 3.5 hours. Dioxane was evaporated under reduced pressure, and the aqueous layer was extracted with ethyl acetate (60 ml). The organic layer was dried over anhydrous magnesium sulfate, and then the solvent was evaporated under reduced pressure. The residue was purified to obtain 4.81 g of the title compound. Yield: 100%.

¹H-NMR (CDCl₃) δ (ppm); 1.46 (11H, m), 1.86 (2H, m), 3.04 (2H, m), 3.85 (3H, m)

(b) 1-(tert-Butoxycarbonyl)-4-(p-toluenesulfonyloxy)piperidine 1-(tert-Butoxycarbonyl)-4-hydroxypiperidine (4.81 g) was dissolved in pyridine (48 ml), added with p-toluenesulfonyl chloride (9.0 g) and triethylamine (6.7 ml) and stirred at room temperature for 17 hours. The reaction mixture was added with cold water (500 ml) and stirred for 2 hours, and then the produced crystals were collected by filtration. These crystals were purified by silica gel column chromatography (elution solvent: hexane:ethyl acetate=3:1) to obtain 6.49 g of the title compound. Yield: 76%.

$^1$H-NMR (CDCl$_3$) δ (ppm); 1.43 (9H, s), 1.59 (2H, m), 1.70 (2H, m), 2.45 (3H, s), 3.25 (2H, m), 3.57 (2H, m), 4.67 (1H, m), 7.34 (2H, d, J=8 Hz), 7.79 (2H, d, J=8 Hz)

(c) 1-(tert-Butoxycarbonyl)-4-(1H-benzimidazol-1-yl)piperidine

1H-Benzimidazole (300 mg) was dissolved in N,N-dimethylformamide (6 ml), added with sodium hydride (60%, in oil, 122 mg) and stirred at room temperature for 1 hour. Subsequently, the reaction mixture was added with 1-(tert-butoxycarbonyl)-4-(p-toluenesulfonyloxy)piperidine (1.08 g) and further stirred at room temperature for 23 hours and at 60° C. for 2 hours. The reaction mixture was added with water (10 ml) and extracted twice with ethyl acetate (10 ml). The organic layer was dried over anhydrous magnesium sulfate, and then the solvent was evaporated under reduced pressure. The residue was purified by silica gel column chromatography (elution solvent: ethyl acetate) to obtain 192 mg of the title compound. Yield: 25%.

$^1$H-NMR (CDCl$_3$) δ (ppm); 1.51 (9H, s), 2.03 (2H, m), 2.18 (2H, m), 2.94 (2H, m), 4.36 (3H, m), 7.30 (2H, m), 7.43 (1H, m), 7.82 (1H, m), 7.98 (1H, s)

MS (TSP); m/z 302 (MH$^+$)

(d) 4-(1H-Benzimidazol-1-yl)piperidine trifluoroacetate

The title compound was obtained in the same manner in Reference Example 3(c) from 1-(tert-butoxycarbonyl)-4-(1H-benzimidazol-1-yl)piperidine. Yield: 100%.

$^1$H-NMR (D$_2$O) δ (ppm); 2.25 (2H, m), 2.48 (2H, m), 3.22 (2H, m), 3.59 (2H, m), 4.96 (1H, m), 7.54 (2H, m), 7.72 (1H, m), 7.80 (1H, m), 9.21 (1H, s)

Reference Example 7

4-(1,2,3,4-Tetrahydroquinazolin-2-on-1-yl)piperidine trifluoroacetate

(a) 1-(tert-Butoxycarbonyl)-4-[(2-hydroxymethylphenyl)amino]piperidine

The title compound was obtained in the same manner in Reference Example 4(a) from 2-aminobenzyl alcohol and 1-(tert-butoxycarbonyl)-4-piperidone. Yield: 68%.

$^1$H-NMR (CDCl$_3$) δ (ppm); 1.47 (2H, m), 1.50 (9H, s), 2.01 (2H, m), 3.00 (2H, m), 3.50 (1H, m), 3.99 (2H, m), 4.67 (2H, s), 6.66 (2H, m), 7.05 (1H, d, J=8 Hz), 7.21 (1H, t, J=8 Hz)

(b) 1-(tert-Butoxycarbonyl)-4-(1,2,3,4-tetrahydroquinazolin-2-on-1-yl)piperidine 1-(tert-Butoxycarbonyl)-4-[(2-hydroxymethylphenyl)amino]piperidine (716 mg) was dissolved in tetrahydrofuran (7 ml), added with phthalimide (349 mg), triphenylphosphine (736 mg) and diethyl azodicarboxylate (0.43 ml) and stirred at room temperature for 21 hours. The reaction mixture was added with water (10 ml) and extracted twice with dichloromethane (10 ml). The organic layer was dried over anhydrous magnesium sulfate, and then the solvent was evaporated under reduced pressure. The residue was purified by silica gel column chromatography (elution solvent: hexane:ethyl acetate=4:1) to obtain crude 1-(tert-butoxycarbonyl)-4-[(2-phthalimidylmethylphenyl)amino]piperidine (420 mg).

Subsequently, the resulting crude 1-(tert-butoxycarbonyl)-4-[(2-phthalimidylmethylphenyl)amino]piperidine (420 mg) was dissolved in ethanol (8 ml), added with hydrazine monohydrate (0.23 ml) and stirred at room temperature for 1 hour and at 40° C. for 1 hour. After insoluble matters were removed by filtration from the reaction mixture, the solvent was evaporated under reduced pressure. The residue was added with water (10 ml) and extracted twice with dichloromethane (10 ml). The solvent was evaporated under reduced pressure to obtain 219 mg of 1-(tert-butoxycarbonyl)-4-[(2-aminomethylphenyl)amino]piperidine.

The obtained 1-(tert-butoxycarbonyl)-4-[(2-aminomethylphenyl)amino]-piperidine (219 mg) was dissolved in toluene (5 ml), added with 1,1'-carbonyldiimidazole (128 mg) and stirred at 100° C. for 1.5 hours. The reaction mixture was added with water (10 ml) and extracted twice with ethyl acetate (10 ml). The organic layer was dried over anhydrous magnesium sulfate, and then the solvent was evaporated under reduced pressure. The residue was purified by silica gel column chromatography (elution solvent: hexane:ethyl acetate=1:2→1:3) to obtain 130 mg of the title compound. Yield: 17% (for the three steps).

$^1$H-NMR (CDCl$_3$) δ (ppm); 1.49 (11H, m), 1.79 (2H, m), 2.60 (2H, m), 2.80 (2H, m), 4.14 (1H, m), 4.24 (2H, s), 5.24 (1H, br-s), 7.04 (3H, m), 7.24 (1H, m)

MS (TSP); m/z 332 (MH$^+$)

(c) 4-(1,2,3,4-Tetrahydroquinazolin-2-on-1-yl)piperidine trifluoroacetate

The title compound was obtained in the same manner in Reference Example 3(c) from 1-(tert-butoxycarbonyl)-4-(1,2,3,4-tetrahydroquinazolin-2-on-1-yl)piperidine. Yield: 100%.

$^1$H-NMR (DMSO-d$_6$) δ (ppm); 1.86 (2H, m), 2.79 (2H, m), 3.06 (2H, m), 3.35 (2H, m), 4.11 (3H, m), 6.97 (1H, t, J=8 Hz), 7.17 (2H, d, J=8 Hz), 7.24 (1H, d, J=8 Hz)

MS (FAB); m/z 232 (MH$^+$)

Reference Example 8

4-Phenylpiperidine hydrochloride 1,2,3,6-Tetrahydro-4-phenylpyridine hydrochloride (70 mg) was dissolved in methanol (1.4 ml), added with 10% palladium/carbon (35 mg) and stirred at 45° C. for 5 hours under hydrogen gas atmosphere. After insoluble matters were removed by filtration, the solvent was evaporated under reduced pressure to obtain 70.0 mg of the title compound. Yield: 99%.

$^1$H-NMR(CD$_3$OD) δ (ppm); 1.93 (2H, m), 2.06 (2H, m), 2.89 (1H, m), 3.13 (2H, m) 3.49 (2H, m), 7.20–7.34 (5H, m)

MS (EI); m/z 161 (M$^+$)

Reference Example 9

Spiro[3H-indole-3,4'-piperidin]-2(1H)-one hydrochloride

(a) 3-[2-[N-Benzyl-N-(2-hydroxyethyl)amino]ethyl]-2,3-dihydro-1H-indol-2-one The title compound was obtained in the same manner in Reference Example 4(a) from N-benzylethanolamine and 3-formylmethyl-2,3-dihydro-1H-indol-2-one synthesized in accordance with the descriptions of WO98/08816. Yield: 79%.

$^1$H-NMR (CDCl$_3$) δ (ppm); 2.19 (2H, m), 2.50–2.80 (4H, m), 2.97 (1H, br-s), 3.50–3.65 (5H, m), 6.80–7.05 (3H, m), 7.10–7.30 (6H, m), 8.98 (1H, s)

MS (EI); m/z 310 (M$^+$)

(b) 3-[2-[N-(Benzyloxycarbonyl)-N-(2-hydroxyethyl)amino]ethyl]-2,3-dihydro-1H-indol-2-one 3-[2-[N-Benzyl-N-(2-hydroxyethyl)amino]ethyl]-2,3-dihydro-1H-indol-2-one (463 mg) was dissolved in dichloromethane (9.2 ml), added with benzyl chloroformate (0.51 ml) and potassium hydrogencarbonate (358 mg) and stirred at room temperature for 24 hours. The reaction mixture was added with water (10 ml) and extracted twice with dichloromethane (10 ml). The organic layer was dried over anhydrous magnesium sulfate, and then the solvent was evaporated under reduced pressure. The residue was dissolved in methanol (10 ml), added with 1 N aqueous sodium hydroxide (2.2 ml) and stirred for 30 minutes. The reaction mixture was added with water (50 ml) and extracted twice with dichloromethane (40 ml). The organic layer was dried over anhydrous magnesium sulfate, and then the solvent was evaporated under reduced pressure. The residue was purified by silica gel column chromatography (elution solvent: ethyl acetate) to obtain 272 mg of the title compound. Yield: 52%.

$^1$H-NMR (CDCl$_3$) δ (ppm); 2.25 (2H, m), 2, 85 (1H, m), 3.49 (4H, m), 3.77 (2H, m), 5.05 (1H, d, J=12 Hz), 5.12 (1H, d, J=12 Hz), 6.81 (1H, d, J=8 Hz), 6.90–7.10 (2H, m), 7.19 (1H, t, J=8 Hz), 7.34 (5H, m), 7.60–7.80 (1H, m)

MS (TSP); m/z 355 (MH$^+$)

(c) 3-[2-[N-(Benzyloxycarbonyl)-N-(2-methanesulfonyloxyethyl)amino]ethyl]-2,3-dihydro-1H-indol-2-one 3-[2-[N-(Benzyloxycarbonyl)-N-(2-hydroxyethyl)amino]ethyl]-2,3-dihydro-1H-indol-2-one (256 mg) was dissolved in dichloromethane (5 ml), added with triethylamine (0.20 ml) and methanesulfonyl chloride (0.11 ml) with ice cooling and stirred at room temperature for 1.5 hours. The reaction mixture was added with water (5 ml) and extracted twice with dichloromethane (5 ml). The organic layer was dried over anhydrous magnesium sulfate, and then the solvent was evaporated under reduced pressure. The residue was purified by silica gel column chromatography (elution solvent: hexane:ethyl acetate=1:2) to obtain 158 mg of the title compound. Yield: 51%.

$^1$H-NMR (CDCl$_3$) δ (ppm); 2.23 (2H, m), 2.85–3.00 (3H, m), 3.30–3.70 (5H, m), 4.20–4.40 (2H, m), 5.07 (1H, d, J=12 Hz), 5.14 (1H, d, J=12 Hz), 6.85 (1H, d, J=8 Hz), 6.92 (1H, m), 7.13 (1H, m), 7.20 (1H, t, J=8 Hz), 7.35 (5H, m), 7.80–7.95 (1H, m)

MS (FAB); m/z 433 (MH$^+$)

(d) 1'-(Benzyloxycarbonyl)spiro[3H-indole-3,4'-piperidin]-2(1H)-one

3-[2-[N-(Benzyloxycarbonyl)-N-(2-methanesulfonyloxyethyl)amino]ethyl]-2,3-dihydro-1H-indol-2-one (158 mg) was dissolved in N,N-dimethylformamide (3 ml), added with sodium hydride (60%, in oil, 29.2 mg) and stirred at room temperature for 1.5 hours. The reaction mixture was added with water (10 ml) and extracted twice with dichloromethane (10 ml). The organic layer was dried over anhydrous magnesium sulfate, and then the solvent was evaporated under reduced pressure. The residue was purified by silica gel column chromatography (elution solvent: hexane:ethyl acetate=2:1) to obtain 74.6 mg of the title compound. Yield: 61%.

$^1$H-NMR (CDCl$_3$) δ (ppm); 1.58 (4H, m), 3.90 (4H, m), 5.19 (2H, s), 6.89 (1H, d, J=8 Hz), 7.05 (1H, t, J=8 Hz), 7.23 (1H, t, J=8 Hz), 7.30–7.40 (6H, m), 7.56 (1H, s)

MS (FAB); m/z 337 (MH$^+$)

(e) Spiro[3H-indole-3,4'-piperidin]-2(1H)-one hydrochloride

1'-(Benzyloxycarbonyl)spiro[3H-indole-3,4'-piperidine]-2(1H)-one (74.6 mg) was dissolved in methanol (1.5 ml), added with 10% palladium/carbon (14 mg) and stirred at room temperature for 4 hours under hydrogen gas atmosphere. After insoluble matters were removed by filtration, the reaction mixture was added with 1 N aqueous hydrochloric acid (0.33 ml), and the solvent was evaporated under reduced pressure to obtain 51.7 mg of the title compound. Yield: 98%.

$^1$H-NMR (D$_2$O) δ (ppm); 2.11 (4H, m), 3.48 (2H, m), 3.72 (2H, m), 7.07 (1H, d, J=8 Hz), 7.18 (1H, t, J=8 Hz), 7.35 (1H, t, J=8 Hz), 7.45 (1H, d, J=8 Hz)

MS (TSP); m/z 203 (MH$^+$)

Reference Example 10

4-(3,4-Dihydro-2H-1,4-benzoxazin-3-on-4-yl)piperidine trifluoroacetate (a) 1-(tert-Butoxycarbonyl)-4-[(2-hydroxyphenyl)amino]piperidine The title compound was obtained in the same manner in Reference Example 4(a) from 1-(tert-butoxycarbonyl)-4-piperidone and 2-aminophenol. Yield: 100%.

$^1$H-NMR (CDCl$_3$) δ (ppm); 1.37 (2H, m), 1.47 (9H, s), 2.00 (2H, m), 2.91 (2H, m), 3.36 (1H, m), 4.04 (2H, m), 6.66 (1H, t, J=8 Hz), 6.74 (2H, m), 6.83 (1H, t, J=8 Hz)

(b) 1-(tert-Butoxycarbonyl)-4-[(2-methoxycarbonylmethoxyphenyl)amino]piperidine 1-(tert-Butoxycarbonyl)-4-[(2-hydroxyphenyl)amino]piperidine (50 mg) was dissolved in N,N-dimethylformamide (1 ml), added with methyl bromoacetate (17 μl) and potassium carbonate (25 mg) and stirred at room temperature for 17 hours. The reaction mixture was added with water (3 ml) and extracted twice with ethyl acetate (3 ml). The organic layer was dried over anhydrous magnesium sulfate, and then the solvent was evaporated under reduced pressure. The residue was purified by preparative thin layer silica gel column chromatography (developing solvent: hexane:ethyl acetate=1:1) to obtain 51.8 mg of the title compound. Yield: 83%.

$^1$H-NMR (CDCl$_3$) δ (ppm); 1.44 (2H, m), 1.47 (9H, s), 2.04 (2H, m), 2.97 (2H, m), 3.44 (1H, m), 3.80 (3H, s), 4.02 (2H, m), 4.64 (2H, s), 6.63 (2H, m), 6.71 (1H, d, J=8 Hz), 6.91 (1H, t, J=8 Hz)

MS (TSP); m/z 365 (MH$^+$)

(c) 1-(tert-Butoxycarbonyl)-4-[(2-carboxymethoxyphenyl)amino]piperidine 1-(tert-Butoxycarbonyl)-4-[(2-methoxycarbonylmethoxyphenyl)amino]piperidine (100 mg) was dissolved in methanol (1 ml), added with 1 N aqueous sodium hydroxide (0.55 ml) and stirred at room temperature for 1 hour. The reaction mixture was neutralized with 1 N aqueous hydrochloric acid and extracted twice with ethyl acetate (3 ml). The organic layer was dried over anhydrous magnesium sulfate, and then the solvent was evaporated under reduced pressure to obtain 72.1 mg of the title compound. Yield: 75%.

$^1$H-NMR (CDCl$_3$) δ (ppm); 1.46 (9H, s), 1.50 (2H, m), 1.97 (2H, m), 2.84 (2H, m), 3.42 (1H, m), 4.05 (2H, m), 4.62 (2H, s), 6.95 (4H, m)

(d) 1-(tert-Butoxycarbonyl)-4-(3,4-dihydro-2H-1,4-benzoxazin-3-on-4-yl)piperidine 1-(tert-Butoxycarbonyl)-4-[(2-carboxymethoxyphenyl)amino]piperidine (351 mg) was dissolved in dichloroethane (7 ml), added with thionyl chloride (73 μl) and stirred at room temperature for 1.5 hours. The reaction mixture was added with triethylamine (0.28 ml) and further stirred at 40° C. for 2 hours. The reaction mixture was added with water (10 ml) and extracted twice with ethyl acetate (10 ml). The organic layer was dried over anhydrous magnesium sulfate, and then the solvent was evaporated under reduced pressure. The residue was purified by silica gel column chromatography (elution solvent: hexane:ethyl acetate=2:1) to obtain 191 mg of the title compound. Yield: 57%.

$^1$H-NMR (CDCl$_3$) δ (ppm); 1.49 (9H, s), 1.76 (2H, m), 2.54 (2H, m), 2.80 (2H, m), 4.31 (2H, m), 4.40 (1H, m), 4.50 (2H, s), 7.02 (3H, m), 7.13 (1H, m)

MS (TSP); m/z 333 (MH$^+$)

(e) 4-(3,4-Dihydro-2H-1,4-benzoxazin-3-on-4-yl)piperidine trifluoroacetate

The title compound was obtained in the same manner in Reference Example 3(c) from 1-(tert-butoxycarbonyl)-4-(3,4-dihydro-2H-1,4-benzoxazin-3-on-4-yl)piperidine. Yield: 73%.

$^1$H-NMR (DMSO-d$_6$) δ (ppm); 1.89 (2H, m), 2.74 (2H, m), 3.06 (2H, m), 3.38 (2H, m), 4.33 (1H, m), 4.58 (2H, s), 7.06 (3H, m), 7.42 (1H, d, J=8 Hz)

Reference Example 11

4-(1,3-Dihydro-7-methyl-2H-benzimidazol-2-on-1-yl)piperidine hydrobromate (a) 1-Benzyl-4-[(2-methyl-6-nitrophenyl)amino]piperidine 4-Amino-1-benzylpiperidine (0.20 ml) was dissolved in dimethyl sulfoxide (0.2 ml), added with 2-chloro-3-nitrotoluene (0.13 ml) and stirred at 100° C. for 19 hours. The reaction mixture was added with water (2 ml) and extracted twice with ethyl acetate (2 ml). The organic layer was dried over anhydrous magnesium sulfate, and then the solvent was evaporated under reduced pressure. The residue was purified by silica gel column chromatography (elution solvent: hexane:ethyl acetate=3:1) to obtain 51.1 mg of the title compound. Yield: 16%.

$^1$H-NMR (CDCl$_3$) δ (ppm); 1.51 (2H, m), 1.85 (2H, m), 2.07 (2H, m), 2.35 (3H, s), 2.77 (2H, m), 3.28 (1H, m), 3.48 (2H, s), 6.82 (1H, t, J=8 Hz), 7.22–7.31 (6H, m), 7.90 (1H, d, J=8 Hz)

MS (TSP, negative); m/z 325 (M$^-$)

(b) 1-Ethoxycarbonyl-4-[(2-methyl-6-nitrophenyl)amino]piperidine

1-Benzyl-4-[(2-methyl-6-nitrophenyl)amino]piperidine (45.2 mg) was dissolved in dichloromethane (0.9 ml), added with ethyl chloroformate (27 μl) and potassium hydrogen-carbonate (28 mg) and stirred at room temperature for 30 minutes. The reaction mixture was added with water (2 ml) and extracted twice with ethyl acetate (2 ml). The organic layer was dried over anhydrous magnesium sulfate, and then the solvent was evaporated under reduced pressure. The residue was purified by preparative thin layer silica gel column chromatography (developing solvent: hexane:ethyl acetate=2:1) to obtain 38.3 mg of the title compound. Yield: 90%.

$^1$H-NMR (CDCl$_3$) δ (ppm); 1.25 (3H, t, J=7 Hz), 1.38 (2H, m), 1.87 (2H, m), 2.38 (3H, s), 2.87 (2H, m), 3.37 (1H, m), 4.04 (2H, m), 4.13 (2H, q, J=7 Hz), 6.54 (1H, d, J=9 Hz), 6.88 (1H, t, J=8 Hz), 7.35 (1H, d, J=8 Hz), 7.91 (1H, d, J=8 Hz)

(c) 4-[(2-Amino-6-methylphenyl)amino]-1-ethoxycarbonylpiperidine

1-Ethoxycarbonyl-4-[(2-methyl-6-nitrophenyl)amino]piperidine (38 mg) was dissolved in tetrahydrofuran (0.4 ml), added with a suspension of Raney nickel in ethanol (0.2 ml) and stirred at 40° C. for 2 hours under hydrogen gas atmosphere. After insoluble matters were removed, the solvent was evaporated under reduced pressure. The residue was purified by preparative thin layer silica gel column chromatography (developing solvent: hexane:ethyl acetate=2:1) to obtain (28.6 mg) of the title compound. Yield: 83%.

$^1$H-NMR (CDCl$_3$) δ (ppm); 1.26 (3H, t, J=7 Hz), 1.35 (2H, m), 1.90 (2H, m), 2.22 (3H, s), 2.76 (2H, m), 3.13 (1H, m), 4.12 (2H, q, J=7 Hz), 4.18 (2H, m), 6.60 (2H, m), 6.80 (1H, t, J=8 Hz)

MS (FAB); m/z 277 (MH$^+$)

(d) 1-Ethoxycarbonyl-4-(1,3-dihydro-7-methyl-2H-benzimidazol-2-on-1-yl)piperidine 4-[(2-Amino-6-methylphenyl)amino]-1-ethoxycarbonylpiperidine (75.2 mg) was dissolved in dichloromethane (1.5 ml), added with triphosgene (80.5 mg) and triethylamine (76 μl) and stirred at room temperature for 2 hours. The reaction mixture was added with water (5 ml) and extracted twice with ethyl acetate (5 ml). The organic layer was dried over anhydrous magnesium sulfate, and then the solvent was evaporated under reduced pressure. The residue was purified by preparative thin layer silica gel column chromatography (developing solvent: hexane:ethyl acetate=1:1) to obtain 59.1 mg of the title compound. Yield: 72%.

$^1$H-NMR (CDCl$_3$) δ (ppm); 1.29 (3H, t, J=7 Hz), 1.84 (2H, m), 2.60 (3H, s), 2.78 (4H, m), 4.17 (2H, q, J=7 Hz), 4.38 (2H, m), 4.52 (1H, m), 6.81 (1H, t, J=5 Hz), 6.95 (2H, d, J=5 Hz)

MS (TSP); m/z 304 (MH$^+$)

(e) 4-(1,3-Dihydro-7-methyl-2H-benzimidazol-2-on-1-yl)piperidine hydrobromide

1-Ethoxycarbonyl-4-(1,3-dihydro-7-methyl-2H-benzimidazol-2-on-1-yl)piperidine (59 mg) was dissolved in 48% hydrobromic acid (0.3 ml) and stirred at 100° C. for 1 hour. The reaction mixture was added with ethanol, and the produced crystals were collected by filtration to obtain 26.8 mg of the title compound. Yield: 44%.

$^1$H-NMR (DMSO-d$_6$) δ (ppm); 1.95 (2H, m), 2.56 (3H, s), 2.80 (2H, m), 3.07 (2H, m), 3.38 (2H, m), 4.59 (1H, m), 6.75 (1H, d, J=8 Hz), 6.81 (1H, d, J=8 Hz), 6.87 (1H, t, J=8 Hz)

MS (TSP); m/z 232 (MH$^+$)

Reference Example 12

2,3-Dihydro-5-methylspiro[isoquinoline-4(1H),4'-piperidin]-1-one trifluoroacetate (a) Bis(2-hydroxyethyl)benzylamine Bis(2-hydroxyethyl)amine (5 g) was dissolved in N,N-dimethylformamide (100 ml), added with benzyl bromide (6.52 ml) and potassium carbonate (8.657 g) and stirred at room temperature for 21 hours. The reaction mixture was added with water (200 ml) and extracted twice with dichloromethane (200 ml). The organic layer was dried over anhydrous magnesium sulfate, and then the solvent was evaporated under reduced pressure. The residue was purified by silica gel column chromatography (elution solvent: dichloromethane:methanol=20:1→10:1) to obtain 7.631 g of the title compound. Yield: 75%.

$^1$H-NMR (CDCl$_3$) δ (ppm); 2.34 (2H, br-s), 2.72 (4H, t, J=6 Hz), 3.63 (4H, t, J=6 Hz), 3.71 (2H, s), 7.20–7.40 (5H, m)

MS (FAB); m/z 196 (MH$^+$)

(b) 1-Benzyl-4-cyano-4-(2-methylphenyl)piperidine

Bis(2-hydroxyethyl)benzylamine (1 g) was dissolved in dichloromethane (20 ml), added with thionyl chloride (1.9 ml) with ice cooling and stirred at room temperature for 2.5 hours. The reaction mixture was added with water (10 ml) with ice cooling, and adjusted to pH 7 with saturated aqueous sodium hydrogencarbonate. The layers were separated and the aqueous layer was further extracted with dichloromethane (20 ml). The organic layer was dried over anhydrous magnesium sulfate, and then the solvent was evaporated under reduced pressure to obtain bis(2-chloroethyl)benzylamine (1.090 g).

1-(2-Methylphenyl)acetonitrile (610 mg) was dissolved in dimethyl sulfoxide (6.1 ml), added with sodium hydride (60%, in oil, 409 mg) and stirred at room temperature for 30 minutes. This reaction mixture was added with the solution of bis(2-chloroethyl)benzylamine (1.090 g) dissolved in dimethyl sulfoxide (6.1 ml) obtained above and further stirred at 75° C. for 2.5 hours. The reaction mixture was added with water (50 ml) and extracted twice with ether (50 ml). The organic layer was dried over anhydrous magnesium sulfate, and then the solvent was evaporated under reduced pressure. The residue was purified by silica gel column chromatography (elution solvent: hexane:ethyl acetate=6:1) to obtain 1.077 g of the title compound. Yield: 80%.

$^1$H-NMR (CDCl$_3$) δ (ppm); 2.07 (2H, td, J=12 Hz, 3 Hz), 2.32 (2H, dd, J=12 Hz, 3 Hz), 2.59 (2H, t, J=12 Hz), 2.64 (3H, s), 3.01 (2H, d, J=12 Hz), 3.61 (2H, s), 7.20–7.40 (9H, m)

MS (TSP); m/z 291 (MH$^+$)

(c) 4-Cyano-1-(ethoxycarbonyl)-4-(2-methylphenyl)piperidine

The title compound was obtained in the same manner in Reference Example 11(b) from 1-benzyl-4-cyano-4-(2-methylphenyl)piperidine. Yield: 100%.

$^1$H-NMR (CDCl$_3$) δ (ppm); 1.28 (3H, t, J=7 Hz), 1.92 (2H, td, J=12 Hz, 3 Hz), 2.34 (2H, d, J=12 Hz), 2.66 (3H, s), 3.33 (2H, m), 4.16 (2H, q, J=7 Hz), 4.34 (2H, m), 7.26 (4H, m)

MS (EI); m/z 272 (M$^+$)

(d) 1-(Ethoxycarbonyl)-4-(ethoxycarbonyl aminomethyl)-4-(2-methylphenyl)piperidine 4-Cyano-1-(ethoxycarbonyl)-4-(2-methylphenyl) piperidine (504 mg) was dissolved in ethanol (10 ml), added with 10% palladium/carbon (500 mg) and 5 N aqueous hydrochloric acid (0.74 ml) and stirred at room temperature for 15 hours under hydrogen gas pressure (30 psi) by using the Parr apparatus. After insoluble matters were removed by filtration, ethanol was evaporated under reduced pressure. The residue was added with dichloromethane (50 ml) and adjusted to pH 9 with saturated aqueous sodium hydrogencarbonate. The organic layer was separated, and the aqueous layer was further extracted with dichloromethane (50 ml). The organic layer was dried over anhydrous magnesium sulfate, and then the solvent was evaporated under reduced pressure to obtain 4-aminomethyl-1-(ethoxycarbonyl)-4-(2-methylphenyl)piperidine.

Subsequently, the resulting 4-aminomethyl-1-(ethoxycarbonyl)-4-(2-methylphenyl)piperidine was dissolved in dichloromethane (10 ml), added with ethyl chloroformate (0.18 ml) and triethylamine (0.26 ml) and stirred at room temperature for 30 minutes. After the reaction mixture was added with water (10 ml) and the layers were separated, the aqueous layer was further extracted with dichloromethane (10 ml). The organic layer was dried over anhydrous magnesium sulfate, and then the solvent was evaporated under reduced pressure. The residue was purified by silica gel column chromatography (elution solvent: hexane:ethyl acetate=2:1) to obtain 372 mg of the title compound. Yield: 51% (for the two steps).

$^1$H-NMR (CDCl$_3$) δ (ppm); 1.10–1.30 (6H, m), 1.85 (2H, m), 2.31 (2H, m), 2.51 (3H, s), 3.26 (2H, m), 3.53 (1H, s), 3.55 (1H, s), 3.74 (2H, m), 4.00–4.20 (4H, m), 4.29 (1H, br-s), 7.15–7.30 (4H, m)

MS (TSP); m/z 349 (MH$^+$)

(e) 1'-(tert-Butoxycarbonyl)-2,3-dihydro-5-methylspiro[isoquinoline-4(1H),4'-piperidin]-1-one 1-(Ethoxycarbonyl)-4-(ethoxycarbonylaminomethyl)-4-(2-methylphenyl)piperidine (327 mg) was dissolved in polyphosphoric acid (6.5 g) and stirred at 150° C. for 2 hours. The reaction mixture was added with ice (30 g), adjusted to pH 12 with 5 N aqueous sodium hydroxide and then extracted twice with dichloromethane (30 ml). The organic layer was dried over anhydrous magnesium sulfate, and then the solvent was evaporated under reduced pressure, and the residue was dissolved in dichloromethane (10 ml). The reaction mixture was added with di-tert-butyl dicarbonate (0.43 ml) and triethylamine (0.26 ml) and stirred at room temperature for 1 hour. After the reaction mixture was added with water (10 ml) and the layers were separated, the aqueous layer was further extracted with dichloromethane (10 ml). The organic layer was dried over anhydrous magnesium sulfate, and then the solvent was evaporated under reduced pressure. The residue was purified by silica gel column chromatography (elution solvent: hexane:ethyl acetate=1:2→ethyl acetate) to obtain 102 mg of the title compound. Yield: 33% (for the two steps).

$^1$H-NMR (CDCl$_3$) δ (ppm); 1.49 (9H, m), 1.73 (2H, d, J=12 Hz), 2.41 (2H, m), 2.56 (3H, s), 2.99 (2H, t, J=12 Hz), 3.59 (2H, s), 4.04 (2H, m), 6.17 (1H, br-s), 7.25–7.35 (2H, m), 8.04 (1H, d, J=8 Hz)

MS (TSP); m/z 331 (MH$^+$)

(f) 2,3-Dihydro-5-methylspiro[isoquinoline-4(1H), 4'-piperidin]-1-one trifluoroacetate The title compound was obtained in the same manner in Reference Example 3(c) from 1'-(tert-butoxycarbonyl)-2,3-dihydro-5-methylspiro[isoquinoline-4(1H),4'-piperidin]-1-one. Yield: 100%.

$^1$H-NMR (D$_2$O) δ (ppm); 1.96 (2H, d, J=14 Hz), 2.60 (3H, s), 2.70 (2H, td, J=14 Hz, 4 Hz), 3.26 (2H, t, J=14 Hz), 3.43

(2H, dd, J=14 Hz, 4 Hz), 3.63 (2H, s), 7.36 (1H, t, J=8 Hz), 7.46 (1H, d, J=8 Hz), 7.84 (1H, d, J=8 Hz)

MS (EI); m/z 230 (M$^+$)

Reference Example 13

4-(2-Hydroxymethyl-7-methyl-1H-benzimidazol-1-yl)piperidine

The 1-Ethoxycarbonyl-4-(1,3-dihydro-7-methyl-2H-benzimidazol-2-on-1-yl)piperidine (40 mg) obtained in Reference Example 11, (d) was dissolved in 5 N aqueous hydrochloric acid (0.8 ml), added with glycolic acid (16 mg) and stirred at 100° C. for 3 days. The reaction mixture was made alkaline by addition of aqueous ammonia and extracted twice with dichloromethane (2 ml). The organic layer was dried over anhydrous magnesium sulfate, and then the solvent was evaporated under reduced pressure to obtain 14.4 mg of the title compound. Yield: 41%.

$^1$H-NMR (CDCl$_3$) δ (ppm); 1.90 (2H, m), 2.42 (2H, m), 2.59 (3H, s), 2.82 (2H, m), 3.28 (2H, m), 4.57 (1H, m), 4.93 (2H, s), 7.01 (1H, d, J=8 Hz), 7.12 (1H, t, J=8 Hz), 7.48 (1H, d, J=8 Hz)

MS (EI); m/z 245 (M$^+$)

Reference Example 14

1-[2-(4-Isobutyloxycarbonylbenzyl)phenoxy]acetaldehyde (a) 4-Formyloxymethylbenzoic acid Formic acid (1.24 ml) and acetic anhydride (0.62 ml) were mixed and stirred at 50° C. for 30 minutes. This solution was cooled to 0° C., added with 4-hydroxymethylbenzoic acid (500 mg) and stirred at room temperature for 4.5 hours. The reaction mixture was added with water (5 ml) and extracted twice with ethyl acetate (5 ml). The organic layer was dried over anhydrous magnesium sulfate, and then the solvent was evaporated under reduced pressure to obtain 536 mg of the title compound. Yield: 91%.

$^1$H-NMR (DMSO-d$_6$) δ (ppm); 5.24 (2H, s), 7.49 (2H, d, J=8 Hz), 7.94 (2H, d, J=8 Hz), 8.40 (1H, s), 13.01 (1H, s)

(b) 4-(Formyloxymethyl)-N-(1,1-dimethyl-2-hydroxyethyl)benzamide

4-Formyloxymethylbenzoic acid (100 mg) was added with thionyl chloride (0.2 ml) and stirred at 80° C. for 1 hour. The solvent was evaporated under reduced pressure to obtain an acid chloride.

Separately, 2-amino-2-methylpropanol (53 μl) was dissolved in dichloromethane (1 ml), added with a solution of the aforementioned acid chloride dissolved in dichloromethane (1 ml) at 0° C. and triethylamine (77 μl) and stirred at the same temperature for 1 hour. The reaction mixture was added with water (5 ml) and extracted twice with dichloromethane (5 ml). The organic layer was dried over anhydrous magnesium sulfate, and then the solvent was evaporated under reduced pressure. The residue was purified by silica gel column chromatography (elution solvent: hexane:ethyl acetate=1:2) to obtain 64.5 mg of the title compound. Yield: 46%.

$^1$H-NMR (CDCl$_3$) δ (ppm); 1.42 (6H, s), 3.70 (1H, d, J=6 Hz), 4.54 (1H, d, J=6 Hz), 5.24 (2H, s), 6.19 (1H, m), 7.44 (2H, d, J=8 Hz), 7.74 (2H, d, J=8 Hz), 8.16 (1H, s)

MS (TSP); m/z 252 (MH$^+$)

(c) 4-(4,4-Dimethyloxazolin-2-yl)-1-(formyloxymethyl)benzene 4-(Formyloxymethyl)-N-(1,1-dimethyl-2-hydroxyethyl)benzamide (64 mg) was added with thionyl chloride (56 μl) and stirred at room temperature for 30 minutes. The solvent was evaporated under reduced pressure, and then the residue was added with water (5 ml) and extracted twice with ethyl acetate (5 ml). The organic layer was dried over anhydrous magnesium sulfate, and then the solvent was evaporated under reduced pressure. The residue was purified by preparative thin layer silica gel column chromatography (developing solvent: hexane:ethyl acetate=2:1) to obtain 37.4 mg of the title compound. Yield: 63%.

$^1$H-NMR (CDCl$_3$) δ (ppm); 1.38 (6H, s), 4.11 (2H, m), 5.23 (2H, s), 7.40 (2H, d, J=8 Hz), 7.95 (2H, d, J=8 Hz), 8.16 (1H, s)

MS (EI); m/z 232 (M$^+$)

(d) 4-(4,4-Dimethyloxazolin-2-yl)benzyl alcohol 4-(4,4-Dimethyloxazolin-2-yl)-1-(formyloxymethyl)benzene (37 mg) was dissolved in methanol (0.4 ml), added with 1 N aqueous sodium hydroxide (0.18 ml) and stirred at room temperature for 20 minutes. The reaction mixture was added with water (5 ml) and extracted twice with ethyl acetate (5 ml). The organic layer was dried over anhydrous magnesium sulfate, and then the solvent was evaporated under reduced pressure. The residue was purified by preparative thin layer silica gel column chromatography (developing solvent: hexane:ethyl acetate=1:2) to obtain 17.7 mg of the title compound. Yield: 54%.

$^1$H-NMR (CDCl$_3$) δ (ppm); 1.37 (6H, s), 4.10 (2H, s), 4.71 (2H, s), 7.35 (2H, d, J=8 Hz), 7.85 (2H, d, J=8 Hz)

(e) 4-(4,4-Dimethyloxazolin-2-yl)benzaldehyde

The title compound was obtained in the same manner in Reference Example 1(b) from 4-(4,4-dimethyloxazolin-2-yl)benzyl alcohol. Yield: 73%.

$^1$H-NMR (CDCl$_3$) δ (ppm); 1.41 (6H, s), 4.15 (2H, s), 7.92 (2H, d, J=8 Hz), 8.11 (2H, d, J=8 Hz), 10.07 (1H, s)

(f) 1-[4-(4,4-Dimethyloxazolin-2-yl)phenyl]-1-(2-methoxyphenyl)methyl alcohol

The title compound was obtained in the same manner in Reference Example 1(c) from 4-(4,4-dimethyloxazolin-2-yl)benzaldehyde. Yield: 81%.

$^1$H-NMR (CDCl$_3$) δ (ppm); 1.37 (6H, s), 3.18 (1H, d, J=6 Hz), 3.79 (3H, s), 4.09 (2H, s), 6.06 (1H, d, J=6 Hz), 6.88 (1H, d, J=8 Hz), 6.94 (1H, t, J=8 Hz), 7.20 (1H, d, J=8 Hz), 7.27 (1H, t, J=8 Hz), 7.42 (2H, d, J=8 Hz), 7.89 (2H, d, J=8 Hz)

(g) 2-[4-(4,4-Dimethyloxazolin-2-yl)benzyl]anisole

1-[4-(4,4-Dimethyloxazolin-2-yl)phenyl]-1-(2-methoxyphenyl)methyl alcohol (100 mg) was dissolved in pyridine (0.4 ml), added with acetic anhydride (0.25 ml) with ice cooling and stirred at room temperature for 4 hours. After the reaction mixture was added with methanol (0.25 ml) with ice cooling and stirred at room temperature for 10 minutes, the solvent was evaporated under reduced pressure to obtain 1-[4-(4,4-dimethyloxazolin-2-yl)phenyl]-1-(2-methoxyphenyl)methyl acetate.

In an amount of 23.5 mg of the 1-[4-(4,4-dimethyloxazolin-2-yl)phenyl]-1-(2-methoxyphenyl)methyl acetate obtained above was dissolved in methanol (0.47 ml), added with 10% palladium/carbon (24 mg) and ammonium formate (42 mg) under argon atmosphere and stirred at 60° C. for 2 hours. After insoluble matters were removed by filtration, the solvent was evaporated under reduced pressure. The residue was purified by preparative thin layer silica gel column chromatography (developing solvent: hexane::ethyl acetate=1:1) to obtain 14.4 mg of the title compound. Yield: 73%.

$^1$H-NMR (CDCl$_3$) δ (ppm); 1.36 (6H, s), 3.79 (3H, s), 3.99 (2H, s), 4.08 (2H, s), 6.87 (2H, t, J=8 Hz), 7.05 (1H, d, J=8 Hz), 7.20–7.25 (3H, m), 7.83 (2H, d, J=8 Hz)

MS (TSP); m/z 296 (MH$^+$)

(h) 2-(4-Carboxybenzyl)anisole

2-[4-(4,4-Dimethyloxazolin-2-yl)benzyl]anisole (22.3 mg) was dissolved in 5 N aqueous hydrochloric acid (2.2 ml) and stirred at 100° C. for 8 hours. The reaction mixture was extracted twice with dichloromethane (4 ml), and the organic layer was dried over anhydrous magnesium sulfate. Then, the solvent was evaporated under reduced pressure to obtain 15.3 mg of the title compound. Yield: 84%.

$^1$H-NMR (CDCl$_3$) δ (ppm); 3.80 (3H, s), 4.03 (2H, s), 6.89 (2H, m), 7.09 (1H, d, J=8 Hz), 7.22 (1H, t, J=8 Hz), 7.30 (2H, d, J=8 Hz), 8.00 (2H, d, J=8 Hz)

MS (TSP, negative); m/z 241 ([M−H]$^−$)

(i) 2-(4-Carboxybenzyl)phenol

The title compound was obtained in the same manner in Reference Example 5, (c) from 2-(4-carboxybenzyl)anisole. Yield: 60%.

$^1$H-NMR (DMSO-d$_6$) δ (ppm); 3.91 (2H, s), 6.71 (1H, t, J=8 Hz), 6.80 (1H, d, J=8 Hz), 7.04 (2H, m), 7.31 (2H, d, J=8 Hz), 7.82 (2H, d, J=8 Hz)

MS (EI); m/z 228 (M$^+$)

(j) 2-(4-Isobutyloxycarbonylbenzyl)phenol 2-(4-Carboxybenzyl)phenol (603 mg) was dissolved in isobutanol (3 ml), added with sulfuric acid (0.6 ml) and stirred at 80° C. for 3 hours. The reaction mixture was added with water (5 ml) and extracted twice with ethyl acetate (5 ml). The organic layer was dried over anhydrous magnesium sulfate, and then the solvent was evaporated under reduced pressure. The residue was purified by silica gel column chromatography (elution solvent: hexane:ethyl acetate=5:1) to obtain 318 mg of the title compound. Yield: 42%.

$^1$H-NMR (CDCl$_3$) δ (ppm); 1.00 (6H, d, J=7 Hz), 2.06 (1H, m), 4.04 (2H, s), 4.09 (2H, d, J=7 Hz), 6.78 (1H, d, J=8 Hz), 6.89 (1H, t, J=8 Hz), 7.12 (2H, m), 7.30 (2H, d, J=8 Hz), 7.96 (2H, d, J=8 Hz)

MS (FAB); m/z 285 (MH$^+$)

(k) 1-[2-(4-Isobutyloxycarbonylbenzyl)phenoxy]-2,3-dihydroxypropane

The title compound was obtained in the same manner in Reference Example 2(a) from 2-(4-isobutyloxycarbonylbenzyl)phenol. Yield: 61%.

$^1$H-NMR (CDCl$_3$) δ (ppm); 1.01 (6H, d, J=7 Hz), 1.94 (1H, s), 2.06 (1H, m), 2.19 (1H, s), 3.60 (1H, m), 3.70 (1H, m), 3.98 (3H, m), 4.03 (2H, s), 4.07 (2H, d, J=7 Hz), 6.86 (1H, d, J=8 Hz), 6.96 (1H, t, J=8 Hz), 7.16 (2H, d, J=8 Hz), 7.23 (2H, m), 7.96 (2H, d, J=8 Hz)

(l) 1-[2-(4-Isobutyloxycarbonylbenzyl)phenoxy]acetaldehyde

The title compound was obtained in the same manner in Reference Example 2(b) from 1-[2-(4-isobutyloxycarbonylbenzyl)phenoxy]-2,3-dihydroxypropane. Yield: 96%.

$^1$H-NMR (CDCl$_3$) δ (ppm); 1.01 (6H, d, J=7 Hz), 2.06 (1H, m), 4.08 (2H, d, J=7 Hz), 4.11 (2H, s), 4.53 (2H, s), 6.72 (1H, d, J=8 Hz), 6.98 (1H, t, J=8 Hz), 7.20 (2H, m), 7.29 (2H, d, J=8 Hz), 7.95 (2H, d, J=8 Hz), 9.75 (1H, s)

MS (FAB); m/z 327 (MH$^+$)

Reference Example 15

1-[2-[4-(2-Methylbutyryl)benzyl]phenoxy]acetaldehyde (a) 2-[4-(2-Methylbutyryl)benzyl]anisole The 2-(4-diethylcarbamoylbenzyl)anisole (100 mg) obtained in the process of Reference Example 1(d) was dissolved in toluene (2 ml), added with a solution of sec-butyl lithium in n-hexane and cyclohexane (1.0 M, 0.47 ml) at 0° C. under argon atmosphere and stirred at room temperature for 1 hour. After the reaction mixture was slowly poured into 1 N aqueous hydrochloric acid (5 ml) with ice cooling to quench the reaction and the layers were separated, the aqueous layer was extracted with ether (10 ml). The organic layer was washed with saline and dried over anhydrous magnesium sulfate, and then the solvent was evaporated under reduced pressure. The residue was purified by preparative thin layer silica gel column chromatography (developing solvent: hexane:ethyl acetate=2:1) to obtain 58.3 mg of the title compound. Yield: 61%.

$^1$H-NMR (CDCl$_3$) δ (ppm); 0.90 (3H, t, J=7 Hz), 1.17 (3H, d, J=7 Hz), 1.46 (1H, m), 1.81 (1H, m), 3.36 (1H, m), 3.80 (3H, s), 4.01 (2H, s), 6.89 (2H, m), 7.09 (1H, d, J=8 Hz), 7.22 (1H, t, J=8 Hz), 7.29 (2H, d, J=8 Hz), 7.86 (2H, d, J=8 Hz)

MS (EI); m/z 282 (M$^+$)

(b) 2-[4-(2-Methylbutyryl)benzyl]phenol

The title compound was obtained in the same manner in Reference Example 5, (c) from 2-[4-(2-methylbutyryl)benzyl]anisole. Yield: 87%.

$^1$H-NMR (CDCl$_3$) δ (ppm); 0.90 (3H, t, J=7 Hz), 1.17 (3H, d, J=7 Hz), 1.47 (1H, m), 1.82 (1H, m), 3.36 (1H, m), 4.04 (2H, s), 6.79 (1H, d, J=8 Hz), 6.90 (1H, t, J=8 Hz), 7.13 (2H, m), 7.32 (2H, d, J=8 Hz), 7.87 (2H, d, J=8 Hz)

MS (TSP); m/z 269 (MH$^+$)

(c) 1-[2-[4-(2-Methylbutyryl)benzyl]phenoxy]-2,3-dihydroxypropane

The title compound was obtained in the same manner in Reference Example 2(a) from 2-[4-(2-methylbutyryl)benzyl]phenol. Yield: 63%.

$^1$H-NMR (CDCl$_3$) δ (ppm); 0.90 (3H, t, J=7 Hz), 1.17 (3H, d, J=7 Hz), 1.47 (1H, m), 1.81 (1H, m), 1.92 (1H, s), 2.17 (1H, s), 3.35 (1H, m), 3.60 (1H, m), 3.70 (1H, m), 3.99 (2H, s), 4.03 (3H, m), 6.86 (1H, d, J=8 Hz), 6.96 (1H, t, J=8 Hz), 7.17 (2H, d, J=8 Hz), 7.26 (2H, d, J=8 Hz), 7.86 (2H, d, J=8 Hz)

MS (TSP); m/z 343 (MH$^+$)

(d) 1-[2-[4-(2-Methylbutyryl)benzyl]phenoxy]acetaldehyde

The title compound was obtained in the same manner in Reference Example 2(b) from 1-[2-[4-(2-methylbutyryl)benzyl]phenoxy]-2,3-dihydroxypropane. Yield: 85%.

$^1$H-NMR (CDCl$_3$) δ (ppm); 0.90 (3H, t, J=7 Hz), 1.17 (3H, d, J=7 Hz), 1.47 (1H, m), 1.81 (1H, m), 3.36 (1H, m), 4.11 (2H, s), 4.54 (2H, s), 6.73 (1H, d, J=8 Hz), 6.99 (1H, t, J=8 Hz), 7.20 (2H, m), 7.32 (2H, d, J=8 Hz), 7.87 (2H, d, J=8 Hz), 9.76 (1H, s)

Reference Example 16

2-Benzyl-2,3-dihydro-5-methylspiro[isoquinoline-4(1H),4'-piperidin]-1-one trifluoroacetate (a) 2-Benzyl-1'-(tert-butoxycarbonyl)-2,3-dihydro-5-methylspiro[isoquinoline-4(1H),4'-piperidin]-1-one 1'-(tert-Butoxycarbonyl)-2,3-dihydro-5-methylspiro[isoquinoline-4(1H),4'-piperidin]-1-one (80.7 mg) was dissolved in toluene (1.6 ml), added with sodium hydroxide (powder, 34.2 mg), potassium carbonate (67.4 mg), tetrabutylammonium hydrogensulfate (8.3 mg) and benzyl bromide (44 μl) and stirred at 70° C. for 3 hours. The reaction mixture was added with water (2 ml) and extracted twice with dichloromethane (2 ml). The organic layer was dried over anhydrous magnesium sulfate, and then the solvent was evaporated under reduced pressure. The residue was purified by preparative thin layer silica gel column chromatography (developing solvent: hexane:ethyl acetate=1:5) to obtain 86 mg of the title compound. Yield: 84%.

$^1$H-NMR (CDCl$_3$) δ (ppm); 1.44 (9H, s), 1.46 (2H, d, J=12 Hz), 2.20–2.45 (4H, m), 2.50 (3H, s), 3.47 (2H, s), 3.77 (2H, m), 4.78 (2H, m), 7.25–7.40 (7H, m), 8.13 (1H, t, J=8 Hz)

MS (FAB); m/z 421 (MH$^+$)

(b) 2-Benzyl-2,3-dihydro-5-methylspiro[isoquinoline-4(1H),4'-piperidin]-1-one trifluoroacetate The title compound was obtained in the same manner in Reference Example 3(c) from 2-benzyl-1'-(tert-butoxycarbonyl)-2,3-dihydro-5-methylspiro[isoquinoline-4(1H),4'-piperidin]-1-one. Yield: 100%.

Example 1

1-[2-[2-(4-Diethylcarbamoylbenzyl)phenoxy]ethyl]-4-(1,3-dihydro-2H-benzimidazol-2-on-1-yl)piperidine 4-(1,3-Dihydro-2H-benzimidazol-2-on-1-yl)piperidine (27.2 mg) was dissolved in dichloroethane (0.6 ml), added with the 1-[2-(4-diethylcarbamoylbenzyl)phenoxy]acetaldehyde (50.4 mg) obtained in Reference Example 2, sodium triacetoxyborohydride (39.7 mg) and acetic acid (0.12 ml) and stirred at room temperature for 18 hours. The reaction mixture was added with saturated aqueous sodium hydrogencarbonate (2 ml) and extracted twice with dichloromethane (2 ml). The organic layer was dried over anhydrous magnesium sulfate, and then the solvent was evaporated under reduced pressure. The residue was by purified preparative thin layer silica gel column chromatography (developing solvent: ethyl acetate:methanol=20:1) to obtain 29.8 mg of the title compound. Yield: 45%.

$^1$H-NMR (CDCl$_3$) δ (ppm); 1.10 (3H, br-s), 1.18 (3H, br-s), 1.80 (2H, m), 2.30–2.60 (4H, m), 2.86 (2H, t, J=5 Hz), 3.15–3.35 (4H, m), 3.50 (2H, br-s), 4.00 (2H, s), 4.15 (2H, t, J=5 Hz), 4.38 (1H, m), 6.85–6.95 (2H, m), 7.00–7.15 (4H, m), 7.20–7.35 (6H, m), 9.41 (1H, s)

MS (TSP); m/z 527 (MH$^+$)

Example 2

1-[3-[2-(4-Diethylcarbamoylbenzyl)phenoxy]propyl]-4-(1,3-dihydro-2H-benzimidazol-2-on-1-yl)piperidine 4-(1,3-Dihydro-2H-benzimidazol-2-on-1-yl)piperidine (49 mg) was dissolved in methyl ethyl ketone (1.8 ml), added with the 1-bromo-3-[2-(4-diethylcarbamoylbenzyl)phenoxy]propane (91 mg) obtained in Reference Example 1 and triethylamine (47 μl) and stirred at room temperature for 17 hours. The reaction mixture was added with water (2 ml) and extracted twice with ethyl acetate (2 ml). The organic layer was dried over anhydrous magnesium sulfate, and then the solvent was evaporated under reduced pressure. The residue was purified by silica gel column chromatography (elution solvent: dichloromethane:methanol=20:1) to obtain 49.7 mg of the title compound. Yield: 41%.

$^1$H-NMR (CDCl$_3$) δ (ppm); 1.11 (3H, br-s), 1.21 (3H, br-s), 1.82 (2H, m), 1.99 (2H, m), 2.15 (2H, m), 2.46 (2H, m), 2.53 (2H, t, J=5 Hz), 3.07 (2H, m), 3.26 (2H, br-s), 3.51 (2H, br-s), 4.00 (2H, s), 4.04 (2H, t, J=5 Hz), 4.37 (1H, m), 6.90 (2H, m), 7.03–7.12 (4H, m), 7.20–7.28 (6H, m), 9.66 (1H, s)

MS (EI); m/z 541 (M$^+$)

Example 3

8-[2-[2-(4-Diethylcarbamoylbenzyl)phenoxy]ethyl]-1-phenyl-1,3,8-triazaspiro[4,5]decan-4-one The title compound was obtained in the same manner in Example 1 from the 1-[2-(4-diethylcarbamoylbenzyl)phenoxy]acetaldehyde obtained in Reference Example 2 and 1-phenyl-1,3,8-triazaspiro[4,5]decan-4-one. Yield: 29%.

$^1$H-NMR (CDCl$_3$) δ (ppm); 1.10 (3H, br-s), 1.25 (3H, br-s), 1.69 (2H, d, J=14 Hz), 2.70 (2H, m), 2.94 (6H, m), 3.24 (2H, br-s), 3.51 (2H, br-s), 3.99 (2H, s), 4.18 (2H, m), 4.72 (2H, s), 6.80–7.00 (6H, m), 7.05–7.30 (8H, m)

MS (TSP); m/z 541 (MH$^+$)

Example 4

3-Benzyl-8-[2-[2-(4-diethylcarbamoylbenzyl)phenoxy]ethyl]-1-phenyl-1,3,8-triazaspiro[4,5]decan-4-one The title compound was obtained in the same manner in Example 1 from the 1-[2-(4-diethylcarbamoylbenzyl)phenoxy]acetaldehyde obtained in Reference Example 2 and the 3-benzyl-1-phenyl-1,3,8-triazaspiro[4,5]decan-4-one trifluoroacetate obtained in Reference Example 3. Yield: 50%.

$^1$H-NMR (CDCl$_3$) δ (ppm); 1.09 (3H, br-s), 1.20 (3H, br-s), 1.69 (2H, d, J=14 Hz), 2.60–3.30 (10H, m), 3.50 (2H, br-s), 4.00 (2H, s), 4.19 (2H, m), 4.58 (2H, s), 4.60 (2H, s), 6.75–6.95 (6H, m), 7.05–7.40 (12H, m)

MS (TSP); m/z 631 (MH$^+$)

Example 5

3-Cyclopropylmethyl-8-[2-[2-(4-diethylcarbamoylbenzyl)phenoxy]ethyl]-1-phenyl-1,3,8-triazaspiro[4,5]decan-4-one The title compound was obtained in the same manner in Example 1 from the 1-[2-(4-diethylcarbamoylbenzyl)phenoxy]acetaldehyde obtained in Reference Example 2 and 3-cyclopropylmethyl-1-phenyl-1,3,8-triazaspiro[4,5]decan-4-one trifluoroacetate obtained in the same manner in Reference Example 3. Yield: 49%.

$^1$H-NMR (CDCl$_3$) δ (ppm); 0.29 (2H, m), 0.59 (2H, m), 1.00 (1H, m), 1.10 (3H, br-s), 1.18 (3H, br-s), 1.66 (2H, d, J=14 Hz), 2.70–3.30 (10H, m), 3.30 (2H, d, J=7 Hz), 3.50 (2H, br-s), 3.98 (2H, s), 4.25 (2H, m), 4.80 (2H, s), 6.75–7.00 (6H, m), 7.05–7.35 (7H, m)

MS (TSP); m/z 595 (MH$^+$)

Example 6

1-[4-[2-(4-Diethylcarbamoylbenzyl)phenoxy]butyl]-4-(1,3-dihydro-2H-benzimidazol-2-on-1-yl)piperidine The title compound obtained in the same manner in Example 2 from 1-bromo-4-[2-(4-diethylcarbamoylbenzyl)phenoxy]butane obtained in the same manner in Reference Example 1 and 4-(1,3-dihydro-2H-benzimidazol-2-on-1-yl)piperidine. Yield: 37%.

$^1$H-NMR (CDCl$_3$) δ (ppm); 1.10 (3H, br-s), 1.20 (3H, br-s), 1.69 (2H, m), 1.82 (4H, m), 2.35 (2H, m), 2.46 (4H, m), 3.10 (2H, m), 3.26 (2H, br-s), 3.51 (2H, br-s), 4.00 (4H, m), 4.40 (1H, m), 6.88 (2H, m), 7.03 (2H, m), 7.09 (2H, m), 7.18–7.29 (6H, m), 9.81 (1H, s)

MS (EI); m/z 554 (M$^+$)

Example 7

8-[4-[2-(4-Diethylcarbamoylbenzyl)phenoxy]butyl]-1-phenyl-1,3,8-triazaspiro[4,5]decan-4-one The title compound was obtained in the same manner in Example 2 from 1-bromo-4-[2-(4-diethylcarbamoylbenzyl)phenoxy]butane obtained in the same manner in Reference Example 1 and 1-phenyl-1,3,8-triazaspiro[4,5]decan-4-one. Yield: 44%.

$^1$H-NMR (CDCl$_3$) δ (ppm); 1.09 (3H, br-s), 1.20 (3H, br-s), 1.68 (6H, m), 2.58 (2H, m), 2.91 (6H, m), 3.26 (2H, br-s), 3.50 (2H, br-s), 3.99 (4H, m), 4.72 (2H, s), 6.85 (3H, m), 6.95 (2H, m), 7.09 (1H, m), 7.16–7.30 (8H, m)

MS (EI); m/z 568 (M$^+$)

Example 8

8-[3-[2-(4-diethylcarbamoylbenzyl)phenoxy]propyl]-1-phenyl-1,3,8-triazaspiro[4,5]decan-4-one The title compound was obtained in the same manner in Example 2 from the 1-bromo-3-[2-(4-diethylcarbamoylbenzyl)phenoxy]propane obtained in Reference Example 1 and 1-phenyl-1,3,8-triazaspiro[4,5]decan-4-one. Yield: 48%.

$^1$H-NMR (CDCl$_3$) δ (ppm); 1.11 (3H, br-s), 1.21 (3H, br-s), 1.76 (4H, m), 2.06 (2H, m), 2.64 (2H, m), 2.92 (4H, m), 3.26 (2H, br-s), 3.51 (2H, br-s), 3.98 (2H, s), 4.03 (2H, t, J=5 Hz), 4.72 (2H, s), 6.70–7.30 (14H, m)

MS (EI); m/z 554 (M$^+$)

Example 9

1-[2-[2-(4-Diethylcarbamoylbenzyl)phenoxy]ethyl]-4-(3-benzyl-1,3-dihydro-2H-benzimidazol-2-on-1-yl)piperidine The title compound was obtained in the same manner in Example 1 from the 1-[2-(4-diethylcarbamoylbenzyl)phenoxy]acetaldehyde obtained in Reference Example 2 and 4-(3-benzyl-1,3-dihydro-2H-benzimidazol-2-on-1-yl)piperidine trifluoroacetate obtained in the same manner in Reference Example 3. Yield: 50%.

$^1$H-NMR (CDCl$_3$) δ (ppm); 1.09 (3H, br-s), 1.19 (3H, br-s), 1.83 (2H, d, J=14 Hz), 2.30–2.55 (4H, m), 2.84 (2H, t, J=5 Hz), 3.15 (2H, d, J=12 Hz), 3.24 (2H, br-s), 3.49 (2H, br-s), 4.00 (2H, s), 4.13 (2H, t, J=5 Hz), 4.45 (1H, m), 5.06 (2H, s), 6.85–7.40 (17H, m)

MS (TSP); m/z 617 (MH$^+$)

Example 10

1-[2-[2-(4-Diethylcarbamoylbenzyl)phenoxy]ethyl]-4-(3-cyclopropylmethyl-1,3-dihydro-2H-benzimidazol-2-on-1-yl)piperidine The title compound was obtained in the same manner in Example 1 from the 1-[2-(4-diethylcarbamoylbenzyl)phenoxy]acetaldehyde obtained in Reference Example 2 and 4-(3-cyclopropylmethyl-1,3-dihydro-2H-benzimidazol-2-on-1-yl)piperidine trifluoroacetate obtained in the same manner in Reference Example 3. Yield: 71%.

$^1$H-NMR (CDCl$_3$) δ (ppm); 0.42 (2H, m), 0.55 (2H, m), 1.05–1.30 (7H, m), 1.80 (2H, m), 2.25–2.55 (4H, m), 2.84 (2H, t, J=5 Hz), 3.14 (2H, d, J=12 Hz), 3.24 (2H, br-s), 3.50 (2H, br-s), 3.75 (2H, d, J=7 Hz), 4.00 (2H, s), 4.12 (2H, t, J=5 Hz), 4.41 (1H, m), 6.85–6.95 (2H, m), 7.05–7.10 (4H, m), 7.15–7.35 (6H, m)

MS (FAB); m/z 581 (MH$^+$)

Example 11

1'-[2-[2-(4-Diethylcarbamoylbenzyl)phenoxy]ethyl]hexahydrospiro-[imidazo[1,2-a]pyridine-3(2H),4'-piperidin]-2-one The title compound was obtained in the same manner in Example 1 from the 1-[2-(4-diethylcarbamoylbenzyl)phenoxy]acetaldehyde obtained in Reference Example 2 and hexahydrospiro[imidazo[1,2-a]pyridine-3(2H),4'-piperidin]-2-one synthesized in accordance with the descriptions of Yakugaku Zasshi, 1989, 109, 93. Yield: 38%.

$^1$H-NMR (CDCl$_3$) δ (ppm); 1.12 (3H, br-s), 1.21 (3H, br-s), 1.35 (2H, m), 1.51 (1H, m), 1.67 (5H, m), 1.83 (2H, m), 2.39 (1H, td, J=12 Hz, 3 Hz), 2.63 (1H, m), 2.85 (5H, m), 3.10–3.35 (3H, m), 3.51 (2H, br-s), 3.94 (1H, m), 3.97 (2H, s), 4.11 (2H, m), 5.81 (1H, s), 6.80–6.95 (2H, m), 7.08 (1H, d, J=8 Hz), 7.15–7.30 (5H, m)

MS (FAB); m/z 519 (MH$^+$)

Example 12

1'-[2-[2-(4-Diethylcarbamoylbenzyl)phenoxy]ethyl]-5,6,7,8-tetrahydrospiro[imidazo[1,2-a]pyridine-3(2H),4'-piperidin]-2-one The title compound was obtained in the same manner in Example 1 from the 1-[2-(4-diethylcarbamoylbenzyl)phenoxy]acetaldehyde obtained in Reference Example 2 and 5,6,7,8-tetrahydrospiro[imidazo[1,2-a]pyridine-3(2H),4'-piperidin]-2-one synthesized in accordance with the descriptions of Yakugaku Zasshi, 1989, 109, 93. Yield: 68%.

$^1$H-NMR (CDCl$_3$) δ (ppm); 1.11 (3H, br-s), 1.21 (3H, br-s), 1.57 (2H, d, J=12 Hz), 1.75–2.00 (6H, m), 2.70–2.85 (4H, m), 2.91 (2H, t, J=5 Hz), 3.15 (2H, t, J=12 Hz), 3.23 (4H, m), 3.51 (2H, m), 3.98 (2H, s), 4.11 (2H, t, J=5 Hz), 6.80–6.90 (2H, m), 7.10 (1H, d, J=8 Hz), 7.15–7.30 (5H, m)

MS (FAB); m/z 517 (MH$^+$)

Example 13

1-[2-[2-(4-Dimethylcarbamoylbenzyl)phenoxy]ethyl]-4-(1,3-dihydro-2H-benzimidazol-2-on-1-yl)piperidine The title compound was obtained in the same manner in Example 1 from 1-[2-(4-dimethylcarbamoylbenzyl)phenoxy]acetaldehyde obtained in the same manner in Reference Example 2 and 4-(1,3-dihydro-2H-benzimidazol-2-on-1-yl)piperidine. Yield: 64%.

¹H-NMR (CDCl₃) δ (ppm); 1.81 (2H, m), 2.33 (2H, m), 2.47 (2H, m), 2.86 (2H, t, J=5 Hz), 2.96 (3H, br-s), 3.07 (3H, br-s), 3.14 (2H, m), 4.01 (2H, s), 4.13 (2H, t, J=5 Hz), 4.35 (1H, m), 6.90 (2H, m), 7.02–7.12 (4H, m), 7.19–7.25 (4H, m), 7.32 (2H, m), 9.92 (1H, s)

MS (FAB); m/z 499 (MH⁺)

Example 14

8-[2-[2-(4-Dimethylcarbamoylbenzyl)phenoxy]ethyl]-1-phenyl-1,3,8-triazaspiro[4,5]decan-4-one The title compound was obtained in the same manner in Example 1 from 1-[2-(4-dimethylcarbamoylbenzyl)phenoxy]acetaldehyde obtained in the same manner in Reference Example 2 and 1-phenyl-1,3,8-triazaspiro[4,5]decan-4-one. Yield: 30%.

¹H-NMR (CDCl₃) δ (ppm); 2.63 (2H, m), 2.87 (6H, m), 2.95 (3H, br-s), 3.08 (5H, m), 4.00 (2H, s), 4.13 (2H, m), 4.72 (2H, s), 6.89 (6H, m), 7.08 (2H, m), 7.25 (6H, m)

MS (EI); m/z 512 (M⁺)

Example 15

4-(1,3-Dihydro-2H-benzimidazol-2-on-1-yl)-1-[2-[2-(4-pyrrolidinocarbonyl-benzyl)phenoxy]ethyl]piperidine The title compound was obtained in the same manner in Example 1 from 1-[2-(4-pyrrolidinocarbonylbenzyl)phenoxy]acetaldehyde obtained in the same manner in Reference Example 2 and 4-(1,3-dihydro-2H-benzimidazol-2-on-1-yl)piperidine. Yield: 48%.

¹H-NMR (CDCl₃) δ (ppm); 1.66 (2H, m), 1.81 (2H, m), 1.91 (2H, m), 2.34 (2H, m), 2.46 (2H, m), 2.85 (2H, t, J=5 Hz), 3.14 (2H, m), 3.41 (2H, t, J=7 Hz), 3.61 (2H, t, J=7 Hz), 4.01 (2H, s), 4.13 (2H, t, J=5 Hz), 4.36 (1H, m), 6.90 (3H, m), 7.05 (3H, m), 7.22 (5H, m), 7.43 (1H, d, J=8 Hz)

MS (TSP); m/z 525 (MH⁺)

Example 16

1-Phenyl-8-[2-[2-(4-pyrrolidinocarbonylbenzyl)phenoxy]ethyl]-1,3,8-triazaspiro[4,5]decan-4-one The title compound was obtained in the same manner in Example 1 from 1-[2-(4-pyrrolidinocarbonylbenzyl)phenoxy]acetaldehyde obtained in the same manner in Reference Example 2 and 1-phenyl-1,3,8-triazaspiro[4,5]decan-4-one. Yield: 27%.

¹H-NMR (CDCl₃) δ (ppm); 1.84 (2H, m), 1.92 (2H, m), 2.67 (2H, m), 2.89 (2H, m), 2.99 (2H, m), 3.30 (2H, m), 3.41 (2H, t, J=7 Hz), 3.58 (2H, m), 3.62 (2H, t, J=7 Hz), 4.01 (2H, s), 4.13 (2H, m), 4.71 (2H, s), 6.80–7.43 (14H, m)

MS (TSP); m/z 539 (MH⁺)

Example 17

1-[2-[3-(4-Diethylcarbamoylbenzyl)phenoxy]ethyl]-4-(1,3-dihydro-2H-benzimidazol-2-on-1-yl)piperidine The title compound was obtained in the same manner in Example 1 from 1-[3-(4-diethylcarbamoylbenzyl)phenoxy]acetaldehyde obtained in the same manner in Reference Example 2 and 4-(1,3-dihydro-2H-benzimidazol-2-on-1-yl)piperidine. Yield: 49%.

¹H-NMR (CDCl₃) δ (ppm); 1.12 (3H, br-s), 1.21 (3H, br-s), 1.82 (2H, m), 2.34 (2H, t, J=12 Hz), 2.51 (2H, q, J=12 Hz), 2.85 (2H, t, J=5 Hz), 3.17 (2H, d, J=12 Hz), 3.27 (2H, br-s), 3.53 (2H, br-s), 3.97 (2H, s), 4.11 (2H, t, J=5 Hz), 4.39 (1H, m), 6.75–6.85 (3H, m), 7.00–7.15 (3H, m), 7.20–7.35 (6H, m), 9.57 (1H, s)

MS (TSP); m/z 527 (MH⁺)

Example 18

8-[2-[3-(4-Diethylcarbamoylbenzyl)phenoxy]ethyl]-1-phenyl-1,3,8-triazaspiro[4,5]decan-4-one The title compound was obtained in the same manner in Example 1 from 1-[3-(4-diethylcarbamoylbenzyl)phenoxy]acetaldehyde obtained in the same manner in Reference Example 2 and 1-phenyl-1,3,8-triazaspiro[4,5]decan-4-one. Yield: 29%.

¹H-NMR (CDCl₃) δ (ppm); 1.12 (3H, br-s), 1.22 (3H, br-s), 1.72 (2H, d, J=14 Hz), 2.70 (2H, m), 2.85–3.10 (6H, m), 3.26 (2H, br-s), 3.52 (2H, br-s), 3.95 (2H, s), 4.11 (2H, t, J=5 Hz), 4.71 (2H, s), 6.70–7.00 (6H, m), 7.15–7.35 (8H, m)

MS (TSP); m/z 541 (MH⁺)

Example 19

1-[2-[4-(4-Diethylcarbamoylbenzyl)phenoxy]ethyl]-4-(1,3-dihydro-2H-benzimidazol-2-on-1-yl)piperidine The title compound was obtained in the same manner in Example 1 from 1-[4-(4-diethylcarbamoylbenzyl)phenoxy]acetaldehyde obtained in the same manner in Reference Example 2 and 4-(1,3-dihydro-2H-benzimidazol-2-on-1-yl)piperidine. Yield: 49%.

¹H-NMR (CDCl₃) δ (ppm); 1.12 (3H, br-s), 1.22 (3H, br-s), 1.80 (2H, m), 2.34 (2H, t, J=12 Hz), 2.51 (2H, q, J=12 Hz), 2.88 (2H, t, J=5 Hz), 3.17 (2H, d, J=12 Hz), 3.27 (2H, br-s), 3.52 (2H, br-s), 3.94 (2H, s), 4.13 (2H, t, J=5 Hz), 4.39 (1H, m), 6.86 (2H, d, J=8 Hz), 7.00–7.15 (4H, m), 7.18 (2H, d, J=8 Hz), 7.25–7.35 (4H, m), 9.52 (1H, s)

MS (TSP); m/z 527 (MH⁺)

Example 20

8-[2-[4-(4-Diethylcarbamoylbenzyl)phenoxy]ethyl]-1-phenyl-1,3,8-triazaspiro[4,5]decan-4-one The title compound was obtained in the same manner in Example 1 from 1-[4-(4-diethylcarbamoylbenzyl)phenoxy]acetaldehyde obtained in the same manner in Reference Example 2 and 1-phenyl-1,3,8-triazaspiro[4,5]decan-4-one. Yield: 36%.

¹H-NMR (CDCl₃) δ (ppm); 1.12 (3H, br-s), 1.21 (3H, br-s), 1.72 (2H, d, J=14 Hz), 2.70 (2H, m), 2.85–3.10 (6H, m), 3.26 (2H, br-s), 3.52 (2H, br-s), 3.93 (2H, s), 4.12 (2H, t, J=5 Hz), 4.72 (2H, s), 6.70–7.00 (6H, m), 7.08 (2H, d, J=8 Hz), 7.18 (2H, d, J=8 Hz), 7.25–7.35 (4H, m)

MS (TSP); m/z 541 (MH⁺)

Example 21

4-(1,3-dihydro-2H-benzimidazol-2-on-1-yl)-1-[2-[2-(4-piperidinocarbonylbenzyl)phenoxy]ethyl]piperidine The title compound was obtained in the same manner in Example 1 from 1-[2-(4-piperidinocarbonylbenzyl)phenoxy]acetaldehyde obtained in the same manner in Reference Example 2 and 4-(1,3-dihydro-2H-benzimidazol-2-on-1-yl)piperidine. Yield: 40%.

$^1$H-NMR (CDCl$_3$) δ (ppm); 1.47 (2H, m), 1.62 (4H, m), 1.81 (2H, m), 2.38 (2H, m), 2.51 (2H, m), 2.89 (2H, t, J=5 Hz), 3.19 (2H, m), 3.31 (2H, m), 3.68 (2H, m), 4.00 (2H, s), 4.17 (2H, t, J=5 Hz), 4.40 (1H, m), 6.89 (2H, m), 7.03 (2H, m), 7.10 (2H, m), 7.19–7.30 (6H, m), 10.22 (1H, s)

MS (TSP); m/z 539 (MH$^+$)

Example 22

1-Phenyl-8-[2-[2-(4-piperidinocarbonylbenzyl) phenoxy]ethyl]-1,3,8-triazaspiro[4,5]decan-4-one The title compound was obtained in the same manner in Example 1 from 1-[2-(4-piperidinocarbonylbenzyl) phenoxy]acetaldehyde obtained in the same manner in Reference Example 2 and 1-phenyl-1,3,8-triazaspiro[4,5]decan-4-one. Yield: 14%.

$^1$H-NMR (CDCl$_3$) δ (ppm); 1.47 (2H, m), 1.61 (6H, m), 2.64 (2H, m), 2.88 (4H, m), 2.96 (2H, m), 3.33 (2H, m), 3.67 (2H, m), 4.00 (2H, s), 4.13 (2H, m), 4.73 (2H, s), 6.18 (1H, m), 6.88 (6H, m), 7.10 (1H, m), 7.24 (6H, m)

MS (TSP); m/z 553 (MH$^+$)

Example 23

1-[2-[2-(4-Diethylcarbamoylbenzoyl)phenoxy] ethyl]-4-(1,3-dihydro-2H-benzimidazol-2-on-1-yl) piperidine The title compound was obtained in the same manner in Example 1 from 1-[2-(4-diethylcarbamoylbenzoyl) phenoxy]acetaldehyde obtained in the same manner in Reference Example 2 and 4-(1,3-dihydro-2H-benzimidazol-2-on-1-yl)piperidine. Yield: 16%.

$^1$H-NMR (CDCl$_3$) δ (ppm); 1.09 (3H, br-s), 1.24 (3H, br-s), 1.73 (2H, m), 2.15 (2H, m), 2.40 (2H, m), 2.56 (2H, m), 2.94 (2H, m), 3.21 (2H, br-s), 3.55 (2H, br-s), 4.10 (2H, m), 4.29 (1H, m), 7.00–7.11 (6H, m), 7.43 (3H, m), 7.50 (1H, m), 7.83 (2H, d, J=8 Hz), 8.80 (1H, s)

MS (TSP); m/z 541 (MH$^+$)

Example 24

8-[2-[2-(4-Diethylcarbamoylbenzoyl)phenoxy] ethyl]-1-phenyl-1,3,8-triazaspiro[4,5]decan-4-one The title compound was obtained in the same manner in Example 1 from 1-[2-(4-diethylcarbamoylbenzoyl) phenoxy]acetaldehyde obtained in the same manner in Reference Example 2 and 1-phenyl-1,3,8-triazaspiro[4,5]decan-4-one. Yield: 10%.

$^1$H-NMR (CDCl$_3$) δ (ppm); 1.10 (3H, br-s), 1.24 (3H, br-s), 1.60 (2H, m), 2.58 (6H, m), 2.80 (2H, m), 3.22 (2H, br-s), 3.54 (2H, br-s), 4.08 (2H, t, J=5 Hz), 4.70 (2H, s), 6.23 (1H, s), 6.88 (3H, m), 7.02 (1H, d, J=8 Hz), 7.06 (1H, d, J=8 Hz), 7.27 (2H, m), 7.40 (3H, m), 7.48 (1H, m), 7.81 (2H, d, J=8 Hz)

MS (TSP); m/z 555 (MH$^+$)

Example 25

1-[2-[2-[1-(4-Diethylcarbamoylphenyl)-1-hydroxymethyl]phenoxy]ethyl]-4-(1,3-dihydro-2H-benzimidazol-2-on-1-yl)piperidine The 1-[2-[2-(4-diethylcarbamoylbenzoyl)phenoxy] ethyl]-4-(1,3-dihydro-2H-benzimidazol-2-on-1-yl) piperidine (39 mg) obtained in Example 23 was dissolved in ethanol (1 ml), added with sodium borohydride (1 mg) with ice cooling and stirred at room temperature for 30 minutes. The reaction mixture was added with water (5 ml) and extracted twice with ethyl acetate (5 ml). The organic layer was dried over anhydrous magnesium sulfate, and then the solvent was evaporated under reduced pressure. The residue was purified by preparative thin layer silica gel column chromatography (developing solvent: ethyl acetate:methanol=10:1) to obtain 27.2 mg of the title compound. Yield: 70%.

$^1$H-NMR (CDCl$_3$) δ (ppm); 1.16 (3H, br-s), 1.26 (3H, br-s), 1.78 (2H, m), 2.25 (2H, m), 2.70 (4H, m), 3.02 (1H, m), 3.21 (1H, m), 3.33 (2H, br-s), 3.58 (2H, br-s), 4.23 (1H, m), 4.30 (1H, m), 4.44 (1H, m), 6.19 (1H, s), 6.82 (1H, m), 6.89 (1H, t, J=8 Hz), 7.01 (4H, m), 7.44 (2H, d, J=8 Hz), 7.57 (2H, d, J=8 Hz), 7.82 (2H, d, J=8 Hz), 8.73 (1H, s)

MS (TSP); m/z 543 (MH$^+$)

Example 26

8-[2-[2-[1-(4-Diethylcarbamoylphenyl)-1-hydroxymethyl]phenoxy]ethyl]-1-phenyl-1,3,8-triazaspiro[4,5]decan-4-one The title compound was obtained in the same manner in Example 26 from 8-[2-[2-(4-diethylcarbamoylbenzoyl) phenoxy]ethyl]-1-phenyl-1,3,8-triazaspiro[4,5]-decan-4-one obtained in Example 24. Yield: 56%.

$^1$H-NMR (CDCl$_3$) δ (ppm); 1.14 (3H, br-s), 1.26 (3H, br-s), 1.69 (2H, t, J=14 Hz), 2.78 (3H, m), 2.95 (5H, m), 3.31 (2H, br-s), 3.56 (2H, br-s), 4.26 (2H, m), 4.72 (2H, s), 6.13 (1H, s), 6.77 (3H, m), 6.89 (2H, d, J=8 Hz), 6.98 (1H, d, J=8 Hz), 7.03 (2H, d, J=8 Hz), 7.19 (2H, t, J=8 Hz), 7.20 (2H, t, J=8 Hz), 7.56 (2H, d, J=8 Hz)

MS (TSP); m/z 557 (MH$^+$)

Example 27

1-[2-[2-(3-Diethylcarbamoylbenzyl)phenoxy]ethyl]-4-(1,3-dihydro-2H-benzimidazol-2-on-1-yl) piperidine The title compound was obtained in the same manner in Example 1 from 1-[2-(3-diethylcarbamoylbenzyl)phenoxy] acetaldehyde obtained in the same manner in Reference Example 2 and 4-(1,3-dihydro-2H-benzimidazol-2-on-1-yl) piperidine. Yield: 44%.

$^1$H-NMR (CDCl$_3$) δ (ppm); 1.03 (3H, br-s), 1.21 (3H, br-s), 1.80 (2H, d, J=12 Hz), 2.32 (2H, t, J=12 Hz), 2.46 (2H, q, J=12 Hz), 2.85 (2H, t, J=5 Hz), 3.12 (2H, d, J=12 Hz), 3.19 (2H, br-s), 3.50 (2H, br-s), 4.01 (2H, s), 4.13 (2H, t, J=5 Hz), 4.37 (1H, m), 6.85–6.95 (2H, m), 7.00–7.30 (10H, m), 9.83 (1H, s)

MS (TSP); m/z 527 (MH$^+$)

Example 28

8-[2-[2-(3-Diethylcarbamoylbenzyl)phenoxy]ethyl]-1-phenyl-1,3,8-triazaspiro[4,5]decan-4-one The title compound was obtained in the same manner in Example 1 from 1-[2-(3-diethylcarbamoylbenzyl)phenoxy] acetaldehyde obtained in the same manner in Reference Example 2 and 1-phenyl-1,3,8-triazaspiro[4,5]decan-4-one. Yield: 32%.

$^1$H-NMR (CDCl$_3$) δ (ppm); 1.02 (3H, br-s), 1.21 (3H, br-s), 1.70 (2H, d, J=14 Hz), 2.66 (2H, m), 2.80–3.10 (6H, m), 3.19 (2H, br-s), 3.50 (2H, br-s), 4.00 (2H, s), 4.13 (2H, m), 4.72 (2H, s), 6.80–6.95 (6H, m), 7.05–7.30 (8H, m)

MS (TSP); m/z 541 (MH$^+$)

Example 29

1-[2-[2-(4-Diethylcarbamoylbenzyl)phenoxy]propyl]-4-(1,3-dihydro-2H-benzimidazol-2-on-1-yl)piperidine The title compound was obtained in the same manner in Example 2 from 1-bromo-2-[2-(4-diethylcarbamoylbenzyl)phenoxy]propane obtained in the same manner in Reference Example 1 and 4-(1,3-dihydro-2H-benzimidazol-2-on-1-yl)piperidine. Yield: 29%.

$^1$H-NMR (CDCl$_3$) δ (ppm); 1.13 (3H, br-s), 1.20 (3H, br-s), 1.25 (3H, d, J=5 Hz), 1.76 (2H, m), 2.20–2.45 (4H, m), 2.52 (1H, dd, J=12 Hz, 4 Hz), 2.71 (1H, dd, J=12 Hz, 7 Hz), 3.07 (2H, m), 3.25 (2H, br-s), 3.51 (2H, br-s), 3.94 (1H, d, J=15 Hz), 4.04 (1H, d, J=15 Hz), 4.33 (1H, m), 4.60 (1H, q, J=5 Hz), 6.80–7.00 (2H, m), 7.00–7.15 (4H, m), 7.18–7.30 (6H, m), 8.91 (1H, s)

MS (TSP); m/z 541 (MH$^+$)

Example 30

8-[2-[2-(4-Diethylcarbamoylbenzyl)phenoxy]propyl]-1-phenyl-1,3,8-triazaspiro[4,5]decan-4-one The title compound was obtained in the same manner in Example 2 from 1-bromo-2-[2-(4-diethylcarbamoylbenzyl)phenoxy]propane obtained in the same manner in Reference Example 1 and 1-phenyl-1,3,8-triazaspiro[4,5]decan-4-one. Yield: 37%.

$^1$H-NMR (CDCl$_3$) δ (ppm); 1.10 (3H, br-s), 1.21 (3H, br-s), 1.25 (3H, d, J=5 Hz), 1.65 (2H, m), 2.40–3.00 (8H, m), 3.24 (2H, br-s), 3.49 (2H, br-s), 3.94 (1H, d, J=15 Hz), 4.03 (1H, d, J=15 Hz), 4.59 (1H, m), 4.70 (2H, s), 6.75–6.90 (6H, m), 6.97 (1H, d, J=8 Hz), 7.09 (1H, d, J=8 Hz), 7.15–7.30 (6H, m)

MS (TSP); m/z 555 (MH$^+$)

Example 31

1-[2-[2-(4-Diisopropylcarbamoylbenzyl)phenoxy]ethyl]-4-(1,3-dihydro-2H-benzimidazol-2-on-1-yl)piperidine The title compound was obtained in the same manner in Example 1 from 1-[2-(4-diisopropylcarbamoylbenzyl)phenoxy]acetaldehyde obtained in the same manner in Reference Example 2 and 4-(1,3-dihydro-2H-benzimidazol-2-on-1-yl)piperidine. Yield: 25%.

$^1$H-NMR (CDCl$_3$) δ (ppm); 1.18 (6H, br-s), 1.45 (6H, br-s), 1.81 (2H, m), 2.38 (2H, m), 2.52 (2H, m), 2.89 (2H, m), 3.20 (2H, m), 3.52 (1H, m), 3.80 (1H, m), 3.99 (2H, s), 4.16 (2H, m), 4.40 (1H, m), 6.89 (2H, m), 7.05 (4H, m), 7.25 (6H, m), 9.58 (1H, s)

MS (TSP); m/z 555 (MH$^+$)

Example 32

8-[2-[2-(4-Diisopropylcarbamoylbenzyl)phenoxy]ethyl]-1-phenyl-1,3,8-triazaspiro[4,5]decan-4-one The title compound was obtained in the same manner in Example 1 from 1-[2-(4-diisopropylcarbamoylbenzyl)phenoxy]acetaldehyde obtained in the same manner in Reference Example 2 and 1-phenyl-1,3,8-triazaspiro[4,5]decan-4-one. Yield: 23%.

$^1$H-NMR (CDCl$_3$) δ (ppm); 1.16 (6H, br-s), 1.49 (6H, br-s), 1.71 (2H, m), 2.64 (2H, m), 2.89 (4H, m), 2.97 (2H, m), 3.51 (1H, m), 3.80 (1H, m), 3.99 (2H, s), 4.12 (2H, m), 4.73 (2H, s), 6.88 (6H, m), 7.09–7.26 (8H, m)

MS (TSP); m/z 569 (MH$^+$)

Example 33

1-[2-[2-[2-(4-Diethylcarbamoylphenyl)ethyl]phenoxy]ethyl]-4-(1,3-dihydro-2H-benzimidazol-2-on-1-yl)piperidine The title compound was obtained in the same manner in Example 1 from 1-[2-[2-(4-diethylcarbamoylphenyl)ethyl]phenoxy]acetaldehyde obtained in the same manner in Reference Example 2 and 4-(1,3-dihydro-2H-benzimidazol-2-on-1-yl)piperidine. Yield: 30%.

$^1$H-NMR (CDCl$_3$) δ (ppm); 1.07 (3H, br-s), 1.22 (3H, br-s), 1.81 (2H, m), 2.42 (4H, m), 2.94 (6H, m), 3.20 (4H, m), 3.52 (2H, br-s), 4.17 (2H, t, J=5 Hz), 4.39 (1H, m), 6.88 (2H, d, J=8 Hz), 7.03 (4H, m), 7.17–7.30 (6H, m), 9.86 (1H, s)

MS (TSP); m/z 541 (MH$^+$)

Example 34

8-[2-[2-[2-(4-Diethylcarbamoylphenyl)ethyl]phenoxy]ethyl]-1-phenyl-1,3,8-triazaspiro[4,5]decan-4-one The title compound was obtained in the same manner in Example 1 from 1-[2-[2-(4-diethylcarbamoylphenyl)ethyl]phenoxy]acetaldehyde obtained in the same manner in Reference Example 2 and 1-phenyl-1,3,8-triazaspiro[4,5]decan-4-one. Yield: 35%.

$^1$H-NMR (CDCl$_3$) δ (ppm); 1.09 (3H, br-s), 1.23 (3H, br-s), 1.71 (2H, m), 2.66 (2H, m), 2.86 (10H, m), 3.23 (2H, br-s), 3.52 (2H, br-s), 4.17 (2H, m), 4.70 (2H, s), 6.86 (5H, m), 7.06–7.28 (9H, m)

MS (TSP); m/z 555 (MH$^+$)

Example 35

1-[2-[2-(4-Diethylcarbamoylbenzyl)phenoxy]ethyl]-4-(1,3-dihydro-3-methyl-2H-benzimidazol-2-on-1-yl)piperidine The title compound was obtained in the same manner in Example 1 from the 1-[2-(4-diethylcarbamoylbenzyl)phenoxy]acetaldehyde obtained in Reference Example 2 and 4-(1,3-dihydro-3-methyl-2H-benzimidazol-2-on-1-yl)piperidine trifluoroacetate obtained in the same manner in Reference Example 3. Yield: 54%.

$^1$H-NMR (CDCl$_3$) δ (ppm); 1.10 (3H, br-s), 1.20 (3H, br-s),1.78 (2H, m), 2.30–2.60 (4H, m), 2.84 (2H, t, J=5 Hz), 3.14 (2H, d, J=12 Hz), 3.24 (2H, br-s), 3.41 (3H, s), 3.50 (2H, br-s), 4.00 (2H, s), 4.13 (2H, t, J=5 Hz), 4.39 (1H, m), 6.85–7.30 (12H, m)

MS (TSP); m/z 541 (MH$^+$)

Example 36

8-[2-[2-(4-Diethylcarbamoylbenzyl)phenoxy]ethyl]-3-methyl-1-phenyl-1,3,8-triazaspiro[4,5]decan-4-one The title compound was obtained in the same manner in Example 1 from the 1-[2-(4-diethylcarbamoylbenzyl)

phenoxy]acetaldehyde obtained in Reference Example 2 and 3-methyl-1-phenyl-1,3,8-triazaspiro[4,5]decan-4-one trifluoroacetate obtained in the same manner in Reference Example 3. Yield: 31%.

$^1$H-NMR (CDCl$_3$) δ (ppm); 1.10 (3H, br-s), 1.21 (3H, br-s), 1.64 (2H, d, J=14 Hz), 2.70 (2H, m), 2.85–3.10 (9H, m), 3.22 (2H, br-s), 3.48 (2H, br-s), 3.99 (2H, s), 4.15 (2H, m), 4.67 (2H, s), 6.80–6.95 (5H, m), 7.09 (1H, d, J=8 Hz), 7.15–7.30 (7H, m)

MS (TSP); m/z 555 (MH$^+$)

Example 37

1-[2-[2-(4-Diethylcarbamoylbenzyl)phenoxy]ethyl]-4-(2,3-dihydro-1H-indol-2-on-3-yl)piperidine The title compound was obtained in the same manner in Example 1 from the 1-[2-(4-diethylcarbamoylbenzyl) phenoxy]acetaldehyde obtained in Reference Example 2 and 4-(2,3-dihydro-1H-indol-2-on-3-yl)piperidine hydrochloride synthesized in accordance with the descriptions of Chem. Pharm. Bull. 1983, 31, 3186. Yield: 35%.

$^1$H-NMR (CDCl$_3$) δ (ppm); 1.11 (3H, br-s), 1.23 (3H, br-s), 1.68 (3H, m), 1.77 (1H, m), 2.11 (3H, m), 2.74 (2H, t, J=5 Hz), 2.94 (1H, d, J=12 Hz), 3.04 (1H, d, J=12 Hz), 3.26 (2H, br-s), 3.38 (1H, d, J=5 Hz), 3.54 (2H, br-s), 3.95 (2H, s), 4.05 (2H, t, J=5 Hz), 6.85 (4H, m), 6.98 (1H, t, J=8 Hz), 7.07 (1H, d, J=7 Hz), 7.15–7.26 (7H, m)

MS (FAB); m/z 526 (MH$^+$)

Example 38

1-[2-[2-(4-Diethylcarbamoylbenzyl)phenoxy]ethyl]-4-(1,2,3,4-tetrahydroquinolin-1-yl)piperidine The title compound was obtained in the same manner in Example 1 from the 1-[2-(4-diethylcarbamoylbenzyl) phenoxy]acetaldehyde obtained in Reference Example 2 and the 4-(1,2,3,4-tetrahydroquinolin-1-yl)piperidine trifluoroacetate obtained in Reference Example 4. Yield: 25%.

$^1$H-NMR (CDCl$_3$) δ (ppm); 1.11 (3H, br-s), 1.21 (3H, br-s), 1.74 (2H, m), 1.81–1.92 (4H, m), 2.27 (2H, t, J=7 Hz), 2.72 (2H, t, J=7 Hz), 2.81 (2H, t, J=5 Hz), 3.11 (2H, m), 3.20 (2H, t, J=7 Hz), 3.28 (2H, br-s), 3.52 (2H, br-s), 3.61 (1H, m), 4.00 (2H, s), 4.10 (2H, t, J=5 Hz), 6.55 (1H, t, J=8 Hz), 6.65 (1H, d, J=8 Hz), 6.88 (1H, t, J=8 Hz), 6.94 (1H, t, J=8 Hz), 7.04 (1H, t, J=8 Hz), 7.09 (1H, d, J=8 Hz), 7.24 (6H, m)

MS (FAB); m/z 526 (MH$^+$)

Example 39

1-[2-[2-(4-Diethylcarbamoylbenzyl)phenoxy]ethyl]-4-(1,2,3,4-tetrahydronaphthalen-1-yl)piperidine The title compound was obtained in the same manner in Example 1 from the 1-[2-(4-diethylcarbamoylbenzyl) phenoxy]acetaldehyde obtained in Reference Example 2 and 4-(1,2,3,4-tetrahydronaphthalen-1-yl)piperidine hydrochloride synthesized in accordance with the descriptions of Japanese Patent Laid-open Publication (Kokai) No. 11-189585. Yield: 39%.

$^1$H-NMR (CDCl$_3$) δ (ppm); 1.11 (3H, br-s), 1.22 (3H, br-s), 1.39 (2H, m), 1.58 (5H, m), 1.78 (1H, m), 1.92 (1H, m), 2.05 (2H, m), 2.26 (1H, m), 2.76 (4H, m), 3.01 (2H, m), 3.36 (2H, br-s), 3.51 (2H, br-s), 4.01 (2H, s), 4.24 (2H, m), 6.98 (2H, m), 7.37 (10H, m)

MS (FAB); m/z 525 (MH$^+$)

Example 40

1-[2-[2-(4-Diethylcarbamoylphenyl)phenoxy]ethyl]-4-(1,3-dihydro-2H-benzimidazol-2-on-1-yl) piperidine The title compound was obtained in the same manner in Example 1 from the 1-[2-(4-diethylcarbamoylphenyl) phenoxy]acetaldehyde obtained in Reference Example 5 and 4-(1,3-dihydro-2H-benzimidazol-2-on-1-yl)piperidine. Yield: 94%.

$^1$H-NMR (CDCl$_3$) δ (ppm); 1.15 (3H, br-s), 1.23 (3H, br-s), 1.77 (2H, d, J=12 Hz), 2.27 (2H, t, J=12 Hz), 2.47 (2H, q, J=12 Hz), 2.82 (2H, t, J=5 Hz), 3.09 (2H, d, J=12 Hz), 3.32 (2H, br-s), 3.55 (2H, br-s), 4.16 (2H, t, J=5 Hz), 4.34 (1H, m), 6.90–7.10 (4H, m), 7.25–7.55 (6H, m), 7.60 (2H, d, J=8 Hz), 9.44 (1H, s)

MS (ESI); m/z 513 (MH$^+$)

Example 41

8-[2-[2-(4-Diethylcarbamoylphenyl)phenoxy]ethyl]-1-phenyl-1,3,8-triazaspiro[4,5]decan-4-one The title compound was obtained in the same manner in Example 1 from the 1-[2-(4-diethylcarbamoylphenyl) phenoxy]acetaldehyde obtained in Reference Example 5 and 1-phenyl-1,3,8-triazaspiro[4,5]decan-4-one. Yield: 65%.

$^1$H-NMR (CDCl$_3$) δ (ppm); 1.13 (3H, br-s), 1.23 (3H, br-s), 1.67 (2H, d, J=12 Hz), 2.74 (2 H, dt, J=5 Hz, 12 Hz), 2.90–3.10 (6H, m), 3.31 (2H, br-s), 3.54 (2H, br-s), 4.21 (2H, t, J=5 Hz), 4.71 (2H, s), 6.80–6.95 (3H, m), 7.00–7.10 (2H, m), 7.20–7.40 (7H, m), 7.59 (2H, d, J=8 Hz)

MS (ESI); m/z 527 (MH$^+$)

Example 42

1-[2-[2-(4-Diethylcarbamoylbenzyl)phenoxy]ethyl]-4-(indan-1-yl)piperidine

The title compound was obtained in the same manner in Example 1 from the 1-[2-(4-diethylcarbamoylbenzyl) phenoxy]acetaldehyde obtained in Reference Example 2 and 4-(indan-1-yl)piperidine hydrochloride synthesized by the method described in Japanese Patent Unexamined Publication (Kokai) No. 11-189585. Yield: 49%.

$^1$H-NMR (CDCl$_3$) δ (ppm); 1.11 (3H, br-s), 1.22 (3H, br-s), 1.32–1.56 (2H, m), 1.67 (4H, m), 1.94 (1H, m), 2.00–2.12 (2H, m), 2.76 (2H, t, J=5 Hz), 2.80–2.94 (2H, m), 2.96–3.12 (3H, m), 3.26 (2H, br-s), 3.53 (2H, br-s), 3.96 (2H, s), 4.09 (2H, t, J=5 Hz), 6.86 (2H, m), 7.08 (1H, d, J=8 Hz), 7.12–7.27 (9H, m)

MS (FAB); m/z 511 (MH$^+$)

Example 43

1-[2-[3-(4-Diethylcarbamoylphenyl)phenoxy]ethyl]-4-(1,3-dihydro-2H-benzimidazol-2-on-1-yl) piperidine The title compound was obtained in the same manner in Example 1 from 1-[3-(4-diethylcarbamoylphenyl)phenoxy] acetaldehyde obtained in the same manner in Reference Example 5 and 4-(1,3-dihydro-2H-benzimidazol-2-on-1-yl) piperidine. Yield: 82%.

$^1$H-NMR (CDCl$_3$) δ (ppm); 1.16 (3H, br-s), 1.26 (3H, br-s), 1.84 (2H, d, J=12 Hz), 2.38 (2H, t, J=12 Hz), 2.53 (2H, q, J=12 Hz), 2.93 (2H, t, J=5 Hz), 3.21 (2H, d, J=12 Hz), 3.32 (2H, br-s), 3.57 (2H, br-s), 4.22 (2H, t, J=5 Hz), 4.41 (1H, m), 6.90–7.50 (10H, m), 7.61 (2H, d, J=8 Hz), 9.92 (1H, s)

MS (ESI); m/z 513 (MH$^+$)

Example 44

8-[2-[3-(4-Diethylcarbamoylphenyl)phenoxy]ethyl]-1-phenyl-1,3,8-triazaspiro[4,5]decan-4-one The title compound was obtained in the same manner in Example 1 from 1-[3-(4-diethylcarbamoylphenyl)phenoxy] acetaldehyde obtained in the same manner in Reference Example 5 and 1-phenyl-1,3,8-triazaspiro[4,5]decan-4-one. Yield: 44%.

$^1$H-NMR (CDCl$_3$) δ (ppm); 1.16 (3H, br-s), 1.26 (3H, br-s), 1.74 (2H, d, J=14 Hz), 2.70 (2H, m), 2.85–3.10 (6H, m), 3.32 (2H, br-s), 3.56 (2H, br-s), 4.21 (2H, t, J=5 Hz), 4.73 (2H, s), 6.80–7.00 (4H, m), 7.10–7.20 (2H, m), 7.25–7.45 (6H, m), 7.61 (2H, d, J=8 Hz)

MS (ESI); m/z 527 (MH$^+$)

Example 45

1-[2-[3-(3-Diethylcarbamoylphenyl)phenoxy]ethyl]-4-(1,3-dihydro-2H-benzimidazol-2-on-1-yl) piperidine The title compound was obtained in the same manner in Example 1 from 1-[3-(3-diethylcarbamoylphenyl)phenoxy] acetaldehyde obtained in the same manner in Reference Example 5 and 4-(1,3-dihydro-2H-benzimidazol-2-on-1-yl) piperidine. Yield: 70%.

$^1$H-NMR (CDCl$_3$) δ (ppm); 1.12 (3H, br-s), 1.27 (3H, br-s), 1.84 (2H, d, J=12 Hz), 2.37 (2H, t, J=12 Hz), 2.53 (2H, q, J=12 Hz), 2.92 (2H, t, J=5 Hz), 3.20 (2H, d, J=12 Hz), 3.30 (2H, br-s), 3.56 (2H, br-s), 4.21 (2H, t, J=5 Hz), 4.41 (1H, m), 6.90–7.50 (10H, m), 7.65–7.75 (2H, m), 10.01 (1H, s)

MS (ESI); m/z 513 (MH$^+$)

Example 46

8-[2-[3-(3-Diethylcarbamoylphenyl)phenoxy]ethyl]-1-phenyl-1,3,8-triazaspiro[4,5]decan-4-one The title compound was obtained in the same manner in Example 1 from 1-[3-(3-diethylcarbamoylphenyl)phenoxy] acetaldehyde obtained in the same manner in Reference Example 5 and 1-phenyl-1,3,8-triazaspiro[4,5]decan-4-one. Yield: 66%.

$^1$H-NMR (CDCl$_3$) δ (ppm); 1.12 (3H, br-s), 1.27 (3H, br-s), 1.74 (2H, d, J=14 Hz), 2.70 (2H, m), 2.85–3.10 (6H, m), 3.29 (2H, br-s), 3.56 (2H, br-s), 4.20 (2H, t, J=5 Hz), 4.72 (2H, s), 6.80–7.00 (4H, m), 7.10–7.20 (3H, m), 7.25–7.50 (5H, m), 7.65–7.75 (2H, m)

MS (ESI); m/z 527 (MH$^+$)

Example 47

1-[2-[2-(4-Diethylcarbamoylbenzyl)phenoxy]ethyl]-4-(1H-benzimidazol-1-yl)piperidine The title compound was obtained in the same manner in Example 1 from the 1-[2-(4-diethylcarbamoylbenzyl) phenoxy]acetaldehyde obtained in Reference Example 2 and the 4-(1H-benzimidazol-1-yl)piperidine trifluoroacetate obtained in Reference Example 6. Yield: 60%.

$^1$H-NMR (CDCl$_3$) δ (ppm); 1.09 (3H, br-s), 1.21 (3H, br-s), 2.15 (4H, m), 2.34 (2H, m), 2.86 (2H, t, J=5 Hz), 3.16 (2H, m), 3.25 (2H, br-s), 3.51 (2H, br-s), 4.01 (2H, s), 4.13 (2H, t, J=5 Hz), 4.22 (1H, m), 6.90 (2H, m), 7.12 (1H, d, J=8 Hz), 7.20–7.30 (8H, m), 7.46 (1H, m), 8.02 (1H, s)

MS (FAB); m/z 511 (MH$^+$)

Example 48

1-[2-[2-(4-Diethylcarbamoylbenzyl)phenoxy]ethyl]-4-(1,2,3,4-tetrahydroquinolin-2-on-1-yl)piperidine The title compound was obtained in the same manner in Example 1 from the 1-[2-(4-diethylcarbamoylbenzyl) phenoxy]acetaldehyde obtained in Reference Example 2 and 4-(1,2,3,4-tetrahydroquinolin-2-on-1-yl)piperidine trifluoroacetate obtained in the same manner in Reference Example 6. Yield: 50%.

$^1$H-NMR (CDCl$_3$) δ (ppm); 1.10 (3H, br-s), 1.21 (3H, br-s), 1.70 (2H, m), 2.29 (2H, m), 2.57 (2H, m), 2.66 (2H, m), 2.82 (4H, m), 3.11 (2H, m), 3.25 (2H, br-s), 3.53 (2H, br-s), 3.99 (2H, s), 4.12 (2H, t, J=5 Hz), 4.33 (1H, m), 6.88 (2H, m), 7.00 (1H, m), 7.09 (1H, d, J=8 Hz), 7.14–7.28 (8H, m)

MS (FAB); m/z 540 (MH$^+$)

Example 49

4-Acetyl-1-[2-[2-(4-diethylcarbamoylbenzyl) phenoxy]ethyl]-4-phenylpiperidine

The title compound was obtained in the same manner in Example 1 from the 1-[2-(4-diethylcarbamoylbenzyl) phenoxy]acetaldehyde obtained in Reference Example 2 and 4-acetyl-4-phenylpiperidine hydrochloride. Yield: 71%.

$^1$H-NMR (CDCl$_3$) δ (ppm); 1.10 (3H, br-s), 1.19 (3H, br-s), 1.91 (3H, s), 2.05 (2H, m), 2.41 (4H, m), 2.74 (2H, t, J=5 Hz), 2.80 (2H, m), 3.26 (2H, br-s), 3.51 (2H, br-s), 3.97 (2H, s), 4.02 (2H, t, J=5 Hz), 6.84 (1H, d, J=8 Hz), 6.88 (1H, t, J=8 Hz), 7.09 (1H, d, J=8 Hz), 7.16–7.37 (10H, m)

MS (FAB); m/z 513 (MH$^+$)

Example 50

1-[2-[2-(3-Diethylcarbamoylphenyl)phenoxy]ethyl]-4-(1,3-dihydro-2H-benzimidazol-2-on-1-yl) piperidine The title compound was obtained in the same manner in Example 1 from 1-[2-(3-diethylcarbamoylphenyl)phenoxy] acetaldehyde obtained in the same manner in Reference Example 5 and 4-(1,3-dihydro-2H-benzimidazol-2-on-1-yl) piperidine. Yield: 48%.

$^1$H-NMR (CDCl$_3$) δ (ppm); 1.13 (3H, br-s), 1.23 (3H, br-s), 1.75 (2H, m), 2.24 (2H, t, J=12 Hz), 2.44 (2H, q, J=12 Hz), 2.79 (2H, t, J=5 Hz), 3.05 (2H, d, J=12 Hz), 3.32 (2H, br-s), 3.55 (2H, br-s), 4.14 (2H, t, J=5 Hz), 4.33 (1H, m), 6.95–7.15 (4H, m), 7.20–7.45 (6H, m), 7.53 (1H, s), 7.64 (1H, d, J=8 Hz), 9.67 (1H, s)

MS (FAB); m/z 513 (MH$^+$)

Example 51

8-[2-[2-(3-Diethylcarbamoylphenyl)phenoxy]ethyl]-1-phenyl-1,3,8-triazaspiro[4,5]decan-4-one The title compound was obtained in the same manner in Example 1 from 1-[2-(3-diethylcarbamoylphenyl)phenoxy]

acetaldehyde obtained in the same manner in Reference Example 5 and 1-phenyl-1,3,8-triazaspiro[4,5]decan-4-one. Yield: 62%.

$^1$H-NMR (CDCl$_3$) δ (ppm); 1.12 (3H, br-s), 1.26 (3H, br-s), 1.67 (2H, m), 2.64 (2H, m), 2.75–3.00 (6H, m), 3.32 (2H, br-s), 3.54 (2H, br-s), 4.12 (2H, t, J=5 Hz), 4.72 (2H, s), 6.80–6.95 (3H, m), 7.00–7.10 (2H, m), 7.20–7.40 (7H, m), 7.50 (1H, s), 7.67 (1H, d, J=8 Hz)

MS (FAB); m/z 527 (MH$^+$)

Example 52

1-[1-[2-(4-Diethylcarbamoylbenzyl)phenoxymethyl]ethyl]-4-(1,3-dihydro-2H-benzimidazol-2-on-1-yl)piperidine The title compound was obtained in the similar manner to that of Example 2 from 1-[2-(4-diethylcarbamoylbenzyl)phenoxymethyl]-1-methanesulfonyloxyethane obtained in the similar manner to that of Reference Example 1 and 4-(1,3-dihydro-2H-benzimidazol-2-on-1-yl)piperidine. Yield: 48%.

$^1$H-NMR (CDCl$_3$) δ (ppm); 1.00–1.30 (9H, m), 1.70–1.85 (2H, m), 2.30–2.65 (4H, m), 3.00–3.15 (3H, m), 3.25 (2H, br-s), 3.49 (2H, br-s), 3.90 (1H, dd, J=12 Hz, 7 Hz), 4.02 (2H, s), 4.09 (1H, dd, J=12 Hz, 5 Hz), 4.34 (1H, m), 6.85–6.95 (2H, m), 7.00–7.15 (4H, m), 7.20–7.35 (6H, m), 9.34 (1H, s)

MS (APCI); m/z 541 (MH$^+$)

Example 53

4-(1H-Benzotriazol-1-yl)-1-[2-[2-(4-diethylcarbamoylbenzyl)phenoxy]ethyl]piperidine The title compound was obtained in the same manner in Example 1 from the 1-[2-(4-diethylcarbamoylbenzyl)phenoxy]acetaldehyde obtained in Reference Example 2 and 4-(1H-benzotriazol-1-yl)piperidine obtained in the same manner in Reference Example 6. Yield: 76%.

$^1$H-NMR (CDCl$_3$) δ (ppm); 1.09 (3H, br-s), 1.20 (3H, br-s), 2.15 (2H, m), 2.36–2.54 (4H, m), 2.87 (2H, t, J=5 Hz), 3.18 (2H, m), 3.25 (2H, br-s), 3.51 (2H, br-s), 4.01 (2H, s), 4.14 (2H, t, J=5 Hz), 4.71 (1H, m), 6.90 (2H, m), 7.12 (1H, d, J=8 Hz), 7.20–7.29 (5H, m), 7.36 (1H, t, J=8 Hz), 7.46 (1H, t, J=8 Hz), 7.63 (1H, d, J=8 Hz), 8.06 (1H, d, J=8 Hz)

MS (FAB); m/z 512 (MH$^+$)

Example 54

1-[2-[2-(4-Diethylcarbamoylbenzyl)phenoxy]ethyl]-4-(2,3-dihydro-1H-indol-1-yl)piperidine The title compound was obtained in the same manner in Example 1 from the 1-[2-(4-diethylcarbamoylbenzyl)phenoxy]acetaldehyde obtained in Reference Example 2 and 4-(2,3-dihydro-1H-indol-1-yl)piperidine in the same manner in Reference Example 4. Yield: 47%.

$^1$H-NMR (CDCl$_3$) δ (ppm); 1.11 (3H, br-s), 1.21 (3H, br-s), 1.83 (4H, m), 2.36 (2H, m), 2.94 (4H, m), 3.25 (2H, br-s), 3.36 (2H, t, J=5 Hz), 3.51 (4H, m), 3.99 (2H, s), 4.12 (2H, m), 4.18 (1H, m), 6.46 (1H, d, J=8 Hz), 6.61 (1H, t, J=8 Hz), 6.87 (1H, d, J=8 Hz), 6.93 (1H, t, J=8 Hz), 7.04 (2H, m), 7.12 (1H, d, J=8 Hz), 7.18–7.28 (5H, m)

MS (TSP); m/z 512 (MH$^+$)

Example 55

8-[1-[2-(4-Diethylcarbamoylbenzyl)phenoxymethyl]ethyl]-1-phenyl-1,3,8-triazaspiro[4,5]decan-4-one The title compound was obtained in the similar manner to that of Example 2 from 1-[2-(diethylcarbamoylbenzyl)phenoxymethyl]-1-methanesulfonyloxyethane obtained in the similar manner to that of Reference Example 1 and 1-phenyl-1,3,8-triazaspiro[4,5]decan-4-one. Yield: 12%.

1H-NMR (CDCl$_3$) δ (ppm); 1.00–1.30 (9H, m), 1.67 (2H, d, J=14 Hz), 2.63 (2H, m), 2.79 (2H, m), 3.05–3.30 (5H, m), 3.50 (2H, br-s), 3.80–4.15 (4H, m), 4.71 (2H, s), 6.70–7.00 (6H, m), 7.05–7.30 (8H, m)

MS (TSP); m/z 555 (MH$^+$)

Example 56

4-(1H-Benzimidazol-1-yl)-1-[1-[2-(4-diethylcarbamoylbenzyl)phenoxymethyl]ethyl]piperidine The title compound was obtained in the similar manner to that of Example 2 from 1-[2-(4-diethylcarbamoylbenzyl)phenoxymethyl]-1-methanesulfonyloxyethane obtained in the similar manner to that of Reference Example 1 and 4-(1H-benzimidazol-1-yl)piperidine trifluoroacetate. Yield: 27%.

$^1$H-NMR (CDCl$_3$) δ (ppm); 1.00–1.30 (9H, m), 2.14 (4H, m), 2.55 (2H, m), 3.07 (3H, m), 3.23 (2H, br-s), 3.50 (2H, br-s), 3.85–4.25 (5H, m), 6.85–6.95 (2H, m), 7.10–7.35 (8H, m), 7.44 (1H, m), 7.80 (1H, m), 8.01 (1H, s)

MS (ESI); m/z 525 (MH$^+$)

Example 57

1-[2-[2-(4-Diethylcarbamoylbenzyl)phenoxy]ethyl]-4-(6-fluoro-1,2-benzisothiazol-3-yl)piperidine The title compound was obtained in the same manner in Example 1 from the 1-[2-(4-diethylcarbamoylbenzyl)phenoxy]acetaldehyde obtained in Reference Example 2 and 4-(6-fluoro-1,2-benzisothiazol-3-yl)piperidine synthesized in accordance with the descriptions of WO98/42710. Yield: 12%.

$^1$H-NMR (CDCl$_3$) δ (ppm); 1.10 (3H, br-s), 1.21 (3H, br-s), 2.01 (2H, m), 2.11 (2H, m), 2.33 (2H, m), 2.77 (2H, t, J=5 Hz), 3.14 (2H, m), 3.20 (1H, m), 3.25 (2H, br-s), 3.51 (2H, br-s), 4.00 (2H, s), 4.14 (2H, t, J=5 Hz), 6.89 (2H, m), 7.09–7.29 (7H, m), 7.57 (1H, m), 7.96 (1H, m)

MS (TSP); m/z 546 (MH$^+$)

Example 58

1-[2-[2-(4-Diethylcarbamoylbenzyl)phenoxy]ethyl]-4-(6-fluoro-1,2-benzisoxazol-3-yl)piperidine The title compound was obtained in the same manner in Example 1 from the 1-[2-(4-diethylcarbamoylbenzyl)phenoxy]acetaldehyde obtained in Reference Example 2 and 4-(6-fluoro-1,2-benzisoxazol-3-yl)piperidine synthesized in accordance with the descriptions of EP428437. Yield: 31%.

$^1$H-NMR (CDCl$_3$) δ (ppm); 1.09 (3H, br-s), 1.21 (3H, br-s), 2.06 (4H, m), 2.34 (2H, m), 2.86 (2H, t, J=5 Hz), 3.08 (1H, m), 3.14 (2H, m), 3.25 (2H, br-s), 3.52 (2H, br-s), 4.00 (2H, s), 4.15 (2H, t, J=5 Hz), 6.90 (2H, m), 7.04–7.13 (2H, m), 7.19–7.29 (6H, m), 7.71 (1H, m)

MS (TSP); m/z 530 (MH$^+$)

Example 59

1-[2-[2-(4-Diethylcarbamoylbenzyl)phenoxy]ethyl]-4-(1H-indol-3-yl)piperidine

The title compound was obtained in the same manner in Example 1 from the 1-[2-(4-diethylcarbamoylbenzyl)

phenoxy]acetaldehyde obtained in Reference Example 2 and 4-(1H-indol-3-yl)piperidine hydrochloride synthesized in accordance with the descriptions of J. Org. Chem., 1975, 40, 2525 and Helv. Chim. Acta, 1968, 51, 260. Yield: 30%.

$^1$H-NMR (CDCl$_3$) δ (ppm); 1.08 (3H, br-s), 1.21 (3H, br-s), 1.85 (2H, m), 2.06 (2H, m), 2.34 (2H, m), 2.86 (2H, t, J=5 Hz), 3.13 (2H, m), 3.24 (2H, br-s), 3.52 (2H, br-s), 4.01 (2H, s), 4.10 (1H, m), 4.16 (2H, t, J=5 Hz), 6.89 (1H, d, J=8 Hz), 6.93 (1H, m), 7.07–7.29 (9H, m), 7.35 (1H, d, J=8 Hz), 7.64 (1H, d, J=8 Hz), 8.14 (1H, s)

MS (TSP); m/z 510 (MH$^+$)

Example 60

1'-[2-[2-(4-Diethylcarbamoylbenzyl)phenoxy]ethyl]-2,3-dihydrospiro[1H-indene-1,4'-piperidine]

The title compound was obtained in the same manner in Example 1 from the 1-[2-(4-diethylcarbamoylbenzyl)phenoxy]acetaldehyde obtained in Reference Example 2 and 2,3-dihydrospiro[1H-indene-1,4'-piperidine] synthesized in accordance with the descriptions of J. Med. Chem. 1992, 35, 2033. Yield: 49%.

$^1$H-NMR (CDCl$_3$) δ (ppm); 1.09 (3H, br-s), 1.20 (3H, br-s), 1.55 (2H, m), 1.95 (2H, m), 2.02 (2H, t, J=7 Hz), 2.35 (2H, m), 2.85 (2H, t, J=5 Hz), 2.90 (2H, t, J=7 Hz), 2.98 (2H, m), 3.25 (2H, br-s), 3.51 (2H, br-s), 4.00 (2H, s), 4.16 (2H, t, J=5 Hz), 6.90 (1H, d, J=8 Hz), 7.10 (1H, d, J=8 Hz), 7.16–7.28 (10H, m)

MS (TSP); m/z 497 (MH$^+$)

Example 61

(R)-1-[1-[2-(4-Diethylcarbamoylbenzyl)phenoxymethyl]ethyl]-4-(1,3-dihydro-2H-benzimidazol-2-on-1-yl)piperidine The title compound was obtained in the similar manner to that of Example 2 from (S)-1-[2-(4-diethylcarbamoylbenzyl)phenoxymethyl]-1-methanesulfonyloxyethane obtained in the similar manner to that of Reference Example 1 and 4-(1,3-dihydro-2H-benzimidazol-2-on-1-yl)piperidine. Yield: 68%.

$^1$H-NMR (CDCl$_3$) δ (ppm); 1.00–1.30 (9H, m), 1.80–1.90 (2H, m), 2.30–2.65 (4H, m), 3.00–3.15 (3H, m), 3.25 (2H, br-s), 3.49 (2H, br-s), 3.90 (1H, dd, J=12 Hz, 7 Hz), 4.02 (2H, s), 4.09 (1H, dd, J=12 Hz, 5 Hz), 4.34 (1H, m), 6.85–6.95 (2H, m), 7.00–7.15 (4H, m), 7.20–7.35 (6H, m), 9.78 (1H, s)

MS (TSP); m/z 541 (MH$^+$)

[a]$_D^{22}$+3.3° (c 1.02, CH$_2$Cl$_2$)

Example 62

(S)-1-[1-[2-(4-Diethylcarbamoylbenzyl)phenoxymethyl]ethyl]-4-(1,3-dihydro-2H-benzimidazol-2-on-1-yl)piperidine The title compound was obtained in the similar manner to that of Example 2 from (R)-1-bromo-1-[2-(4-diethylcarbamoylbenzyl)phenoxymethyl]ethane obtained in the similar manner to that of Reference Example 1 and 4-(1,3-dihydro-2H-benzimidazol-2-on-1-yl)piperidine. Yield: 69%.

$^1$H-NMR (CDCl$_3$) δ (ppm); 1.00–1.30 (9H, m), 1.80–1.90 (2H, m), 2.30–2.65 (4H, m), 3.00–3.15 (3H, m), 3.25 (2H, br-s), 3.49 (2H, br-s), 3.90 (1H, dd, J=12 Hz, 7 Hz), 4.02 (2H, s), 4.09 (1H, dd, J=12 Hz, 5 Hz), 4.34 (1H, m), 6.85–6.95 (2H, m), 7.00–7.15 (4H, m), 7.20–7.35 (6H, m), 9.74 (1H, s)

MS (TSP); m/z 541 (MH$^+$)

Example 63

1-[2-[2-(4-Diethylcarbamoylbenzyl)phenoxy]ethyl]-4-(1,2,3,4-tetrahydroquinazolin-2-on-1-yl)piperidine The title compound was obtained in the same manner in Example 1 from the 1-[2-(4-diethylcarbamoylbenzyl)phenoxy]acetaldehyde obtained in Reference Example 2 and the 4-(1,2,3,4-tetrahydroquinazolin-2-on-1-yl)piperidine trifluoroacetate obtained in Reference Example 7. Yield: 26%.

$^1$H-NMR (CDCl$_3$) δ (ppm); 1.10 (3H, br-s), 1.21 (3H, br-s), 1.78 (2H, m), 2.31 (2H, m), 2.74 (2H, m), 2.85 (2H, t, J=5 Hz), 3.13 (2H, m), 3.26 (2H, br-s), 3.52 (2H, br-s), 3.99 (2H, s), 4.09 (1H, m), 4.13 (2H, t, J=5 Hz), 4.27 (2H, s), 5.13 (1H, m), 6.89 (2H, m), 6.98 (1H, t, J=8 Hz), 7.08 (2H, m), 7.14 (1H, d, J=8 Hz), 7.19–7.29 (6H, m)

MS (TSP); m/z 541 (MH$^+$)

Example 64

1'-[2-[2-(4-Diethylcarbamoylbenzyl)phenoxy]ethyl]-2,3-dihydrospiro-[isoquinoline-4(1H),4'-piperidin]-1-one The title compound was obtained in the same manner in Example 1 from the 1-[2-(4-diethylcarbamoylbenzyl)phenoxy]acetaldehyde obtained in Reference Example 2 and 2,3-dihydrospiro[isoquinoline-4(1H),4'-piperidin]-1-one synthesized in accordance with the descriptions of WO94/13696. Yield: 74%.

$^1$H-NMR (CDCl$_3$) δ (ppm); 1.09 (3H, br-s), 1.22 (3H, br-s), 1.78 (2H, m), 2.07 (2H, m), 2.25 (2H, m), 2.79 (2H, t, J=5 Hz), 2.87 (2H, m), 3.24 (2H, br-s), 3.49 (2H, s), 3.54 (2H, br-s), 4.00 (2H, s), 4.11 (2H, t, J=5 Hz), 6.71 (1H, s), 6.86 (1H, d, J=8 Hz), 6.91 (1H, t, J=8 Hz), 7.14 (1H, d, J=8 Hz), 7.20 (3H, m), 7.27 (2H, m), 7.35 (1H, t, J=8 Hz), 7.43 (1H, d, J=8 Hz), 7.51 (1H, t, J=8 Hz), 8.09 (1H, d, J=8 Hz)

MS (TSP); m/z 526 (MH$^+$)

Example 65

1-[2-[2-(4-Diethylcarbamoylbenzyl)phenoxy]ethyl]spiro[piperidine-4,4'(1'H)-quinolin]-2'(3'H)-one The title compound was obtained in the same manner in Example 1 from the 1-[2-(4-diethylcarbamoylbenzyl)phenoxy]acetaldehyde obtained in Reference Example 2 and spiro[piperidine-4,4'(1'H)-quinolin]-2'(3'H)-one synthesized in accordance with the descriptions of WO94/13696. Yield: 51%.

$^1$H-NMR (CDCl$_3$) δ (ppm); 1.09 (3H, br-s), 1.21 (3H, br-s), 1.70 (2H, m), 2.06 (2H, m), 2.51 (2H, m), 2.69 (2H, s), 2.88 (4H, m), 3.26 (2H, br-s), 3.52 (2H, br-s), 3.99 (2H, s), 4.12 (2H, t, J=5 Hz), 6.77 (1H, d, J=8 Hz), 6.89 (2H, m), 7.08 (2H, m), 7.18–7.28 (7H, m), 7.37 (1H, d, J=8 Hz)

MS (TSP); m/z 526 (MH$^+$)

Example 66

1'-[2-[2-(4-Diethylcarbamoylbenzyl)phenoxy]ethyl]spiro[1H-indene-1,4'-piperidin]-3(2H)-one The title compound was obtained in the same manner in Example 1 from the 1-[2-(4-diethylcarbamoylbenzyl)phenoxy]acetaldehyde obtained in Reference Example 2 and spiro[1H-indene-1,4'-piperidin]-3(2H)-one synthesized in accordance with the descriptions of WO94/13696. Yield: 50%.

¹H-NMR (CDCl₃) δ (ppm); 1.09 (3H, br-s), 1.21 (3H, br-s), 1.52 (2H, m), 2.15 (2H, m), 2.26 (2H, m), 2.59 (2H, s), 2.86 (2H, t, J=5 Hz), 3.07 (2H, m), 3.25 (2H, br-s), 3.50 (2H, br-s), 4.00 (2H, s), 4.15 (2H, t, J=5 Hz), 6.90 (2H, m), 7.11 (1H, d, J=8 Hz), 7.19–7.28 (5H, m), 7.40 (1H, t, J=8 Hz), 7.55 (1H, d, J=8 Hz), 7.64 (1H, t, J=8 Hz), 7.73 (1H, d, J=8 Hz)

MS (TSP); m/z 511 (MH⁺)

Example 67

1-[2-[2-(4-Diethylcarbamoylbenzyl)phenoxy]ethyl]-4-(3,3-dimethyl-2,3-dihydro-1H-indol-2-on-1-yl)piperidine The title compound was obtained in the same manner in Example 1 from the 1-[2-(4-diethylcarbamoylbenzyl)phenoxy]acetaldehyde obtained in Reference Example 2 and 4-(3,3-dimethyl-2,3-dihydro-1H-indol-2-on-1-yl)piperidine trifluoroacetate obtained in the same manner in Reference Example 6. Yield: 78%.

¹H-NMR (CDCl₃) δ (ppm); 1.10 (3H, br-s), 1.22 (3H, br-s), 1.35 (6H, s), 1.69 (2H, m), 2.30 (2H, m), 2.46 (2H, m), 2.83 (2H, t, J=5 Hz), 3.12 (2H, m), 3.26 (2H, br-s), 3.52 (2H, br-s), 4.00 (2H, s), 4.12 (2H, t, J=5 Hz), 4.33 (1H, m), 6.90 (2H, m), 7.03 (1H, t, J=8 Hz), 7.10 (1H, d, J=8 Hz), 7.18–7.28 (8H, m)

MS (TSP); m/z 554 (MH⁺)

Example 68

1-[2-[2-(4-Diethylcarbamoylbenzyl)phenoxy]ethyl]-4-phenylpiperidine

The title compound was obtained in the same manner in Example 1 from the 1-[2-(4-diethylcarbamoylbenzyl)phenoxy]acetaldehyde obtained in Reference Example 2 and the 4-phenylpiperidine hydrochloride obtained in Reference Example 8. Yield: 58%.

¹H-NMR (CDCl₃) δ (ppm); 1.10 (3H, br-s), 1.21 (3H, br-s), 1.82 (4H, m), 2.24 (2H, m), 2.50 (1H, m), 2.83 (2H, t, J=5 Hz), 3.11 (2H, m), 3.26 (2H, br-s), 3.52 (2H, br-s), 4.00 (2H, s), 4.13 (2H, t, J=5 Hz), 6.84–6.96 (3H, m), 7.10 (1H, d, J=8 Hz), 7.16–7.32 (9H, m)

MS (TSP); m/z 471 (MH⁺)

Example 69

1-[2-[2-(4-Diethylcarbamoylbenzyl)phenoxy]ethyl]-4-(1H-indol-1-yl)piperidine The title compound was obtained in the same manner in Example 1 from the 1-[2-(4-diethylcarbamoylbenzyl)phenoxy]acetaldehyde obtained in Reference Example 2 and 4-(1H-indol-1-yl)piperidine hydrochloride synthesized in accordance with the descriptions of Syn. Commun. 1988, 18, 265. Yield: 76%.

¹H-NMR (CDCl₃) δ (ppm); 1.09 (3H, br-s), 1.20 (3H, br-s), 2.08 (4H, m), 2.36 (2H, m), 2.86 (2H, t, J=5 Hz), 3.16 (2H, d, J=12 Hz), 3.23 (2H, br-s), 3.51 (2H, br-s), 4.00 (2H, s), 4.13 (2H, t, J=5 Hz), 4.25 (1H, m), 6.51 (1H, d, J=3 Hz), 6.80–7.00 (2H, m), 7.10 (2H, m), 7.15–7.30 (7H, m), 7.38 (1H, d, J=8 Hz), 7.62 (1H, d, J=8 Hz)

MS (TSP); m/z 510 (MH⁺)

Example 70

1'-[2-[2-(4-Diethylcarbamoylbenzyl)phenoxy]ethyl]spiro[3H-indole-3,4'-piperidin]-2(1H)-one The title compound was obtained in the same manner in Example 1 from the 1-[2-(4-diethylcarbamoylbenzyl)phenoxy]acetaldehyde obtained in Reference Example 2 and the spiro[3H-indole-3,4'-piperidine]-2(1H)-one hydrochloride obtained in Reference Example 9. Yield: 50%.

¹H-NMR (CDCl₃) δ (ppm); 1.10 (3H, br-s), 1.20 (3H, br-s), 1.94 (4H, m), 2.85 (2H, m), 2.96 (2H, t, J=5 Hz), 3.08 (2H, m), 3.26 (2H, br-s), 3.50 (2H, br-s), 4.00 (2H, s), 4.18 (2H, t, J=5 Hz), 6.80–6.90 (3H, m), 7.00–7.15 (2H, m), 7.15–7.30 (6H, m), 7.35 (1H, d, J=8 Hz), 7.77 (1H, br-s)

MS (TSP); m/z 512 (MH⁺)

Example 71

1'-[2-[2-(4-Diethylcarbamoylbenzyl)phenoxy]ethyl]spiro[1H-indene-1,4'-piperidine]

The title compound was obtained in the same manner in Example 1 from the 1-[2-(4-diethylcarbamoylbenzyl)phenoxy]acetaldehyde obtained in Reference Example 2 and spiro[1H-indene-1,4'-piperidine] synthesized in accordance with the descriptions of J. Med. Chem., 1992, 35, 2033. Yield: 59%.

¹H-NMR (CDCl₃) δ (ppm); 1.09 (3H, br-s), 1.20 (3H, br-s), 1.35 (2H, d, J=12 Hz), 2.20 (2H, td, J=12 Hz, 3 Hz), 2.52 (2H, t, J=12 Hz), 2.92 (2H, t, J=5 Hz), 3.09 (2H, d, J=12 Hz), 3.23 (2H, br-s), 3.50 (2H, br-s), 4.00 (2H, s), 4.18 (2H, t, J=5 Hz), 6.75 (1H, d, J=6 Hz), 6.80–6.95 (3H, m), 7.05–7.40 (10H, m)

MS (TSP); m/z 495 (MH⁺)

Example 72

1-[2-[2-(4-Diethylcarbamoylbenzyl)phenoxy]ethyl]-4-(2-methyl-1H-benzimidazol-1-yl)piperidine The title compound was obtained in the same manner in Example 1 from the 1-[2-(4-diethylcarbamoylbenzyl)phenoxy]acetaldehyde obtained in Reference Example 2 and 4-(2-methyl-1H-benzimidazol-1-yl)piperidine trifluoroacetate obtained in the same manner in Reference Example 6. Yield: 28%.

¹H-NMR (CDCl₃) δ (ppm); 1.08 (3H, br-s), 1.20 (3H, br-s), 1.84 (2H, m), 2.30 (2H, m), 2.65 (3H, s), 2.75 (2H, m), 2.86 (2H, t, J=5 Hz), 3.17 (2H, m), 3.24 (2H, br-s), 3.50 (2H, br-s), 4.01 (2H, s), 4.15 (2H, t, J=5 Hz), 4.18 (1H, m), 6.91 (2H, m), 7.11–7.27 (8H, m), 7.58 (1H, m), 7.68 (1H, m)

MS (TSP); m/z 525 (MH⁺)

Example 73

1-[2-[2-(4-Diethylcarbamoylbenzyl)phenoxy]ethyl]-4-(3,4-dihydro-2H-1,4-benzoxazin-3-on-4-yl)piperidine The title compound was obtained in the same manner in Example 1 from the 1-[2-(4-diethylcarbamoylbenzyl)phenoxy]acetaldehyde obtained in Reference Example 2 and the 4-(3,4-dihydro-2H-1,4-benzoxazin-3-on-4-yl)piperidine trifluoroacetate obtained in Reference Example 10. Yield: 66%.

¹H-NMR (CDCl₃) δ (ppm); 1.10 (3H, br-s), 1.21 (3H, br-s), 1.74 (2H, m), 2.28 (2H, m), 2.65 (2H, m), 2.82 (2H, t, J=5 Hz), 3.12 (2H, m), 3.26 (2H, br-s), 3.53 (2H, br-s), 3.99 (2H, s), 4.11 (2H, t, J=5 Hz), 4.37 (1H, m), 4.50 (2H, s), 6.88 (2H, m), 7.00 (2H, s), 7.10 (1H, d, J=8 Hz), 7.17–7.28 (7H, m)

MS (FAB); m/z 542 (MH⁺)

Example 74

1-[2-[2-(4-Diethylcarbamoylbenzyl)phenoxy]ethyl]-4-(1H-imidazol-1-yl)piperidine The title compound was obtained in the same manner in Example 2 from 1-bromo-2-[2-(4-diethylcarbamoylbenzyl)

phenoxy]ethane obtained in the same manner in Reference Example 1 and 4-(1H-imidazol-1-yl)piperidine trifluoroacetate obtained in the same manner in Reference Example 6. Yield: 53%.

$^1$H-NMR (CDCl$_3$) δ (ppm); 1.10 (3H, br-s), 1.22 (3H, br-s), 1.99 (4H, m), 2.11 (2H, m), 2.82 (2H, t, J=5 Hz), 3.05 (2H, m), 3.28 (2H, br-s), 3.52 (2H, br-s), 3.92 (1H, m), 3.99 (2H, s), 4.09 (2H, t, J=5 Hz), 6.86 (1H, d, J=8 Hz), 6.91 (2H, t, J=8 Hz), 6.99 (1H, s), 7.05 (1H, s), 7.11 (1H, d, J=8 Hz), 7.24 (4H, m), 7.57 (1H, s)

MS (EI); m/z 554 (M$^+$)

Example 75

1-[1-[2-(4-Diethylcarbamoylbenzyl)phenoxymethyl] propyl]-4-(1,3-dihydro-2H-benzimidazol-2-on-1-yl) piperidine The title compound was obtained in the similar manner to that of Example 2 from 1-[2-(4-diethylcarbamoylbenzyl) phenoxymethyl]-1-methanesulfonyloxypropane obtained in the similar manner to that of Reference Example 1 and 4-(1,3-dihydro-2H-benzimidazol-2-on-1-yl)piperidine. Yield: 32%.

$^1$H-NMR (CDCl$_3$) δ (ppm); 0.98 (3H, t, J=7 Hz), 1.10 (3H, br-s), 1.18 (3H, br-s), 1.58 (2H, m), 1.85 (2H, d, J=12 Hz), 2.30–2.60 (3H, m), 2.80 (2H, m), 3.03 (2H, m), 3.25 (2H, br-s), 3.50 (2H, br-s), 3.90–4.15 (4H, m), 4.32 (1H, m), 6.91 (2H, m), 7.00–7.15 (4H, m), 7.20–7.35 (6H, m), 9.92 (1H, s)

MS (TSP); m/z 555 (MH$^+$)

Example 76

8-[1-[2-(4-Diethylcarbamoylbenzyl)phenoxymethyl] propyl]-1-phenyl-1,3,8-triazaspiro[4,5]decan-4-one The title compound was obtained in the similar manner to that of Example 2 from 1-[2-(4-diethylcarbamoylbenzyl) phenoxymethyl]-1-methanesulfonyloxypropane obtained in the similar manner to that of Reference Example 1 and 1-phenyl-1,3,8-triazaspiro[4,5]decan-4-one. Yield: 19%.

$^1$H-NMR (CDCl$_3$) δ (ppm); 0.98 (3H, t, J=7 Hz), 1.10 (3H, br-s), 1.19 (3H, br-s), 1.50–1.75 (4H, m), 2.50–2.90 (6H, m), 3.00–3.10 (1H, m), 3.20–3.40 (4H, m), 3.50 (2H, br-s), 3.96 (1H, m), 4.02 (2H, s), 4.10 (1H, m), 6.80–6.95 (5H, m), 7.08 (1H, d, J=8 Hz), 7.15–7.30 (8H, m)

MS (TSP); m/z 569 (MH$^+$)

Example 77

1'-[2-[2-(4-Diethylcarbamoylbenzyl)phenoxy]ethyl] spiro[isobenzofuran-1(3H),4'-piperidin]-3-one The title compound was obtained in the same manner in Example 1 from the 1-[2-(4-diethylcarbamoylbenzyl) phenoxy]acetaldehyde obtained in Reference Example 2 and spiro[isobenzofuran-1(3H),4'-piperidin]-3-one hydrochloride synthesized in accordance with the descriptions of J. Org. Chem., 1976, 41, 2628. Yield: 44%.

$^1$H-NMR (CDCl$_3$) δ (ppm); 1.10 (3H, br-s), 1.20 (3H, br-s), 1.72 (2H, m), 2.23 (2H, m), 2.71 (2H, m), 2.91 (2H, m), 3.02 (2H, m), 3.26 (2H, br-s), 3.51 (2H, br-s), 4.00 (2H, s), 4.14 (2H, m), 6.89 (2H, m), 7.11 (1H, d, J=8 Hz), 7.19–7.28 (5H, m), 7.41 (1H, d, J=8 Hz), 7.53 (1H, t, J=8 Hz), 7.67 (1H, t, J=8 Hz), 7.88 (1H, d, J=8 Hz)

MS (FAB); m/z 513 (MH$^+$)

Example 78

1-[2-[2-(4-Diethylcarbamoylbenzyl)phenoxy]ethyl]-4-(6-fluoro-1H-indol-3-yl)piperidine The title compound was obtained in the same manner in Example 1 from the 1-[2-(4-diethylcarbamoylbenzyl) phenoxy]acetaldehyde obtained in Reference Example 2 and 4-(6-fluoro-1H-indol-3-yl)piperidine hydrochloride obtained in the same manner in J. Org. Chem., 1975, 40, 2525 and Helv. Chim. Acta, 1968, 51, 260. Yield: 44%.

$^1$H-NMR (CDCl$_3$) δ (ppm); 1.09 (3H, br-s), 1.21 (3H, br-s), 1.81 (2H, m), 2.02 (2H, m), 2.31 (2H, m), 2.85 (2H, t, J=5 Hz), 3.10 (2H, m), 3.25 (2H, br-s), 3.52 (2H, br-s), 4.01 (2H, s), 4.10 (1H, m), 4.14 (2H, t, J=5 Hz), 6.86 (4H, m), 7.01 (1H, d, J=8 Hz), 7.10 (1H, d, J=8 Hz), 7.22 (6H, m), 7.53 (1H, m)

MS (TSP); m/z 528 (MH$^+$)

Example 79

1-[2-[2-(4-Diethylcarbamoylbenzyl)-4-methoxyphenoxy]ethyl]-4-(1,3-dihydro-2H-benzimidazol-2-on-1-yl)piperidine The title compound was obtained in the same manner in Example 1 from 1-[2-(4-diethylcarbamoylbenzyl)-4-methoxyphenoxy]acetaldehyde obtained in the same manner in Reference Example 2 and 4-(1,3-dihydro-2H-benzimidazol-2-on-1-yl)piperidine. Yield: 80%.

$^1$H-NMR (CDCl$_3$) δ (ppm); 1.10 (3H, br-s), 1.20 (3H, br-s), 1.81 (2H, d, J=12 Hz), 2.33 (2H, t, J=12 Hz), 2.49 (2H, q, J=12 Hz), 2.82 (2H, t, J=5 Hz), 3.15 (2H, d, J=12 Hz), 3.24 (2H, br-s), 3.50 (2H, br-s), 3.74 (3H, s), 3.99 (2H, s), 4.08 (2H, t, J=5 Hz), 4.38 (1H, m), 6.65–6.80 (2H, m), 6.83 (1H, d, J=8 Hz), 7.00–7.15 (3H, m), 7.20–7.35 (5H, m), 9.84 (1H, s)

MS (TSP); m/z 557 (MH$^+$)

Example 80

8-[2-[2-(4-Diethylcarbamoylbenzyl)-4-methoxyphenoxy]ethyl]-1-phenyl-1,3,8-triazaspiro[4,5]decan-4-one The title compound was obtained in the same manner in Example 1 from 1-[2-(4-diethylcarbamoylbenzyl)-4-methoxyphenoxy]acetaldehyde obtained in the same manner in Reference Example 2 and 1-phenyl-1,3,8-triazaspiro[4,5] decan-4-one. Yield: 67%.

$^1$H-NMR (CDCl$_3$) δ (ppm); 1.10 (3H, br-s), 1.21 (3H, br-s), 1.70 (2H, d, J=12 Hz), 2.67 (2H, m), 2.80–3.05 (6H, m), 3.25 (2H, br-s), 3.49 (2H, br-s), 3.73 (3H, s), 3.98 (2H, s), 4.08 (2H, t, J=5 Hz), 4.72 (2H, s), 6.65–6.75 (2H, m), 6.80–6.95 (4H, m), 7.01 (1H, s), 7.20–7.30 (6H, m)

MS (TSP); m/z 571 (MH$^+$)

Example 81

1-[2-[2-(4-Diethylcarbamoylbenzyl)phenoxy]ethyl]-4-(1,3-dihydro-7-methyl-2H-benzimidazol-2-on-1-yl)piperidine The title compound was obtained in the same manner in Example 1 from the 1-[2-(4-diethylcarbamoylbenzyl) phenoxy]acetaldehyde obtained in Reference Example 2 and the 4-(1,3-dihydro-7-methyl-2H-benzimidazol-2-on-1-yl) piperidine hydrobromide obtained in Reference Example 11. Yield: 15%.

$^1$H-NMR (CDCl$_3$) δ (ppm); 1.10 (3H, br-s), 1.20 (3H, br-s), 1.78 (2H, m), 2.24 (2H, m), 2.59 (3H, s), 2.88 (4H, m), 3.16 (2H, m), 3.26 (2H, br-s), 3.51 (2H, br-s), 4.00 (2H, s), 4.14 (2H, m), 4.38 (1H, m), 6.80 (1H, m), 6.90 (5H, m), 7.09 (1H, d, J=8 Hz), 7.19–7.29 (4H, m), 9.86 (1H, s)

MS (EI); m/z 540 (M$^+$)

Example 82

1-[2-[2-(4-Diethylcarbamoylbenzyl)phenoxy]ethyl]-4-(5-fluoro-1,3-dihydro-2H-benzimidazol-2-on-1-yl) piperidine The title compound was obtained in the same manner in Example 1 from the 1-[2-(4-diethylcarbamoylbenzyl) phenoxy]acetaldehyde obtained in Reference Example 2 and the 4-(5-fluoro-1,3-dihydro-2H-benzimidazol-2-on-1-yl) piperidine hydrobromide obtained in the same manner in Reference Example 11. Yield: 18%.

$^1$H-NMR (CDCl$_3$) δ (ppm); 1.09 (3H, br-s), 1.20 (3H, br-s), 1.80 (2H, m), 2.32 (2H, m), 2.42 (2H, m), 2.84 (2H, t, J=5 Hz), 3.14 (2H, m), 3.25 (2H, br-s), 3.52 (2H, br-s), 4.00 (2H, s), 4.12 (2H, t, J=5 Hz), 4.34 (1H, m), 6.76 (1H, m), 6.83 (1H, m), 6.90 (2H, m), 7.10 (1H, d, J=8 Hz), 7.14–7.24 (6H, m), 9.82 (1H, s)

MS (FAB); m/z 545 (MH$^+$)

Example 83

1'-[2-[2-(4-Diethylcarbamoylbenzyl)phenoxy]ethyl]-2,3-dihydro-5-methylspiro[isoquinoline-4(1H),4'-piperidin]-1-one The title compound was obtained in the same manner in Example 1 from the 1-[2-(4-diethylcarbamoylbenzyl) phenoxy]acetaldehyde obtained in Reference Example 2 and the 2,3-dihydro-5-methylspiro[isoquinoline-4(1H),4'-piperidin]-1-one obtained in Reference Example 12. Yield: 56%.

$^1$H-NMR (CDCl$_3$) δ (ppm); 1.10 (3H, br-s), 1.23 (3H, br-s), 1.69 (2H, d, J=14 Hz), 2.25 (2H, t, J=14 Hz), 2.56 (2H, m), 2.63 (3H, s), 2.75 (2H, t, J=5 Hz), 2.85 (2H, d, J=14 Hz), 3.25 (2H, br-s), 3.50 (4H, m), 3.99 (2H, s), 4.12 (2H, t, J=5 Hz), 6.64 (1H, s), 6.85–6.95 (2H, m), 7.12 (1H, d, J=8 Hz), 7.15–7.30 (7H, m), 8.02 (1H, d, J=8 Hz)

MS (FAB); m/z 540 (MH$^+$)

Example 84

1-[2-[2-(4-Diethylcarbamoylbenzyl)phenoxy]ethyl]-4-(2-hydroxymethyl-1H-benzimidazol-1-yl) piperidine The title compound was obtained in the same manner in Example 1 from the 1-[2-(4-diethylcarbamoylbenzyl) phenoxy]acetaldehyde obtained in Reference Example 2 and 4-(2-hydroxymethyl-1H-benzimidazol-1-yl)piperidine obtained in the same manner in Reference Example 6. Yield: 12%.

$^1$H-NMR (CDCl$_3$) δ (ppm); 1.06 (3H, br-s), 1.15 (3H, br-s), 1.76 (2H, m), 2.18 (2H, m), 2.48 (2H, m), 2.89 (2H, m), 3.01 (2H, m), 3.20 (2H, br-s), 3.45 (2H, br-s), 4.03 (2H, s), 4.15 (2H, m), 4.48 (1H, m), 4.91 (2H, s), 6.89 (1H, m), 6.95 (1H, m), 7.19–7.26 (8H, m), 7.62 (1H, m), 7.71 (1H, m)

MS (TSP); m/z 541 (MH$^+$)

Example 85

1-[2-[2-(4-Diethylcarbamoylbenzyl)phenoxy]ethyl]-4-[2-(2-hydroxyethyl)-1H-benzimidazol-1-yl] piperidine The title compound was obtained in the same manner in Example 1 from the 1-[2-(4-diethylcarbamoylbenzyl) phenoxy]acetaldehyde obtained in Reference Example 2 and 4-[2-(2-hydroxyethyl)-1H-benzimidazol-1-yl]piperidine trifluoroacetate obtained in the same manner in Reference Example 6. Yield: 25%.

$^1$H-NMR (CDCl$_3$) δ (ppm); 1.00 (3H, br-s), 1.15 (3H, br-s), 1.84 (2H, m), 2.40 (2H, m), 2.60 (2H, m), 2.90 (2H, t, J=5 Hz), 3.16 (2H, t, J=7 Hz), 3.21 (4H, m), 3.44 (2H, br-s), 3.96 (2H, t, J=7 Hz), 4.06 (2H, s), 4.19 (2H, t, J=5 Hz), 4.50 (1H, m), 6.92 (1H, t, J=8 Hz), 7.00 (1H, d, J=8 Hz), 7.15–7.26 (8H, m), 7.56 (1H, m), 7.78 (1H, m)

MS (TSP); m/z 555 (MH$^+$)

Example 86

1-[2-[2-(4-Diethylcarbamoylbenzyl)phenoxy]ethyl]-4-(2-hydroxymethyl-7-methyl-1H-benzimidazol-1-yl)piperidine The title compound was obtained in the same manner in Example 1 from the 1-[2-(4-diethylcarbamoylbenzyl) phenoxy]acetaldehyde obtained in Reference Example 2 and the 4-(2-hydroxymethyl-7-methyl-1H-benzimidazol-1-yl) piperidine obtained in Reference Example 13. Yield: 44%.

$^1$H-NMR (CDCl$_3$) δ (ppm); 1.06 (3H, br-s), 1.16 (3H, br-s), 1.73 (2H, m), 2.17 (2H, m), 2.46 (2H, m), 2.62 (3H, s), 2.86 (2H, m), 2.99 (2H, m), 3.20 (2H, br-s), 3.46 (2H, br-s), 4.03 (2H, s), 4.13 (2H, m), 4.45 (1H, m), 4.94 (2H, s), 6.89 (1H, m), 6.94 (1H, m), 7.01 (1H, m), 7.07–7.26 (7H, m), 7.44 (1H, m)

MS (TSP); m/z 555 (MH$^+$)

Example 87

1-[2-[2-(4-Diethylcarbamoylbenzyl)phenoxy]ethyl]-4-(2-hydroxymethyl-7-methoxy-1H-benzimidazol-1-yl)piperidine The title compound was obtained in the same manner in Example 1 from the 1-[2-(4-diethylcarbamoylbenzyl) phenoxy]acetaldehyde obtained in Reference Example 2 and 4-(2-hydroxymethyl-7-methoxy-1H-benzimidazol-1-yl) piperidine obtained in the same manner in Reference Example 13. Yield: 39%.

$^1$H-NMR (CDCl$_3$) δ (ppm); 1.07 (3H, br-s), 1.17 (3H, br-s), 1.24 (2H, m), 2.26 (2H, m), 2.54 (2H, m), 2.85 (2H, m), 3.05 (2H, m), 3.21 (2H, br-s), 3.48 (2H, br-s), 3.95 (3H, s), 4.02 (2H, s), 4.12 (2H, m), 4.45 (1H, m), 4.90 (2H, s), 6.71 (1H, m), 6.90 (2H, m), 7.12–7.34 (8H, m)

MS (TSP); m/z 571 (MH$^+$)

Example 88

1-[2-[2-(4-Diethylcarbamoylbenzyl)phenoxy]ethyl]-4-(1,3-dihydro-2H-benzimidazol-2-on-1-yl)-3-methylpiperidine The title compound was obtained in the same manner in Example 1 from the 1-[2-(4-diethylcarbamoylbenzyl) phenoxy]acetaldehyde obtained in Reference Example 2 and 4-(1,3-dihydro-2H-benzimidazol-2-on-1-yl)-3-methylpiperidine synthesized in accordance with the descriptions of WO98/54168 and U.S. Pat. No. 5,756,508. Yield: 10%.

$^1$H-NMR (CDCl$_3$) δ (ppm); 1.00–1.40 (9H, m), 1.79 (1H, d, J=12 Hz), 2.20–2.40 (2H, m), 2.54 (1H, d, J=12 Hz), 2.75–2.90 (3H, m), 3.05 (1H, m), 3.10–3.35 (3H, m), 3.48 (2H, br-s), 4.00 (2H, s), 4.10 (2H, d, J=5 Hz), 4.39 (1H, dt, J=12 Hz, 3 Hz), 6.85–6.95 (2H, m), 7.00–7.15 (4H, m), 7.15–7.30 (6H, m), 9.95 (1H, s)

MS (TSP); m/z 541 (MH$^+$)

Example 89

1-[2-[2-(4-Diethylaminosulfonylbenzyl)phenoxy]
ethyl]-4-(2-hydroxymethyl-1H-benzimidazol-1-yl)
piperidine The title compound was obtained in the same manner in Example 1 from 1-[2-(4-diethylaminosulfonylbenzyl) phenoxy]acetaldehyde obtained in the same manner in Reference Example 2 and 4-(2-hydroxymethyl-1H-benzimidazol-1-yl)piperidine obtained in the same manner in Reference Example 6. Yield: 57%.

$^1$H-NMR (CDCl$_3$) δ (ppm); 1.08 (6H, t, J=7 Hz), 1.85 (2H, m), 2.26 (2H, m), 2.53 (2H, m), 2.81 (2H, t, J=5 Hz), 3.08 (2H, m), 3.17 (4H, q, J=7 Hz), 4.05 (2H, s), 4.12 (2H, t, J=5 Hz), 4.40 (1H, m), 4.90 (2H, s), 6.90 (1H, d, J=8 Hz), 6.94 (1H, t, J=8 Hz), 7.13 (1H, d, J=8 Hz), 7.20–7.27 (3H, m), 7.31 (2H, d, J=8 Hz), 7.61 (1H, m), 7.67 (2H, d, J=8 Hz), 7.70 (1H, m)

MS (TSP); m/z 577 (MH$^+$)

Example 90

1-[2-[2-(4-Diethylaminosulfonylbenzyl)phenoxy]
ethyl]-4-(1,3-dihydro-2H-benzimidazol-2-on-1-yl)
piperidine The title compound was obtained in the same manner in Example 1 from 1-[2-(4-diethylaminosulfonylbenzyl) phenoxy]acetaldehyde obtained in the same manner in Reference Example 2 and 4-(1,3-dihydro-2H-benzimidazol-2-on-1-yl)piperidine. Yield: 48%.

$^1$H-NMR (CDCl$_3$) δ (ppm); 1.09 (6H, t, J=7 Hz), 1.80 (2H, m), 2.31 (2H, m), 2.48 (2H, m), 2.81 (2H, m), 3.12 (2H, m), 3.19 (4H, q, J=7 Hz), 4.04 (2H, s), 4.13 (2H, m), 4.36 (1H, m), 6.90 (2H, m), 7.05 (2H, m), 7.09 (2H, m), 7.23 (2H, m), 7.32 (2H, d, J=8 Hz), 7.69 (2H, d, J=8 Hz), 9.87 (1H, s)

MS (TSP); m/z 563 (MH$^+$)

Example 91

8-[2-[2-(4-Diethylaminosulfonylbenzyl)phenoxy]
ethyl]-1-phenyl-1,3,8-triazaspiro[4,5]decan-4-one The title compound was obtained in the same manner in Example 1 from 1-[2-(4-diethylaminosulfonylbenzyl) phenoxy]acetaldehyde obtained in the same manner in Reference Example 2 and 1-phenyl-1,3,8-triazaspiro[4,5]decan-4-one. Yield: 44%.

$^1$H-NMR (CDCl$_3$) δ (ppm); 1.11 (6H, t, J=7 Hz), 1.66 (2H, m), 1.80 (2H, m), 2.59 (2H, m), 2.82–2.94 (4H, m), 3.18 (4H, q, J=7 Hz), 4.03 (2H, s), 4.12 (2H, m), 4.72 (2H, s), 6.83–6.93 (5H, m), 7.11 (1H, d, J=8 Hz), 7.24 (4H, m), 7.30 (2H, d, J=8 Hz), 7.66 (2H, d, J=8 Hz)

MS (TSP); m/z 577 (MH$^+$)

Example 92

1-[2-[2-(3-Diethylaminosulfonylbenzyl)phenoxy]
ethyl]-4-(2-hydroxymethyl-1H-benzimidazol-1-yl)
piperidine The title compound was obtained in the same manner in Example 1 from 1-[2-(3-diethylaminosulfonylbenzyl) phenoxy]acetaldehyde obtained in the same manner in Reference Example 2 and 4-(2-hydroxymethyl-1H-benzimidazol-1-yl)piperidine obtained in the same manner in Reference Example 6. Yield: 25%.

$^1$H-NMR (CDCl$_3$) δ (ppm); 1.09 (6H, t, J=7 Hz), 1.85 (2H, m), 2.27 (2H, m), 2.51 (2H, m), 2.85 (2H, t, J=5 Hz), 3.05 (2H, m), 3.20 (4H, q, J=7 Hz), 4.05 (2H, s), 4.12 (2H, t, J=5 Hz), 4.38 (1H, m), 4.91 (2H, s), 6.88 (1H, d, J=8 Hz), 6.94 (1H, t, J=8 Hz), 7.15 (1H, d, J=8 Hz), 7.23 (3H, m), 7.35 (2H, m), 7.60 (2H, m), 7.70 (2H, s)

MS (TSP); m/z 577 (MH$^+$)

Example 93

1-[2-[2-(3-Diethylaminosulfonylbenzyl)phenoxy]
ethyl]-4-(1,3-dihydro-2H-benzimidazol-2-on-1-yl)
piperidine The title compound was obtained in the same manner in Example 1 from 1-[2-(3-diethylaminosulfonylbenzyl) phenoxy]acetaldehyde obtained in the same manner in Reference Example 2 and 4-(1,3-dihydro-2H-benzimidazol-2-on-1-yl)piperidine. Yield: 31%.

$^1$H-NMR (CDCl$_3$) δ (ppm); 1.08 (6H, t, J=7 Hz), 1.83 (2H, m), 2.32 (2H, m), 2.48 (2H, m), 2.85 (2H, m), 3.12 (2H, m), 3.19 (4H, q, J=7 Hz), 4.04 (2H, s), 4.12 (2H, m), 4.36 (1H, m), 6.90 (2H, m), 7.04 (2H, m), 7.10 (2H, m), 7.21 (2H, m), 7.38 (2H, m), 7.60 (1H, d, J=8 Hz), 7.68 (1H, s), 9.95 (1H, s)

MS (TSP); m/z 563 (MH$^+$)

Example 94

8-[2-[2-(3-Diethylaminosulfonylbenzyl)phenoxy]
ethyl]-1-phenyl-1,3,8-triazaspiro[4,5]decan-4-one The title compound was obtained in the same manner in Example 1 from 1-[2-(3-diethylaminosulfonylbenzyl) phenoxy]acetaldehyde obtained in the same manner in Reference Example 2 and 1-phenyl-1,3,8-triazaspiro[4,5]decan-4-one. Yield: 33%.

$^1$H-NMR (CDCl$_3$) δ (ppm); 1.06 (6H, t, J=7 Hz), 1.71 (2H, m), 2.64 (2H, m), 2.86 (4H, m), 2.96 (2H, m), 3.18 (4H, q, J=7 Hz), 4.04 (2H, s), 4.12 (2H, m), 4.73 (2H, s), 6.84–6.92 (6H, m), 7.08 (1H, d, J=8 Hz), 7.19–7.28 (3H, m), 7.34 (1H, t, J=8 Hz), 7.40 (1H, d, J=8 Hz), 7.59 (1H, d, J=8 Hz), 7.67 (1H, s)

MS (TSP); m/z 577 (MH$^+$)

Example 95

1-[2-[2-[(5-Diethylcarbamoylfuran-2-yl)methyl]
phenoxy]ethyl]-4-(1,3-dihydro-2H-benzimidazol-2-
on-1-yl)piperidine The title compound was obtained in the same manner in Example 1 from 1-[2-[(5-diethylcarbamoylfuran-2-yl) methyl]phenoxy]acetaldehyde obtained in the same manner in Reference Example 2 and 4-(1,3-dihydro-2H-benzimidazol-2-on-1-yl)piperidine. Yield: 55%.

$^1$H-NMR (CDCl$_3$) δ (ppm); 1.16 (6H, t, J=7 Hz), 1.81 (2H, d, J=12 Hz), 2.35 (2H, t, J=12 Hz), 2.50 (2H, q, J=12 Hz), 2.87 (2H, t, J=5 Hz), 3.15 (2H, d, J=12 Hz), 3.47 (4H, q, J=7 Hz), 4.03 (2H, s), 4.15 (2H, t, J=5 Hz), 4.38 (1H, m), 6.10 (1H, d, J=3 Hz), 6.85–6.95 (3H, m), 7.00–7.30 (6H, m), 10.00 (1H, s)

MS (TSP); m/z 517 (MH$^+$)

Example 96

8-[2-[2-[(5-Diethylcarbamoylfuran-2-yl)methyl]
phenoxy]ethyl]-1-phenyl-1,3,8-triazaspiro[4,5]
decan-4-one The title compound was obtained in the same manner in Example 1 from 1-[2-[(5-diethylcarbamoylfuran-2-yl)

methyl]phenoxy]acetaldehyde obtained in the same manner in Reference Example 2 and 1-phenyl-1,3,8-triazaspiro[4,5]decan-4-one. Yield: 48%.

$^1$H-NMR (CDCl$_3$) δ (ppm); 1.16 (6H, t, J=7 Hz), 1.72 (2H, d, J=12 Hz), 2.67 (2H, m), 2.80–3.10 (6H, m), 3.47 (4H, q, J=7 Hz), 4.02 (2H, s), 4.15 (2H, t, J=5 Hz), 4.73 (2H, s), 6.09 (1H, d, J=3 Hz), 6.80–6.95 (6H, m), 7.10–7.30 (5H, m)

MS (TSP); m/z 531 (MH$^+$)

Example 97

1-[2-[2-[(5-Diethylcarbamoylfuran-2-yl)methyl]phenoxy]ethyl]-4-(2-hydroxymethyl-1H-benzimidazol-1-yl)piperidine The title compound obtained in the same manner in Example 1 from 1-[2-[(5-diethylcarbamoylfuran-2-yl)methyl]phenoxy]acetaldehyde obtained in the same manner in Reference Example 2 and 4-(2-hydroxymethyl-1H-benzimidazol-1-yl)piperidine obtained in the same manner in Reference Example 6. Yield: 50%.

$^1$H-NMR (CDCl$_3$) δ (ppm); 1.13 (6H, t, J=7 Hz), 1.87 (2H, d, J=12 Hz), 2.31 (2H, t, J=12 Hz), 2.53 (2H, q, J=12 Hz), 2.89 (2H, t, J=5 Hz), 3.11 (2H, d, J=12 Hz), 3.45 (4H, q, J=7 Hz), 4.02 (2H, s), 4.15 (2H, t, J=5 Hz), 4.46 (1H, m), 4.89 (2H, s), 6.04 (1H, d, J=3 Hz), 6.85–6.95 (3H, m), 7.15–7.30 (4H, m), 7.55–7.85 (2H, m)

MS (TSP); m/z 531 (MH$^+$)

Example 98

1'-[2-[2-(4-Diethylcarbamoylbenzyl)phenoxy]ethyl]-2,3-dihydro-5-methoxyspiro[isoquinoline-4(1H),4'-piperidin]-1-one The title compound was obtained in the same manner in Example 1 from the 1-[2-(4-diethylcarbamoylbenzyl)phenoxy]acetaldehyde obtained in Reference Example 2 and 2,3-dihydro-5-methoxyspiro[isoquinoline-4(1H),4'-piperidin]-1-one trifluoroacetate obtained in the same manner in Reference Example 12. Yield: 53%.

$^1$H-NMR (CDCl$_3$) δ (ppm); 1.10 (3H, br-s), 1.22 (3H, br-s), 1.59 (2H, d, J=12 Hz), 2.25 (2H, t, J=12 Hz), 2.75–2.95 (6H, m), 3.24 (2H, br-s), 3.45–3.60 (4H, m), 3.84 (3H, s), 3.99 (2H, s), 4.15 (2H, t, J=5 Hz), 6.48 (1H, br-s), 6.85–6.95 (2H, m), 7.02 (1H, d, J=8 Hz), 7.13 (1H, d, J=8 Hz), 7.15–7.35 (6H, m), 7.78 (1H, m)

MS (FAB); m/z 556 (MH$^+$)

Example 99

1-[2-[2-(4-Diethylaminomethylbenzyl)phenoxy]ethyl]-4-(2-hydroxymethyl-1H-benzimidazol-1-yl)piperidine The 1-[2-[2-(4-diethylcarbamoylbenzyl)phenoxy]ethyl]-4-(2-hydroxymethyl-1H-benzimidazol-1-yl)piperidine (64 mg) obtained in Example 84 was dissolved in tetrahydrofuran (1.3 ml), added with a solution of Red-Al in toluene (65%, 0.18 ml) and stirred at room temperature for 2.5 hours. After the reaction mixture was slowly poured into ice 10 g with ice cooling to quench the reaction and the layers were separated, the aqueous layer was extracted with dichloromethane (30 ml). The organic layer was dried over anhydrous magnesium sulfate, and then the solvent was evaporated under reduced pressure. The residue was purified by preparative thin layer silica gel column chromatography (developing solvent: dichloromethane:methanol:aqueous ammonia=9:1:0.1) to obtain 31 mg of the title compound. Yield: 50%.

$^1$H-NMR (CDCl$_3$) δ (ppm); 0.99 (6H, t, J=7 Hz), 1.75 (2H, d, J=12 Hz), 2.28 (2H, t, J=12 Hz), 2.40–2.60 (6H, m), 2.91 (2H, t, J=5 Hz), 3.03 (2H, d, J=12 Hz), 3.55 (2H, s) 4.00 (2H, s), 4.13 (2H, d, J=5 Hz), 4.42 (1H, m), 4.90 (2H, s), 6.87 (1H, d, J=8 Hz), 6.92 (1H, t, J=8 Hz), 7.10–7.30 (8H, m), 7.60 (1H, m), 7.69 (1H, m)

MS (TSP); m/z 527 (MH$^+$)

Example 100

1-[2-[2-(4-Diethylcarbamoylbenzyl)phenoxy]ethyl]-4-(2-hydroxymethyl-1H-benzimidazol-1-yl)-3-methylpiperidine The title compound was obtained in the same manner in Example 1 from the 1-[2-(4-diethylcarbamoylbenzyl)phenoxy]acetaldehyde obtained in Reference Example 2 and 4-(2-hydroxymethyl-1H-benzimidazol-1-yl)-3-methylpiperidine obtained in the same manner in Reference Example 13. Yield: 13%.

$^1$H-NMR (CDCl$_3$) δ (ppm); 1.07 (6H, m), 1.17 (3H, br-s), 1.80 (1H, d, J=12 Hz), 2.24 (2H, t, J=12 Hz), 2.42 (1H, d, J=12 Hz), 2.70–3.00 (4H, m), 3.12 (1H, d, J=12 Hz), 3.23 (2H, br-s), 3.47 (2H, br-s), 3.95–4.15 (4H, m), 4.58 (1H, dt, J=12 Hz, 5 Hz), 4.86 (1H, d, J=14 Hz), 4.92 (1H, d, J=14 Hz), 6.88 (1H, d, J=8 Hz), 6.92 (1H, t, J=8 Hz), 7.10–7.30 (8H, m), 7.51 (1H, m), 7.67 (1H, m)

MS (TSP); m/z 555 (MH$^+$)

Example 101

1-[2-[2-(3-Diethylcarbamoylbenzyl)phenoxy]ethyl]-4-(2-hydroxymethyl-1H-benzimidazol-1-yl)piperidine The title compound was obtained in the same manner in Example 1 from 1-[2-(3-diethylcarbamoylbenzyl)phenoxy]acetaldehyde obtained in the same manner in Reference Example 2 and 4-(2-hydroxymethyl-1H-benzimidazol-1-yl)piperidine obtained in the same manner in Reference Example 6. Yield: 55%.

$^1$H-NMR (CDCl$_3$) δ (ppm); 1.03 (3H, br-s), 1.21 (3H, br-s), 1.80 (2H, d, J=12 Hz), 2.22 (2H, t, J=12 Hz), 2.48 (2H, q, J=12 Hz), 2.87 (2H, t, J=5 Hz), 3.00 (2H, d, J=12 Hz), 3.19 (2H, br-s), 3.50 (2H, br-s), 4.02 (2H, s), 4.12 (2H, t, J=5 Hz), 4.42 (1H, m), 4.89 (2H, s), 6.80–6.95 (2H, m), 7.10–7.30 (8H, m), 7.55–7.85 (2H, m)

MS (TSP); m/z 541 (MH$^+$)

Example 102

1-[2-[2-(3-Diethylcarbamoylbenzyl)phenoxy]ethyl]-4-(2-hydroxymethyl-7-methyl-1H-benzimidazol-1-yl)piperidine The title compound was obtained in the same manner in Example 1 from 1-[2-(3-diethylcarbamoylbenzyl)phenoxy]acetaldehyde obtained in the same manner in Reference Example 2 and the 4-(2-hydroxymethyl-7-methyl-1H-benzimidazol-1-yl)piperidine obtained in Reference Example 13. Yield: 45%.

$^1$H-NMR (CDCl$_3$) δ (ppm); 1.02 (3H, br-s), 1.22 (3H, br-s), 1.78 (2H, d, J=12 Hz), 2.22 (2H, t, J=12 Hz), 2.48 (2H, q, J=12 Hz), 2.62 (3H, s), 2.87 (2H, t, J=5 Hz), 3.00 (2H, d, J=12 Hz), 3.17 (2H, br-s), 3.49 (2H, br-s), 4.02 (2H, s), 4.12

(2H, t, J=5 Hz), 4.43 (1H, m), 4.93 (2H, s), 6.80–7.30 (10H, m), 7.45 (1H, d, J=8 Hz)

MS (TSP); m/z 555 (MH$^+$)

Example 103

1-[2-[2-(4-Isobutyloxycarbonylbenzyl)phenoxy] ethyl]-4-(2-hydroxymethyl-1H-benzimidazol-1-yl) piperidine The title compound was obtained in the same manner in Example 1 from the 1-[2-(4-isobutyloxycarbonylbenzyl) phenoxy]acetaldehyde obtained in Reference Example 14 and 4-(2-hydroxymethyl-1H-benzimidazol-1-yl)piperidine obtained in the same manner in Reference Example 6. Yield: 40%.

$^1$H-NMR (CDCl$_3$) δ (ppm); 0.91 (6H, m), 1.83 (2H, m), 1.94 (1H, m), 2.29 (2H, m), 2.50 (2H, m), 2.83 (2H, m), 3.06 (2H, m), 3.99 (2H, m), 4.05 (2H, s), 4.12 (2H, m), 4.41 (1H, m), 4.86 (2H, s), 6.90 (2H, m), 7.20 (6H, m), 7.59 (1H, m), 7.68 (1H, m), 7.92 (2H, m)

MS (FAB); m/z 542 (MH$^+$)

Example 104

1-[2-[2-(4-Isobutyloxycarbonylbenzyl)phenoxy] ethyl]-4-(1,3-dihydro-2H-benzimidazol-2-on-1-yl) piperidine The title compound was obtained from the 1-[2-(4-isobutyloxycarbonylbenzyl)phenoxy]acetaldehyde obtained in Reference Example 14 and 4-(1,3-dihydro-2H-benzimidazol-2-on-1-yl)piperidine in the same manner in Example 1. Yield: 43%.

$^1$H-NMR (CDCl$_3$) δ (ppm); 0.96 (6H, m), 1.80 (2H, m), 2.05 (1H, m), 2.31 (2H, m), 2.47 (2H, m), 2.82 (2H, m), 3.10 (2H, m), 4.04 (4H, m), 4.12 (2H, m), 4.36 (1H, m), 6.90 (2H, m), 7.04 (2H, m), 7.10 (2H, m), 7.25 (4H, m), 7.95 (2H, m), 9.99 (1H, s)

MS (FAB); m/z 528 (MH$^+$)

Example 105

8-[2-[2-(4-Isobutyloxycarbonylbenzyl)phenoxy] ethyl]-1-phenyl-1,3,8-triazaspiro[4,5]decan-4-one The title compound was obtained in the same manner in Example 1 from the 1-[2-(4-isobutyloxycarbonylbenzyl) phenoxy]acetaldehyde obtained in Reference Example 14 and 1-phenyl-1,3,8-triazaspiro[4,5]decan-4-one. Yield: 46%.

$^1$H-NMR (CDCl$_3$) δ (ppm); 0.99 (6H, m), 1.69 (2H, m), 2.04 (1H, m), 2.64 (2H, m), 2.85 (4H, m), 2.94 (2H, m), 4.04 (4H, m), 4.12 (2H, m), 4.72 (2H, s), 6.89 (5H, m), 7.10 (1H, m), 7.26 (6H, m), 7.92 (2H, d, J=8 Hz)

MS (TSP); m/z 542 (MH$^+$)

Example 106

1-[2-[2-(4-Carboxybenzyl)phenoxy]ethyl]-4-(2-hydroxymethyl-1H-benzimidazol-1-yl)piperidine The 1-[2-[2-(4-isobutyloxycarbonylbenzyl)phenoxy] ethyl]-4-(2-hydroxymethyl-1H-benzimidazol-1-yl) piperidine (49 mg) obtained in Example 103 was dissolved in methanol (0.5 ml), added with 1 N aqueous sodium hydroxide (0.18 ml) and stirred at 50° C. for 2.5 hours. After the reaction mixture was added with 1 N aqueous hydrochloric acid (0.72 ml), the solvent was evaporated under reduced pressure. The residue was purified by LH-20 column chromatography (elution solvent: dichloromethane:methanol=1:1) to obtain 48.3 mg of the title compound as hydrochloride. Yield: 100%.

$^1$H-NMR (CDCl$_3$) δ (ppm); 2.15 (2H, m), 2.95 (2H, m), 3.30 (2H, m), 3.56 (2H, m), 3.68 (2H, m), 4.11 (2H, s), 4.45 (2H, m), 4.88 (1H, m), 5.19 (2H, s), 6.89 (1H, t, J=8 Hz), 7.04 (1H, d, J=8 Hz), 7.18 (1H, d, J=8 Hz), 7.24 (3H, m), 7.59 (2H, m), 7.78 (1H, m), 7.84 (2H, d, J=8 Hz), 8.29 (1H, m)

MS (TSP); m/z 486 (MH$^+$)

Example 107

1-[2-[2-[trans-(4-Diethylcarbamoylcyclohexyl) methyl]phenoxy]ethyl]-4-(1,3-dihydro-2H-benzimidazol-2-on-1-yl)piperidine The title compound was obtained in the same manner in Example 1 from 1-[2-[trans-(4-diethylcarbamoyl-cyclohexyl)methyl]phenoxy]acetaldehyde obtained in the same manner in Reference Example 2 and 4-(1,3-dihydro-2H-benzimidazol-2-on-1-yl)piperidine. Yield: 65%.

$^1$H-NMR (CDCl$_3$) δ (ppm); 1.02 (2H, m), 1.07 (3H, t, J=7 Hz), 1.15 (3H, t, J=7 Hz), 1.45–1.90 (9H, m), 2.30–2.60 (7H, m), 2.90 (2H, t, J=5 Hz), 3.15–3.40 (6H, m), 4.15 (2H, t, J=5 Hz), 4.41 (1H, m), 6.80–6.90 (2H, m), 7.00–7.35 (6H, m), 9.53 (1H, s)

MS (TSP); m/z 533 (MH$^+$)

Example 108

8-[2-[2-[trans-(4-Diethylcarbamoylcyclohexyl) methyl]phenoxy]ethyl]-1-phenyl-1,3,8-triazaspiro[4, 5]decan-4-one The title compound was obtained in the same manner in Example 1 from 1-[2-[trans-(4-diethylcarbamoyl-cyclohexyl)methyl]phenoxy]acetaldehyde obtained in the same manner in Reference Example 2 and 1-phenyl-1,3,8-triazaspiro[4,5]decan-4-one. Yield: 53%.

$^1$H-NMR (CDCl$_3$) δ (ppm); 1.02 (2H, m), 1.07 (3H, t, J=7 Hz), 1.15 (3H, t, J=7 Hz), 1.45–1.80 (9H, m), 2.35 (1H, m), 2.51 (2H, d, J=7 Hz), 2.70 (2H, m), 2.95 (4H, m), 3.12 (2H, m), 3.40 (4H, m), 4.15 (2H, t, J=5 Hz), 4.72 (2H, s), 6.80–6.95 (5H, m), 7.04 (2H, m), 7.15 (1H, m), 7.27 (2H, m)

MS (TSP); m/z 547 (MH$^+$)

Example 109

1-[2-[2-[trans-(4-Diethylcarbamoylcyclohexyl) methyl]phenoxy]ethyl]-4-(2-hydroxymethyl-1H-benzimidazol-1-yl)piperidine The title compound was obtained in the same manner in Example 1 from 1-[2-[trans-(4-diethylcarbamoylcyclo-hexyl)methyl]phenoxy]acetaldehyde obtained in the same manner in Reference Example 2 and 4-(2-hydroxymethyl-1H-benzimidazol-1-yl)piperidine obtained in the same manner in Reference Example 6. Yield: 66%.

$^1$H-NMR (CDCl$_3$) δ (ppm); 1.02 (2H, m), 1.07 (3H, t, J=7 Hz), 1.15 (3H, t, J=7 Hz), 1.45–1.80 (7H, m), 1.97 (2H, m), 2.45–2.70 (6H, m), 3.03 (2H, t, J=5 Hz), 3.15–3.40 (6H, m), 4.15 (2H, t, J=5 Hz), 4.72 (1H, m), 4.94 (2H, s), 6.80–6.90 (2H, m), 7.04 (1H, d, J=8 Hz), 7.15–7.30 (3H, m), 7.60–7.75 (2H, m)

MS (TSP); m/z 547 (MH$^+$)

Example 110

4-(2-Hydroxymethyl-1H-benzimidazol-1-yl)-1-[2-[2-[4-(2-methylbutyryl)benzyl]phenoxy]ethyl]piperidine The title compound was obtained in the same manner in Example 1 from the 1-[2-[4-(2-methylbutyryl)benzyl]phenoxy]acetaldehyde obtained in Reference Example 15 and 4-(2-hydroxymethyl-1H-benzimidazol-1-yl)piperidine obtained in the same manner in Reference Example 6. Yield: 59%.

$^1$H-NMR (CDCl$_3$) δ (ppm); 0.81 (3H, t, J=7 Hz), 1.10 (3H, d, J=7 Hz), 1.40 (1H, m), 1.74 (1H, m), 1.83 (2H, m), 2.30 (2H, m), 2.50 (2H, m), 2.84 (2H, m), 3.09 (2H, m), 3.30 (1H, m), 4.06 (2H, s), 4.15 (2H, m), 4.40 (1H, m), 4.88 (2H, s), 6.91 (2H, m), 7.14 (1H, m), 7.25 (5H, m), 7.60 (1H, m), 7.68 (1H, m), 7.84 (2H, d, J=8 Hz)

MS (FAB); m/z 526 (MH$^+$)

Example 111

1-[2-[2-[cis-(4-Diethylcarbamoylcyclohexyl)methyl]phenoxy]ethyl]-4-(1,3-dihydro-2H-benzimidazol-2-on-1-yl)piperidine The title compound was obtained in the same manner in Example 1 from 1-[2-[cis-(4-diethylcarbamoylcyclohexyl)methyl]phenoxy]acetaldehyde obtained in the same manner in Reference Example 2 and 4-(1,3-dihydro-2H-benzimidazol-2-on-1-yl)piperidine. Yield: 51%.

$^1$H-NMR (CDCl$_3$) δ (ppm); 1.10 (3H, t, J=7 Hz), 1.16 (3H, t, J=7 Hz), 1.48 (4H, m), 1.65 (1H, m), 1.75–2.00 (6H, m), 2.35–2.60 (5H, m), 2.72 (2H, d, J=7 Hz), 2.91 (2H, t, J=5 Hz), 3.15–3.40 (6H, m), 4.14 (2H, t, J=5 Hz), 4.41 (1H, m), 6.80–6.90 (2H, m), 7.00–7.20 (4H, m), 7.25–7.35 (2H, m), 9.83 (1H, s)

MS (TSP); m/z 533 (MH$^+$)

Example 112

8-[2-[2-[cis-(4-Diethylcarbamoylcyclohexyl)methyl]phenoxy]ethyl]-1-phenyl-1,3,8-triazaspiro[4,5]decan-4-one The title compound was obtained in the same manner in Example 1 from 1-[2-[cis-(4-diethylcarbamoylcyclohexyl)methyl]phenoxy]acetaldehyde obtained in the same manner in Reference Example 2 and 1-phenyl-1,3,8-triazaspiro[4,5]decan-4-one. Yield: 39%.

$^1$H-NMR (CDCl$_3$) δ (ppm); 1.10 (3H, t, J=7 Hz), 1.16 (3H, t, J=7 Hz), 1.40–1.50 (4H, m), 1.55–2.05 (8H, m), 2.47 (1H, m), 2.70 (3H, m), 2.95–3.10 (6H, m), 3.25–3.40 (4H, m), 4.15 (2H, m), 4.74 (2H, s), 6.80–6.95 (2H, m), 7.05–7.20 (3H, m), 7.25–7.35 (5H, m)

MS (TSP); m/z 547 (MH$^+$)

Example 113

1-[2-[2-[cis-(4-Diethylcarbamoylcyclohexyl)methyl]phenoxy]ethyl]-4-(2-hydroxymethyl-1H-benzimidazol-1-yl)piperidine The title compound was obtained in the same manner in Example 1 from 1-[2-[cis-(4-diethylcarbamoylcyclohexyl)methyl]phenoxy]acetaldehyde obtained in the same manner in Reference Example 2 and 4-(2-hydroxymethyl-1H-benzimidazol-1-yl)piperidine obtained in the same manner in Reference Example 6. Yield: 57%.

$^1$H-NMR (CDCl$_3$) δ (ppm); 1.07 (3H, t, J=7 Hz), 1.16 (3H, t, J=7 Hz), 1.48 (4H, m), 1.64 (1H, m), 1.80–2.10 (5H, m), 2.40–2.70 (6H, m), 2.73 (2H, d, J=7 Hz), 2.94 (2H, t, J=5 Hz), 3.20–3.40 (6H, m), 4.15 (2H, t, J=5 Hz), 4.54 (1H, m), 4.87 (2H, s), 6.80–6.95 (2H, m), 7.10–7.25 (4H, m), 7.60–7.75 (2H, m)

MS (TSP); m/z 547 (MH$^+$)

Example 114

2-Benzyl-1'-[2-[2-(4-diethylcarbamoylbenzyl)phenoxy]ethyl]2,3-dihydrospiro[isoquinoline-4(1H),4'-piperidin]-1-one The title compound was obtained in the same manner in Example 1 from the 1-[2-(4-diethylcarbamoylbenzyl)phenoxy]acetaldehyde obtained in Reference Example 2 and the 2-benzyl-2,3-dihydrospiro[isoquinoline-4(1H),4'-piperidin]-1-one obtained in Reference Example 16. Yield: 60%.

$^1$H-NMR (CDCl$_3$) δ (ppm); 1.10 (3H, br-s), 1.21 (3H, br-s), 1.49 (2H, d, J=14 Hz), 1.80 (2H, m), 2.48 (2H, td, J=14 Hz, 4 Hz), 2.58 (3H, s), 2.63 (2H, t, J=5 Hz), 2.70 (2H, m), 3.25 (2H, br-s), 3.45 (2H, s), 3.51 (2H, br-s), 3.97 (2H, s), 4.00 (2H, t, J=5 Hz), 4.75 (2H, s), 6.80–6.95 (2H, m), 7.08 (1H, d, J=8 Hz), 7.15–7.40 (12H, m), 8.11 (1H, t, J=8 Hz)

MS (FAB); m/z 630 (MH$^+$)

Example 115

2-(4-Diethylcarbamoylbenzyl)-1'-[2-[2-(4-diethylcarbamoylbenzyl)phenoxy]ethyl]-2,3-dihydrospiro[isoquinoline-4(1H),4'-piperidin]-1-one The title compound was obtained in the same manner in Example 1 from the 1-[2-(4-diethylcarbamoylbenzyl)phenoxy]acetaldehyde obtained in Reference Example 2 and 2-(4-diethylcarbamoylbenzyl)-2,3-dihydrospiro[isoquinoline-4(1H),4'-piperidin]-1-one obtained in the same manner in Reference Example 16. Yield: 24%.

$^1$H-NMR (CDCl$_3$) δ (ppm); 1.10 (6H, br-s), 1.22 (6H, br-s), 1.52 (2H, d, J=14 Hz), 1.95 (2H, m), 2.54 (2H, m), 2.59 (3H, s), 2.70 (4H, m), 3.24 (4H, br-s), 3.45 (2H, s), 3.52 (4H, br-s), 4.03 (2H, s), 4.05 (2H, t, J=5 Hz), 4.79 (2H, s), 6.90 (2H, t, J=8 Hz), 7.09 (1H, d, J=8 Hz), 7.15–7.40 (11H, m), 8.11 (1H, m)

MS (TSP); m/z 729 (MH$^+$)

Example 116

2-Cyclopropylmethyl-1'-[2-[2-(4-diethylcarbamoylbenzyl)phenoxy]ethyl]-2,3-dihydrospiro[isoquinoline-4(1H),4'-piperidin]-1-one The title compound was obtained in the same manner in Example 1 from the 1-[2-(4-diethylcarbamoylbenzyl)phenoxy]acetaldehyde obtained in Reference Example 2 and 2-cyclopropylmethyl-2,3-dihydrospiro[isoquinoline-4(1H),4'-piperidin]-1-one obtained in the same manner in Reference Example 16. Yield: 61%.

$^1$H-NMR (CDCl$_3$) δ (ppm); 0.34 (2H, m), 0.55 (2H, m), 1.00–1.30 (7H, m), 1.69 (2H, d, J=14 Hz), 2.39 (2H, t, J=14 Hz), 2.62 (3H, s), 2.64 (2H, m), 2.82 (2H, t, J=5 Hz), 2.92 (2H, d, J=14 Hz), 3.25 (2H, br-s), 3.45 (2H, d, J=7 Hz), 3.50 (2H, br-s), 3.64 (2H, s), 3.99 (2H, s), 4.13 (2H, t, J=5 Hz), 6.85–6.95 (2H, m), 7.09 (1H, d, J=8 Hz), 7.15–7.30 (7H, m), 8.04 (1H, m)

MS (TSP); m/z 594 (MH$^+$)

Example 117

2-(3-Diethylcarbamoylbenzyl)-1'-[2-[2-(4-diethylcarbamoylbenzyl)phenoxy]ethyl]-2,3-dihydrospiro[isoquinoline-4(1H),4'-piperidin]-1-one The title compound was obtained in the same manner in Example 1 from the 1-[2-(4-diethylcarbamoylbenzyl)phenoxy]acetaldehyde obtained in Reference Example 2 and 2-(3-diethylcarbamoylbenzyl)-2,3-dihydrospiro[isoquinoline-4(1H),4'-piperidin]-1-one obtained in the same manner in Reference Example 16. Yield: 56%.

$^1$H-NMR (CDCl$_3$) δ (ppm); 1.09 (6H, br-s), 1.22 (6H, br-s), 1.53 (2H, d, J=14 Hz), 1.93 (2H, m), 2.53 (2H, m), 2.59 (3H, s), 2.71 (4H, m), 3.23 (4H, br-s), 3.47 (2H, s), 3.51 (4H, br-s), 3.97 (2H, s), 4.05 (2H, t, J=5 Hz), 4.79 (2H, s), 6.85–6.95 (2H, m), 7.09 (1H, d, J=8 Hz), 7.15–7.40 (11H, m), 8.11 (1H, m)

MS (TSP); m/z 729 (MH$^+$)

Example 118

4-(N-Acetylanilino)-1-[2-[2-(4-diethylcarbamoylbenzyl)phenoxy]ethyl]piperidine

The title compound was obtained in the same manner in Example 1 from the 1-[2-(4-diethylcarbamoylbenzyl)phenoxy]acetaldehyde obtained in Reference Example 2 and 4-(N-acetylanilino)piperidine. Yield: 73%.

$^1$H-NMR (CDCl$_3$) δ (ppm); 1.12 (3H, br-s), 1.22 (3H, br-s), 1.40 (2H, qd, J=12 Hz, 4 Hz), 1.74 (3H, s), 1.77 (2H, d, J=12 Hz), 2.27 (2H, t, J=12 Hz), 2.72 (2H, t, J=5 Hz), 2.97 (2H, d, J=12 Hz), 3.27 (2H, br-s), 3.53 (2H, br-s), 3.94 (2H, s), 4.00 (2H, t, J=5 Hz), 4.65 (1H, m), 6.79 (1H, d, J=8 Hz), 6.86 (1H, t, J=8 Hz), 7.00–7.45 (11H, m)

MS (FAB); m/z 528 (MH$^+$)

Test Example 1

Binding Affinity for Opioid δ Receptor

A membrane fraction of opioid δ receptor was prepared from the rat forebrain. For the preparation of the membrane fraction, the rat forebrain was homogenized in a 10-fold volume of 0.32 M sucrose solution, and the resulting homogenate was centrifuged at 900×g for 10 minutes. Subsequently, the supernatant was centrifuged at 11,500×g for 20 minutes to obtain precipitates. The precipitates were washed with an assay buffer (50 mM Tris-HCl, pH 7.4) by centrifugation, and the finally obtained membrane fraction was used for the experiment.

A binding experiment was performed by using the resulting membrane fraction and a radioactive ligand [$^3$H]-Naltrindole. In the presence of a test compound, the membrane fraction and [$^3$H]-Naltrindole at a final concentration of 1 nM were added and incubated at 25° C. for 90 minutes. The membrane fraction mixture was rapidly filtered through a GF/B filter to quench the reaction and further washed with the assay buffer (5 ml). The radioactivity was measured by a liquid scintillation counter. Amount of non-specific bindings was determined by using 10 μM Naltrindole, and amount of specific bindings was calculated from the difference of the amounts of measured bindings and the non-specific bindings. IC$_{50}$ value of each compound was determined by nonlinear least square regression analysis, and Ki value was calculated by using the Cheng-Prusoff equation.

The results of the measurement of opioid δ receptor binding affinity of the compounds of the present invention by the above method are shown in Table 1 below.

TABLE 1

|  | Binding affinity Ki (nM) |
|---|---|
| Compound of Example 15 | 281 |
| Compound of Example 29 | 235 |
| Compound of Example 32 | 517 |
| Compound of Example 33 | 467 |
| Compound of Example 36 | 240 |
| Compound of Example 40 | 243 |
| Compound of Example 49 | 943 |
| Compound of Example 88 | 767 |
| Compound of Example 103 | 73 |
| Compound of Example 107 | 133 |
| Compound of Example 110 | 88 |
| Compound of Example 114 | 1530 |

Industrial Applicability

The compounds of the present invention have effective and selective affinity for opioid δ receptors. The provision of medicaments consisting the compound described above will greatly contribute to therapeutic treatments of central nerve system diseases including schizophrenia, depression, cerebral apoplexy, epilepsy, Alzheimer's disease and Parkinson's disease and peripheral nerve system diseases including pains.

What is claimed is:

1. A compound represented by the following formula (I) or a salt thereof:

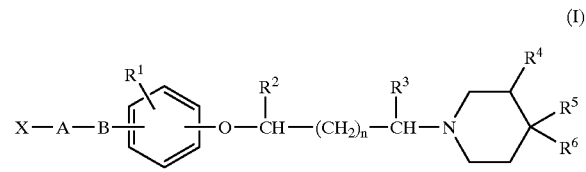

wherein, X represents the following group (II), (III), (IV), (V), or (VI),

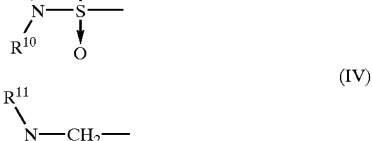

"A" represents a saturated or unsaturated 6-membered carbocyclic group selected from the group consisting of benzene and cyclcohexane, "B" represents —CH$_2$— or a single bond, "n" represents 0, 1 or 2, R$^1$ represents a hydrogen atom, a halogen atom, a lower alkyl group which may be substituted, a lower alkenyl group which may be substituted, a lower alkoxy group which may be substituted, a hydroxy group, a cyano group, an amino group, a N,N-di(lower alkyl)amino group, a N,N-di(substituted lower alkyl)amino group, a nitro group, a carbamoyl group, a N,N-di(lower alkyl) carbamoyl group, a N,N-di(substituted lower alkyl) carbamoyl group, a carboxyl group, a lower alkoxycarbonyl group which may be substituted or a lower alkylcarbonyl group which may be substituted, R$^2$, R$^3$, R$^7$, R$^8$, R$^9$, R$^{10}$, R$^{11}$, R$^{12}$, R$^{13}$, and R$^{14}$ independently represent a hydrogen atom, a lower alkyl group which may be substituted or a lower alkenyl group which may be substituted, R$^4$ represents a hydrogen atom, a lower alkyl group which may be substituted, a lower alkenyl group which may be substituted, or a lower alkoxy group which may be substituted, R$^5$ and R$^6$ bind to each other to represent the following group (VIII) or (XVI):

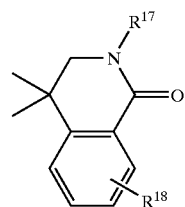

(VIII)

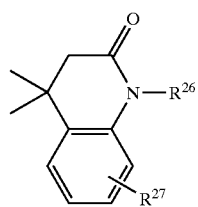

(XVI)

wherein, R$^{17}$ or R$^{26}$ represents a hydrogen atom, a lower alkyl group which may be substituted, or a lower alkenyl group which may be substituted, and R$^{18}$ or R$^{27}$ represents a hydrogen atom, a halogen atom, a lower alkyl group which may be substituted, a lower alkenyl group which may be substituted, a lower alkoxy group which may be substituted, a hydroxy group, a cyano group, an amino group, a N,N-di(lower alkyl)amino group, a N,N-di(substituted lower alkyl) amino group, a nitro group, a carbamoyl group, a N,N-di(lower alkyl)carbamoyl group, a N,N-di (substituted lower alkyl)carbamoyl group, a carboxyl group, a lower alkoxycarbonyl group which may be substituted, or a lower alkylcarbonyl group which may be substituted.

2. The compound or a salt thereof according to claim 1, wherein X represents the group (II), (III), (V), or (VI), "A" is a ring selected from the group consisting of benzene and cyclohexane, "B" represents —CH$_2$— or a single bond, "n" represents 0, 1, or 2, R$^1$ represents a hydrogen atom or a lower alkoxy group, R$^2$, R$^3$, R$^7$, R$^8$, R$^9$, R$^{10}$, R$^{13}$, and R$^{14}$ each independently represent a hydrogen atom or a lower alkyl group which may be substituted, R$^4$ represents a hydrogen atom or a lower alkyl group which may be substituted.

3. The compound or a salt thereof according to claim 1, wherein X represents the group (II).

4. A pharmaceutical composition, said pharmaceutical composition comprising at least one compound of formula (1) according to claim 1, and a pharmacologically acceptable salt thereof as an active ingredient.

5. The pharmaceutical composition according to claim 4, wherein the composition further comprises one or more pharmaceutical additives.

6. The pharmaceutical composition according to claim 4, which has affinity for an opioid δ receptor.

7. A method for therapeutic treatment of a central nerve system disease selected from the group consisting of schizophrenia, depression, cerebral apoplexy, epilepsy, Alzheimer's disease and Parkinson's disease, which comprises administering a therapeutically effective amount of at least one compound according to claim 1 and a pharmacologically acceptable salt thereof to a mammal.

8. A method for therapeutic treatment of pain in diseases of the peripheral nerve system, which comprises administering a therapeutically effective amount of at least one compound according to claim 1 and a pharmacologically acceptable salt thereof to a mammal.

9. The method according to claim 7, wherein the mammal is a human.

10. The method according to claim 8, wherein the mammal is a human.

* * * * *

UNITED STATES PATENT AND TRADEMARK OFFICE
CERTIFICATE OF CORRECTION

PATENT NO. : 6,916,822 B2
DATED : July 12, 2005
INVENTOR(S) : M. Tsushima et al.

It is certified that error appears in the above-identified patent and that said Letters Patent is hereby corrected as shown below:

Title page,
Item [*] Notice, insert -- This patent is subject to a terminal disclaimer --.

Column 68,
Line 67, "cyclcohexane" should be -- cyclohexane --.

Signed and Sealed this

Third Day of January, 2006

JON W. DUDAS
*Director of the United States Patent and Trademark Office*